(12) United States Patent
Eastman et al.

(10) Patent No.: US 8,962,651 B2
(45) Date of Patent: Feb. 24, 2015

(54) COMPOUNDS FOR THE TREATMENT OF HEPATITIS C

(71) Applicant: Bristol-Myers Squibb Company, Princeton, NJ (US)

(72) Inventors: Kyle J. Eastman, Killingworth, CT (US); Kyle E. Parcella, Wallingford, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/204,292

(22) Filed: Mar. 11, 2014

(65) Prior Publication Data
US 2014/0275154 A1 Sep. 18, 2014

Related U.S. Application Data

(60) Provisional application No. 61/915,729, filed on Dec. 13, 2013, provisional application No. 61/778,936, filed on Mar. 13, 2013.

(51) Int. Cl.
| | |
|---|---|
| *A61K 31/44* | (2006.01) |
| *C07D 471/02* | (2006.01) |
| *C07D 491/02* | (2006.01) |
| *C07D 498/02* | (2006.01) |
| *C07D 491/048* | (2006.01) |
| *C07D 491/04* | (2006.01) |

(52) U.S. Cl.
CPC .......... *C07D 491/048* (2013.01); *C07D 491/04* (2013.01)
USPC .......................................... 514/302; 546/115

(58) Field of Classification Search
USPC .......................................... 546/115; 514/302
See application file for complete search history.

(56) References Cited

U.S. PATENT DOCUMENTS

| | | | |
|---|---|---|---|
| 7,994,171 B2 | 8/2011 | Yeung et al. | |
| 8,048,887 B2 | 11/2011 | Yeung et al. | |
| 8,148,382 B2 | 4/2012 | Yeung et al. | |
| 8,198,449 B2 * | 6/2012 | Pracitto et al. | ................ 546/121 |
| 8,293,909 B2 | 10/2012 | Pracitto et al. | |
| 8,309,558 B2 | 11/2012 | Yeung et al. | |
| 8,536,338 B2 | 9/2013 | Pracitto et al. | |
| 8,722,688 B2 | 5/2014 | Yeung et al. | |
| 2012/0316126 A1 | 12/2012 | Yeung et al. | |

* cited by examiner

*Primary Examiner* — Niloofar Rahmani
(74) *Attorney, Agent, or Firm* — James Epperson

(57) ABSTRACT

The disclosure provides compounds of formula I, including their salts, as well as compositions and methods of using the compounds. The compounds have activity against hepatitis C virus (HCV) and may be useful in treating those infected with HCV.

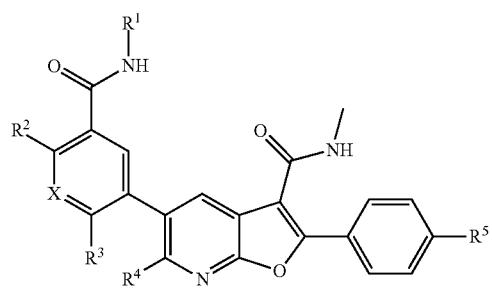

8 Claims, No Drawings

COMPOUNDS FOR THE TREATMENT OF HEPATITIS C

CROSS-REFERENCE TO RELATED APPLICATIONS

This application claims priority to U.S. Provisional Patent Application 61/915,729, filed Dec. 13, 2013 and U.S. Provisional Patent Application 61/778,936, filed Mar. 13, 2013, hereby incorporated by reference in their entireties.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens. U.S. Pat. No. 7,265,152 and the corresponding PCT patent application WO2004/041201 describe compounds of the HCV-796 class. Other compounds have been disclosed, see for example, WO2009/101022.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

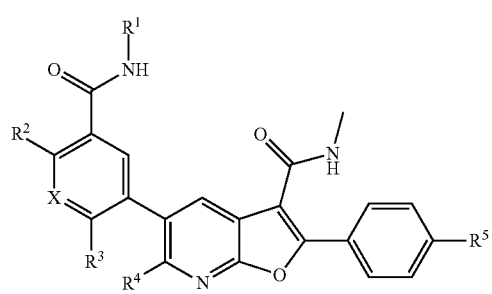

where:

$R^1$ is

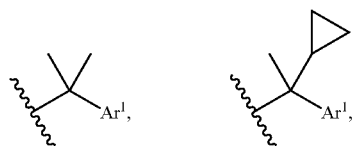

-continued

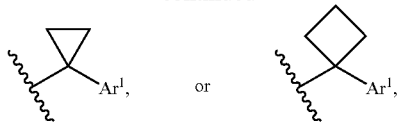

where the alkyl, cycloalkyl, or Ar¹ moieties may have hydrogen or deuterium atoms;
R² is hydrogen, fluoro, methoxy, or CD₃O;
R³ is hydrogen;
R⁴ is s-butyl, trifluoropropyl, trifluoroethoxy, or trifluoroethylamino;
R⁵ is fluoro;
Ar¹ is

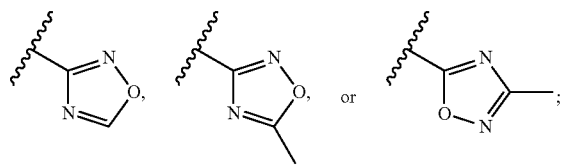

and
X is CH or N;
or a pharmaceutically acceptable salt thereof

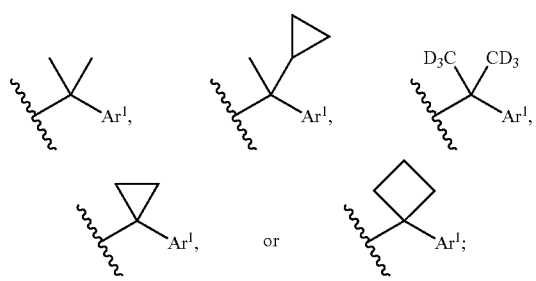

Another aspect of the invention is a compound of formula I where R¹ is
R² is hydrogen, fluoro, methoxy, or CD₃O;
R³ is hydrogen;
R⁴ is s-butyl, trifluoropropyl, trifluoroethoxy, or trifluoroethylamino;
R⁵ is fluoro;
Ar¹ is

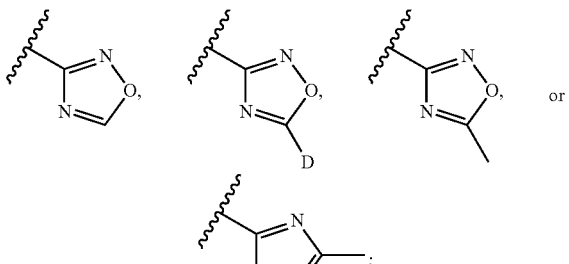

and
X is CH or N;
or a pharmaceutically acceptable salt thereof.

Another aspect of the invention is a compound of formula I where:
R¹ is (Ar¹)alkyl or (Ar¹)cycloalkyl;
R² is hydrogen, halo, alkyl, or alkoxy;
R³ is hydrogen;
R⁴ is alkyl, haloalkyl, or haloalkylamino;
R⁵ is halo; and
Ar¹ is oxadiazolyl substituted with 0-2 alkyl substituents;
or a pharmaceutically acceptable salt thereof.

Another aspect of the invention is a compound of formula I where R¹ is (Ar¹)alkyl or (Ar¹)cycloalkyl.

Another invention is a compound of formula I where R¹ is

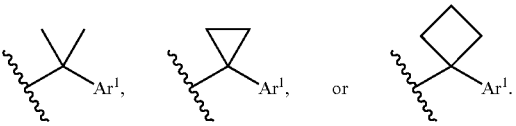

Another invention is a compound of formula I where R¹ is

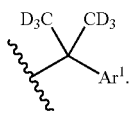

Another invention is a compound of formula I where R² is hydrogen, halo, alkyl, or alkoxy.

Another invention is a compound of formula I where R² is hydrogen, fluoro, or methoxy.

Another invention is a compound of formula I where R² is CD₃O.

Another invention is a compound of formula I where R³ is hydrogen.

Another invention is a compound of formula I where R⁴ is alkyl, haloalkyl, or halo alkylamino.

Another invention is a compound of formula I where R⁴ is s-butyl, trifluoropropyl, or trifluoroethylamino.

Another invention is a compound of formula I where R⁵ is halo.

Another invention is a compound of formula I where R⁵ is fluoro.

Another invention is a compound of formula I where Ar¹ is oxadiazolyl substituted with 0-2 alkyl substituents.

Another invention is a compound of formula I where Ar¹ is

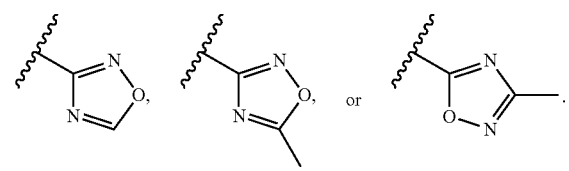

Another invention is a compound of formula I where Ar¹ is

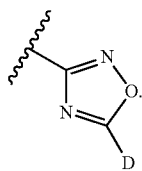 [SMILES: *c1noc([2H])n1]

Any scope of any variable, including $R^1$, $R^2$, $R^3$, $R^4$, $R^5$, X, and $Ar^1$, can be used independently with the scope of any other instance of a variable.

Unless specified otherwise, these terms have the following meanings "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." Ethylene means ethanediyl or —$CH_2CH_2$—; propylene means propanediyl or —$CH_2CH_2CH_2$—; butylene means butanediyl or —$CH_2CH_2CH_2CH_2$—; pentylene means pentanediyl or —$CH_2CH_2CH_2CH_2CH_2$—. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucuronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon or a ribavirin. Another aspect of the invention is where the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixirs, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regimen, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regimen, however, will be determined by a physician using sound medical judgment.

Some examples of compounds suitable for compositions and methods are listed in Table 1.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts | Antiviral | HCV Inhibitors | Arrow Therapeutics Ltd. |

TABLE 1-continued

| Brand Name | Physiological Class | Type of Inhibitor or Target | Source Company |
|---|---|---|---|
| From WO-2005047288 26 May 2005 | | | |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immuno-modulator | immune modulator | Maxim Pharmaceuticals Inc., San Diego, CA |
| CellCept | Immuno-suppressant | HCV IgG immuno-suppressant | F. Hoffmann-La Roche LTD, Basel, Switzerland |
| Civacir | Immuno-suppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1α | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | sense protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |

TABLE 1-continued

| Brand Name | Physiological Class | Type of Inhibitor or Target | Source Company |
|---|---|---|---|
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Gilead (formerly from Pharmasset) |
| PSI-7977 sofosbuvir | Antiviral | Nucleotide NS5B Polymerase Inhibitor | Gilead (formerly from Pharmasset) |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/ Bristol-Myers Squibb |
| asunaprevir | Antiviral | serine protease inhibitor | Bristol-Myers Squibb |
| BMS-791325 | Antiviral | NS5B Polymerase Inhibitor | Bristol-Myers Squibb |
| daclatasvir | Antiviral | HCV NS5A replication complex inhibitor | Bristol-Myers Squibb |
| GS-5885 | Antiviral | HCV NS5A replication complex inhibitor | Gilead |

Synthetic Methods

The compounds may be made by methods known in the art including those described below. Some reagents and intermediates are known in the art. Other reagents and intermediates can be made by methods known in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "DMSO" for dimethylsulfoxide; "h" for hours; "rt" or "RT" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine; TEA for triethylamine; DCM for dichloromethane Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "A" for microliter or microliters, "N" for normal, "M" for molar, "mmol" for millimole or millimoles, "min" for minute or minutes, "h" for hour or hours, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Routes—to prepare compounds of the invention are shown in Schemes 1-13.

Scheme 1.

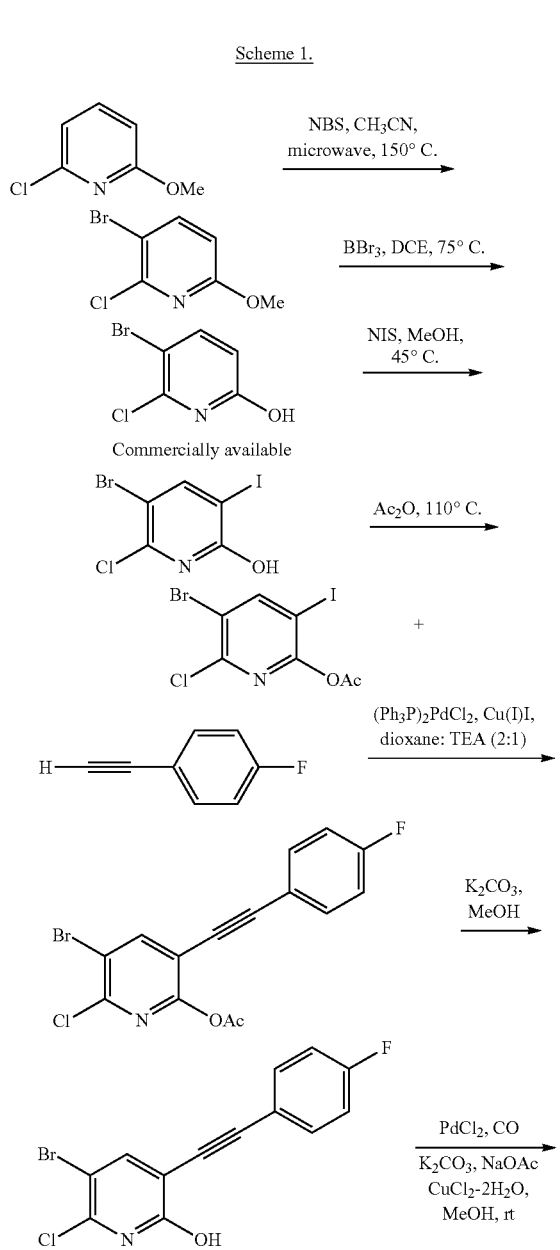

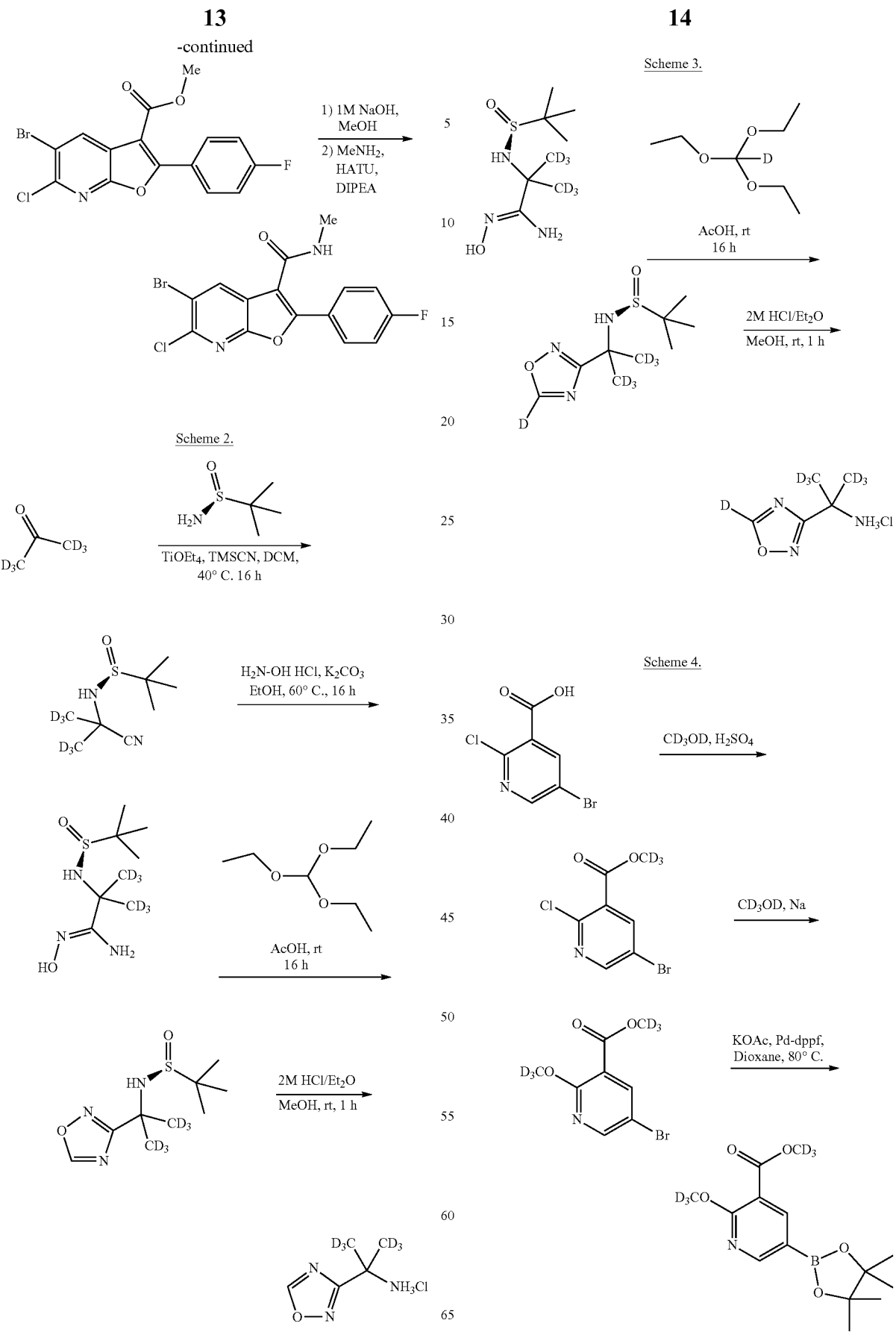

Scheme 5.
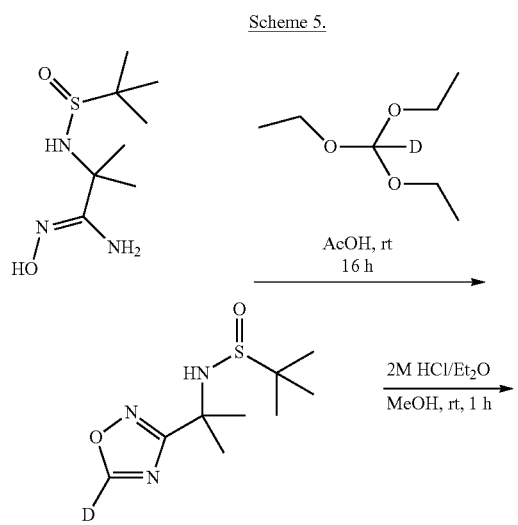
Scheme 6.
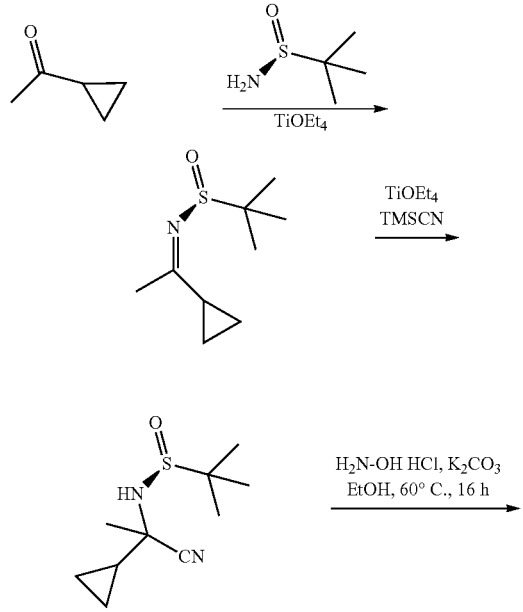
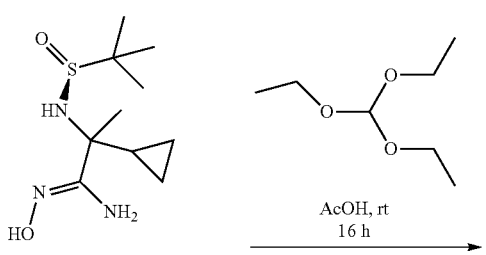
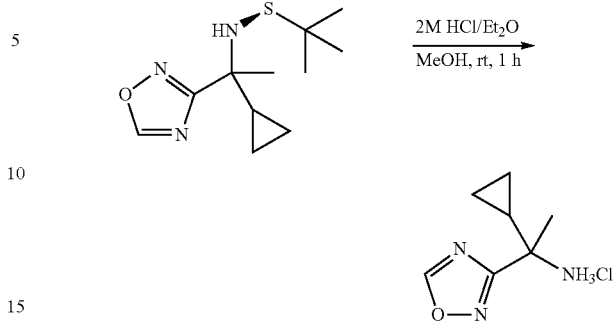
Scheme 7.
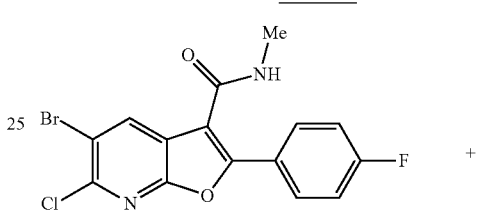
Y = H, F, OMe, or OCD$_3$
Z = CH or N
Scheme 8.
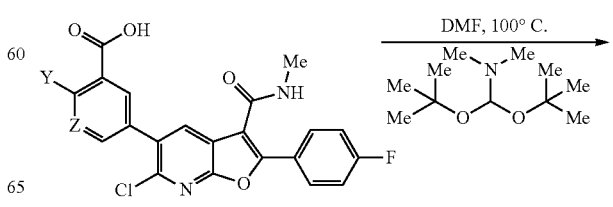

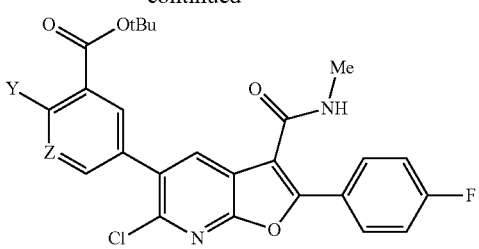
Y = H, F, OMe, or OCD₃
Z = CH or N
Scheme 9.
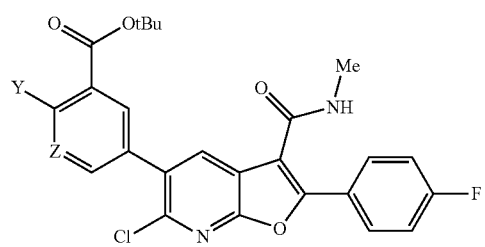
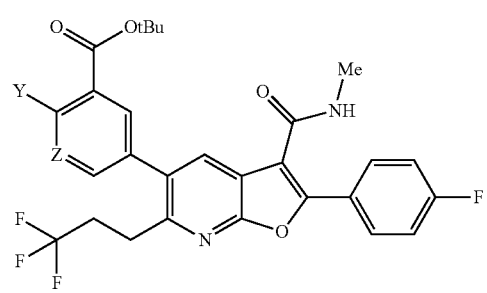
Y = H, F, OMe, or OCD₃
Z = CH or N
Scheme 10.
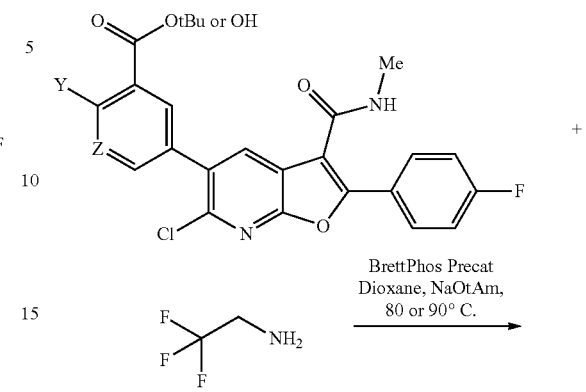
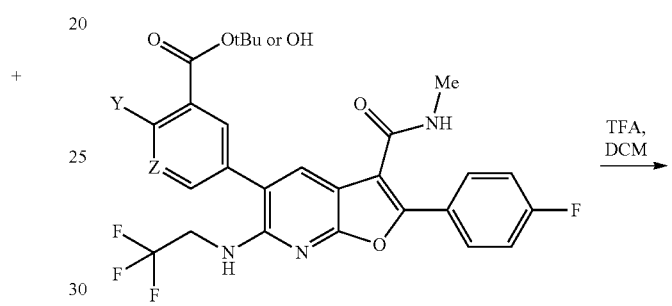
Y = H, F, OMe, or OCD₃
Z = CH or N
Scheme 11.
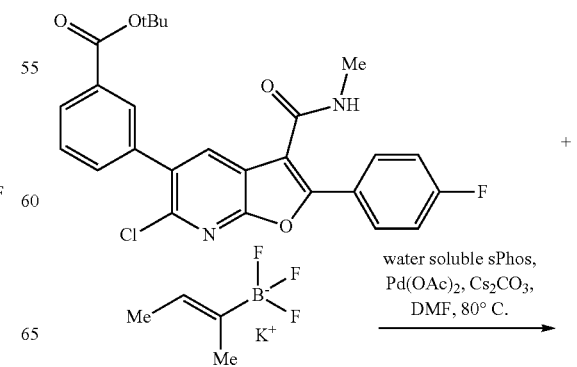

-continued
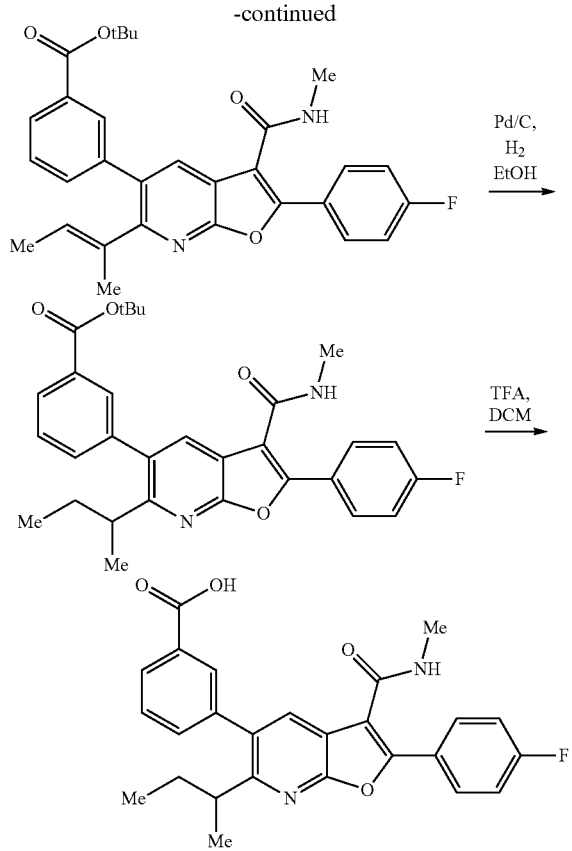
Scheme 13.
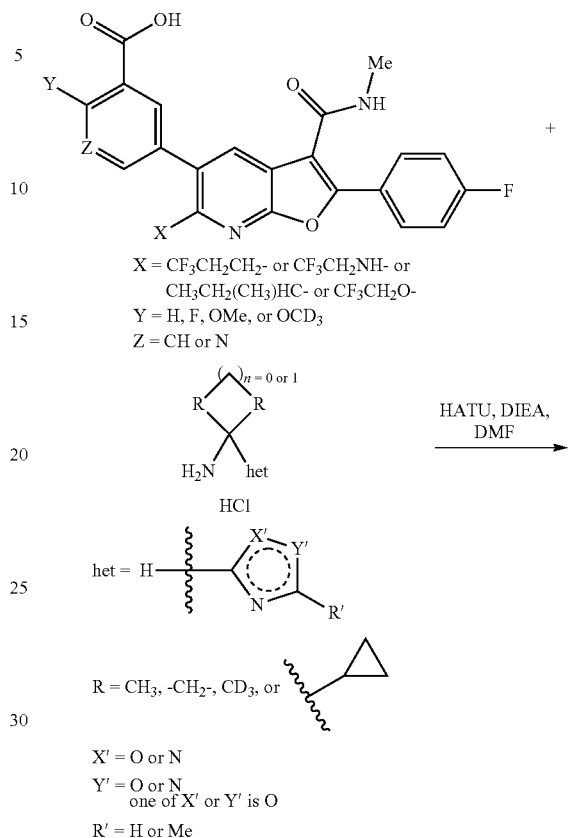
X = CF₃CH₂CH₂- or CF₃CH₂NH- or
CH₃CH₂(CH₃)HC- or CF₃CH₂O-
Y = H, F, OMe, or OCD₃
Z = CH or N
$X' = O$ or $N$
$Y' = O$ or $N$
 one of $X'$ or $Y'$ is O
$R' = H$ or $Me$
R = CH₃, -CH₂-, CD₃, or cyclopropyl
Scheme 12.
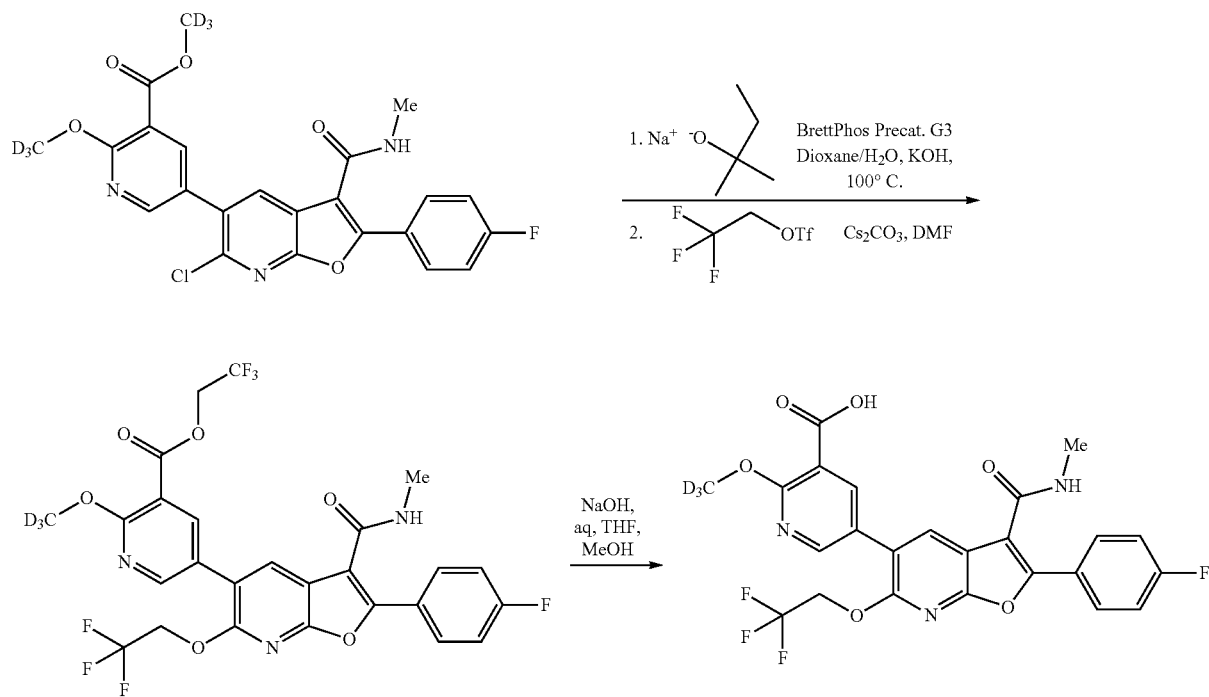

-continued

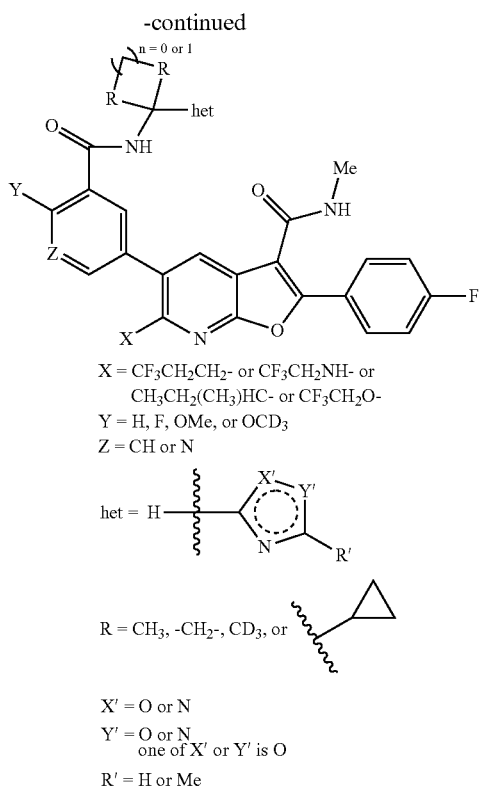

X = CF₃CH₂CH₂- or CF₃CH₂NH- or
CH₃CH₂(CH₃)HC- or CF₃CH₂O-
Y = H, F, OMe, or OCD₃
Z = CH or N het =

R = CH₃, -CH₂-, CD₃, or

X' = O or N
Y' = O or N
one of X' or Y' is O
R' = H or Me

DESCRIPTION OF SPECIFIC EMBODIMENTS

5-bromo-6-chloro-3-iodopyridin-2-ol

NIS (7.38 g, 32.8 mmol) was added to a stirring solution of commercially available 5-bromo-6-chloropyridin-2-ol (5.70 g, 27.3 mmol) in MeOH (50 ml) at 45° C. The reaction was allowed to stir at 45° C. for 1 h. The amber colored solution was cooled to rt and then concentrated in vacuo. The resulting yellow solids were diluted with 25 mL DCM, triturated for 30 min, then collected filtering with minimal DCM to give 5-bromo-6-chloro-3-iodopyridin-2-ol (7.60 g, 22.7 mmol, 83% yield) as a white solid consistent by LCMS and NMR. LCMS: m/e 335 (M+H)⁺ LCMS retention time: 2.62 min. (Column: Phenomenex-Luna 50×2.0 mm 3u. Solvent A=90% Water: 10% Methanol: 0.1% TFA. Solvent B=10% Water: 90% Methanol: 0.1% TFA. Start % B=0. Final % B=100. Gradient Time=4 min. Flow Rate=0.8 mL/min.). ¹H NMR (500 MHz, MeOD) δ ppm 8.26 (s, 1H).

5-bromo-6-chloro-3-iodopyridin-2-yl acetate 5-bromo-6-chloro-3-iodopyridin-2-ol (12.9 g, 38.6 mmol) was suspended in acetic anhydride (40 mL, 420 mmol) and heated to 110° C. The mixture was heated at this temp for 1 h. After 1 h the reaction mixture appeared as a homogeneous solution. TLC (observed M+H mass in LCMS is primarily of des-OAc) indicated complete reaction. The solution was concentrated azeotroping with toluene (3×25 mL) to give 5-bromo-6-chloro-3-iodopyridin-2-yl acetate (14.5 g, 38.5 mmol, 100% yield) as a tan solid. The solid was taken onto the subsequent Sonogashira coupling without further purification. Observed LCMS reveals mostly hydrolysis product (starting material), but desired mass is present. LCMS: m/e 377 (M+H)⁺ LCMS retention time: 2.71 min. (Column: Phenomenex-Luna 50×2.0 mm 3u. Solvent A=90% Water: 10% Methanol: 0.1% TFA. Solvent B=10% Water: 90% Methanol: 0.1% TFA. Start % B=0. Final % B=100. Gradient Time=3 min. Flow Rate=0.8 mL/min.). ¹H NMR (500 MHz, CDCl₃) δ ppm 8.37 (s, 1H), 2.38 (s, 3H).

5-bromo-6-chloro-3-((4-fluorophenyl)ethynyl)pyridin-2-yl acetate 5-bromo-6-chloro-3-iodopyridin-2-yl acetate (14.5 g, 38.5 mmol) was dissolved in THF (50 mL) and cooled to 0° C. TEA (2.5 mL), Copper(I)Iodide (0.514 g, 2.70 mmol), and bistriphenylphosphine palladiumdichloride (0.270 g, 0.385 mmol) were added to the reaction mixture. The mixture was degassed and charged with N₂ (3×). Next, 1-ethynyl-4-fluorobenzene (5.55 g, 46.2 mmol) was added drop wise over the course of 1 h at 0° C. The reaction mixture was then allowed to slowly warm to rt and continue to stir for 18 h. LCMS and TLC show the reaction to be incomplete. An additional 2.5 mL of TEA was added. The mixture was then allowed to stir at rt over a long weekend (80 h). At this point, LCMS and TLC show no remaining starting material. The reaction mixture was concentrated to a dry solid. This solid was then taken up in DCM (50 mL) and washed with sat NH₄Cl. The aq layer was extracted with DCM (2×20 mL). The combined organic extracts were washed with water, brine, dried over Na₂SO₄, filtered and concentrated to >15 g of a brown solid. This solid was dissolved in DCM, adsorbed onto Celite and then flashed on silica gel eluting with a 10-100% DCM in hexanes gradient over 15 column volumes to give 5-bromo-6-chloro-3-((4-fluorophenyl)ethynyl)pyridin-2-yl acetate (11.7 g, 31.7 mmol, 82% yield) as a tan solid. LCMS: m/e 369 (M+H)⁺ LCMS retention time: 3.74 min. (Column: Phenomenex-Luna 50×2.0 mm 3u. Solvent A=90% Water: 10% Methanol: 0.1% TFA. Solvent B=10% Water: 90% Methanol: 0.1% TFA. Start % B=0. Final % B=100. Gradient Time=4 min. Flow Rate=0.8 mL/min.). ¹H NMR (500 MHz, CDCl₃) δ ppm 8.13 (s, 1H), 7.48 (dd, J=8.7 Hz, 2H), 7.09 (dd, J=8.7 Hz, 2H), 2.39 (s, 3H).

5-bromo-6-chloro-3-((4-fluorophenyl)ethynyl)pyridin-2-ol 5-bromo-6-chloro-3-((4-fluorophenyl)ethynyl)pyridin-2-yl acetate (5.5 g, 15 mmol) was suspended in MeOH (75 ml) and K₂CO₃ (4.12 g, 29.8 mmol) was added. The mixture was stirred at rt for 1 h. At this point, LCMS and TLC show no remaining SM. The mixture was then sparged with a balloon of CO for ten minutes and carried onto the following step, carbonylative coupling, without isolation.

methyl 5-bromo-6-chloro-2-(4-fluorophenyl)furo[2,3-b]pyridine-3-carboxylate

The entire reaction mixture from the previous step containing 5-bromo-6-chloro-3-((4-fluorophenyl)ethynyl)pyridin-2-ol (4.87 g, 14.9 mmol) was poured into a Parr Hydrogenation apparatus ("bomb") containing palladium(II) chloride (0.439 g, 2.48 mmol), sodium acetate (2.45 g, 29.8 mmol), copper(II) chloride dihydrate (7.63 g, 44.8 mmol). The reaction was charged with CO (350 PSI) minimizing the time the reaction is devoid of a blanket of CO. The reaction was stirred vigorously overnight at rt. LCMS shows both the desired product and the undesired C-3 H adduct in a minor amount. The reaction mixture was concentrated to dryness and then partitioned between 75 mL 1M HCl and EtOAc (75 mL). The layers were separated and the aqueous layer was extracted with EtOAc (3×75 mL). The combined organic extracts were washed with brine, dried over Na$_2$SO$_4$, filtered and concentrated to give 5.04 g of a 4:1 ratio of the desired methyl 5-bromo-6-chloro-2-(4-fluorophenyl)furo[2,3-b]pyridine-3-carboxylate to the undesired 5-bromo-6-chloro-2-(4-fluorophenyl)furo[2,3-b]pyridine. The mixture was carried on crude to the hydrolysis after which the acid and the C-3 H adduct can be separated by acid base extraction or silica gel chromatography. NOTE: The ratio of the desired product to the C-3 H adduct ranges from 2:1 to 9:1 depending on scale, with larger scale reactions giving less favorable results. LCMS: m/e 386 (M+H)$^+$ LCMS retention time: 3.97 min. (Column: Phenomenex-Luna 50×2.0 mm 3u. Solvent A=90% Water: 10% Methanol: 0.1% TFA. Solvent B=10% Water: 90% Methanol: 0.1% TFA. Start % B=0. Final % B=100. Gradient Time=4 min. Flow Rate=0.8 mL/min.).

5-bromo-6-chloro-2-(4-fluorophenyl)furo[2,3-b]pyridine-3-carboxylic acid

A 4:1 inseparable mixture of methyl 5-bromo-6-chloro-2-(4-fluorophenyl)furo[2,3-b]pyridine-3-carboxylate (2.38 g, 6.19 mmol) and 5-bromo-6-chloro-2-(4-fluorophenyl)furo[2,3-b]pyridine (0.265 g, 0.812 mmol) was taken up in a 1:1:1 mixture of MeOH (50 mL), THF (50 mL), 1M NaOH (50 mL). The entire mixture was heated in an oil bath to an internal temp of 65° C. This mixture was allowed to stir at this temp for 1 h. The solution was then concentrated to an aqueous mixture. This mixture was diluted with EtOAc and 1 M HCl (50 mL). The layers were separated and the aqueous layer was extracted with EtOAc (3×20 mL). The combined organic extracts were washed with water, brine, dried over Na$_2$SO$_4$, filtered and concentrated to give a white solid. This solid was adsorbed onto SiO$_2$ and flashed on silica gel eluting with a 0-10% MeOH in DCM solution containing 1% AcOH to give 5-bromo-6-chloro-2-(4-fluorophenyl)furo[2,3-b]pyridine-3-carboxylic acid (1.85 g, 4.99 mmol, 81% yield). LCMS: m/e 371 (M+H)$^+$ LCMS retention time: 3.30 min. (Column: Phenomenex-Luna 50×2.0 mm 3u. Solvent A=90% Water: 10% Methanol: 0.1% TFA. Solvent B=10% Water: 90% Methanol: 0.1% TFA. Start % B=0. Final % B=100. Gradient Time=4 min. Flow Rate=0.8 mL/min.).
$^1$H NMR (500 MHz, MeOD) δ ppm 8.66 (s, 1H), 8.21 (dd, J=9.2 Hz, 2H), 7.27 (dd, J=8.9 Hz, 2H).

5-bromo-6-chloro-2-(4-fluorophenyl)-N-methylfuro[2,3-b]pyridine-3-carboxamide

HATU (1.69 g, 4.45 mmol) was added to a stirring solution of 5-bromo-6-chloro-2-(4-fluorophenyl)furo[2,3-b]pyridine-3-carboxylic acid (1.1 g, 3.0 mmol), methylamine hydrochloride (1.00 g, 14.8 mmol), and DIEA (2.59 mL, 14.8 mmol) in a sealable tube in DMF (20 mL) at rt. The reaction tube was sealed and allowed to stir at rt for 2 hours. LCMS and TLC indicate complete conversion. The solution was then diluted with EtOAc (50 mL) and 1 M HCl (50 mL). The layers were separated and the aqueous layer was extracted with EtOAc (2×20 mL). The combined organic extracts were washed with water, brine, dried over Na$_2$SO$_4$, filtered and concentrated to give a tan solid. This solid was adsorbed onto SiO$_2$ and eluted on silica gel with a 0-5% MeOH in DCM gradient over 40 CV (very slow gradient) to give 5-bromo-6-chloro-2-(4-fluorophenyl)-N-methylfuro[2,3-b]pyridine-3-carboxamide (1.1 g, 2.7 mmol, 92% yield) as a white fluffy solid. LCMS: m/e 385 (M+H)$^+$ LCMS retention time: 3.04 min. (Column: Phenomenex-Luna 50×2.0 mm 3u. Solvent A=90% Water: 10% Methanol: 0.1% TFA. Solvent B=10% Water: 90% Methanol: 0.1% TFA. Start % B=0. Final % B=100. Gradient Time=4 min. Flow Rate=0.8 mL/min.). $^1$H NMR (500 MHz, CDCl$_3$) δ ppm 8.50 (s, 1H), 7.89 (dd, J=9.0 Hz, 2H), 7.23 (dd, J=8.7 Hz, 2H), 5.85 (br s, 1H), 3.00 (d, J=4.8 Hz, 3H).

tert-butyl 3-(6-chloro-2-(4-fluorophenyl)-3-(methylcarbamoyl)furo[2,3-b]pyridin-5-yl)benzoate A mixture of 5-bromo-6-chloro-2-(4-fluorophenyl)-N-methylfuro[2,3-b]pyridine-3-carboxamide (5.0 g, 13 mmol), (3-(tert-butoxycarbonyl)phenyl)boronic acid (2.75 g, 12.4 mmol). Pd(Ph$_3$P)$_4$ (2.26 g, 1.96 mmol) and cesium carbonate (8.49 g, 26.1 mmol) was degassed/charged with N$_2$ and diluted with water (22 ml)/DMF (220 ml). The resultant mixture was then degassed, charged with N$_2$, heated to an internal temperature of 65° C. and allowed to stir under N$_2$ atmosphere for 16 h. The reaction mixture was cooled to rt then diluted with EtOAc and sat. 1M HCl. The layers were separated and the aq layer was extracted with EtOAc (3×10 mL). The combined organic extracts were washed with water, brine, dried over Na$_2$SO$_4$ filtered and concentrated. The resultant solid was then flashed on SiO$_2$ eluting with a 0-100% EtOAc in hexanes gradient over 16 CV to give tert-butyl 3-(6-chloro-2-(4-fluorophenyl)-3-(methylcarbamoyl)furo[2,3-b]pyridin-5-yl)benzoate (5.2 g, 11 mmol, 83% yield) as a slightly yellow solid contaminated with the bis-coupled product di-tert-butyl 3,3'-(2-(4-fluorophenyl)-3-(methylcarbamoyl)furo[2,3-b]pyridine-5,6-diyl)dibenzoate. $^1$H NMR (500 MHz, CHLOROFORM-d) δ 8.18 (s, 1H), 8.08-8.02 (m, 2H), 7.95-7.89 (m, 2H), 7.63 (dt, J=7.6, 1.5 Hz, 1H), 7.52 (t, J=7.6 Hz, 1H), 7.24-7.18 (m, 2H), 6.03 (d, J=4.3 Hz, 1H), 2.99 (d, J=4.9 Hz, 3H), 1.62 (s, 9H).

tert-butyl 3-(2-(4-fluorophenyl)-3-(methylcarbamoyl)-6-(3,3,3-trifluoropropyl)furo[2,3-b]pyridin-5-yl)benzoate tert-butyl 3-(6-chloro-2-(4-fluorophenyl)-3-(methylcarbamoyl)furo[2,3-b]pyridin-5-yl)benzoate (1.50 g, 3.12 mmol), 3,3,3-trifluoropropane-1-trifluoroborate (1.59 g, 7.80 mmol), dicyclohexyl(2',6'-diisopropoxy-[1,1'-biphenyl]-2-yl)phosphine (582 mg, 1.25 mmol), Pd(OAc)$_2$ (140 mg, 0.624 mmol), cesium carbonate (3.05 g, 9.36 mmol) were combined, degassed, backfilled with N$_2$ then suspended in toluene (100 mL) and water (10 mL) at rt and then heated at 60° C. The reaction was allowed to stir 16 h. The reaction mixture was diluted with ethyl acetate and washed with sat NaHCO$_3$ followed by sat. NaCl (aq). The organic phase was concentrated and purified on silica gel (Biotage, EtOAc/hexanes gradient, fraction collection at λ=254 nm) to give the expected product t-butyl 3-(2-(4-fluorophenyl)-3-(methylcarbamoyl)-6-(3,3,3-trifluoropropyl)furo[2,3-b]pyridin-5-yl)benzoate (1.6 g, 2.95 mmol, 95% yield) consistent by LCMS and NMR. LC-MS retention time: 2.20 min; m/z (MH+): 543. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. $^1$H NMR (400 MHz, DMSO-d$_6$) δ 8.51-8.45 (m, 1H), 8.09-8.03

(m, 2H), 8.01-7.96 (m, 2H), 7.93 (t, J=1.5 Hz, 1H), 7.72-7.70 (m, 1H), 7.68-7.62 (m, 1H), 7.44-7.38 (m, 2H), 2.98 (dd, J=9.2, 6.4 Hz, 2H), 2.85-2.71 (m, 5H), 1.60-1.54 (m, 9H).

3-(2-(4-fluorophenyl)-3-(methylcarbamoyl)-6-(3,3,3-trifluoropropyl)furo[2,3-b]pyridin-5-yl)benzoic acid TFA (2.24 ml, 29.0 mmol) was added to a stirring solution of tert-butyl 3-(2-(4-fluorophenyl)-3-(methylcarbamoyl)-6-(3,3,3-trifluoropropyl)furo[2,3-b]pyridin-5-yl)benzoate (315 mg, 0.581 mmol) in dichloroethane (5.81 ml) at rt. The reaction was allowed to stir for 1 h at rt and then was concentrated to dryness azeotroping with toluene to give the expected product 3-(2-(4-fluorophenyl)-3-(methylcarbamoyl)-6-(3,3,3-trifluoropropyl)furo[2,3-b]pyridin-5-yl)benzoic acid (189 mg, 0.389 mmol, 67% yield) consistent by LCMS and NMR. LC-MS retention time: 2.89 min; m/z (MH+): 487. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode. $^1$H NMR (400 MHz, DMSO-$d_6$) δ 13.16 (br. s, 1H), 8.55-8.47 (m, 1H), 8.10-8.02 (m, 3H), 8.00-7.96 (m, 2H), 7.74 (d, J=7.8 Hz, 1H), 7.69-7.62 (m, 1H), 7.42 (t, J=8.9 Hz, 2H), 3.05-2.96 (m, 2H), 2.85-2.70 (m, 5H).

tert-butyl 5-(6-chloro-2-(4-fluorophenyl)-3-(methylcarbamoyl)furo[2,3-b]pyridin-5-yl)-2-methoxybenzoate Step 1: Preparation of 5-(6-chloro-2-(4-fluorophenyl)-3-(methylcarbamoyl)furo[2,3-b]pyridin-5-yl)-2-methoxybenzoic acid: A mixture of 5-borono-2-methoxybenzoic acid (562 mg, 2.87 mmol), Pd(Ph$_3$P)$_4$ (301 mg, 0.261 mmol) and cesium carbonate (1.27 g, 3.91 mmol) was degassed and diluted with water (3.1 ml) and DMF (31 ml). The mixture was degassed and heated to 65° C. under N$_2$. The reaction was allowed to stir at 65° C. for 16 h. The mixture was diluted with EtOAc and washed with 1M HCl, and saturated NaCl. The organic phase was dried over Na$_2$SO$_4$, filtered and concentrated. The residue was triturated with DCM to give the expected product 5-(6-chloro-2-(4-fluorophenyl)-3-(methylcarbamoyl)furo[2,3-b]pyridin-5-yl)-2-methoxybenzoic acid (890 mg, 1.96 mmol, 75% yield as a white solid. LC-MS retention time: 2.46 min; m/z (MH+): 455. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode. $^1$H NMR (400 MHz, DMSO-$d_6$) δ 12.82 (br. s., 1H), 8.58-8.50 (m, 1H), 8.14 (s, 1H), 8.10-8.02 (m, 2H), 7.79 (d, J=2.3 Hz, 1H), 7.69 (dd, J=8.5, 2.5 Hz, 1H), 7.47-7.38 (m, 2H), 7.28 (d, J=8.8 Hz, 1H), 3.90 (s, 3H), 2.83 (d, J=4.8 Hz, 3H).

Step 2: Preparation of title compound tert-butyl 5-(6-chloro-2-(4-fluorophenyl)-3-(methylcarbamoyl)furo[2,3-b]pyridin-5-yl)-2-methoxybenzoate:1,1-di-tert-butoxy-N,N-dimethylmethanamine (3.16 mL, 13.2 mmol) was added drop wise to a stirring suspension of 5-(6-chloro-2-(4-fluorophenyl)-3-(methylcarbamoyl)furo[2,3-b]pyridin-5-yl)-2-methoxybenzoic acid (1.0 g, 2.2 mmol) in DMF (20 mL) at 100° C. The mixture was allowed to stir at 100° C. overnight. The mixture was then concentrated to a oily residue and then purified on silica gel eluting with a 0-100% EtOAc in hexanes gradient over 15 CV to give tert-butyl 5-(6-chloro-2-(4-fluorophenyl)-3-(methylcarbamoyl)furo[2,3-b]pyridin-5-yl)-2-methoxybenzoate (450 mg, 0.88 mmol, 40% yield) as a brownish/yellow solid. LC-MS retention time: 1.93 min; m/z (M-tBu)$^+$: 455. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. $^1$H NMR (500 MHz, CHLOROFORM-d) δ 8.19 (s, 1H), 7.98-7.92 (m, 2H), 7.82 (d, J=2.5 Hz, 1H), 7.55 (dd, J=8.6, 2.4 Hz, 1H), 7.26-7.21 (m, 2H), 7.06 (d, J=8.7 Hz, 1H), 5.84 (br s, 1H), 3.97 (s, 3H), 3.03-2.95 (m, 3H), 1.61 (s, 9H).

5-(2-(4-fluorophenyl)-3-(methylcarbamoyl)-6-(3,3,3-trifluoropropyl)furo[2,3-b]pyridin-5-yl)-2-methoxybenzoic acid tert-butyl 5-(6-chloro-2-(4-fluorophenyl)-3-(methylcarbamoyl)furo[2,3-b]pyridin-5-yl)-2-methoxybenzoate (450 mg, 0.881 mmol), 3,3,3-trifluoropropane-1-trifluoroborate (449 mg, 2.20 mmol), dicyclohexyl(2',6'-diisopropoxy-[1,1'-biphenyl]-2-yl)phosphine (164 mg, 0.352 mmol), Pd(OAc)$_2$ (39.5 mg, 0.176 mmol), cesium carbonate (861 mg, 2.64 mmol) were degassed and backfilled with N$_2$ then dissolved in toluene (23 ml) and water (2.3 ml) at rt then heated at 70° C. The reaction was allowed to stir 16 h. The mixture was diluted with ethyl acetate and washed with sat NaHCO$_3$ aq, and sat NaCl aq. The organic phase was concentrated and was purified on silica gel (Biotage, EtOAc/hexanes gradient, fraction collection at λ=254 nm) to give tert-butyl 5-(2-(4-fluorophenyl)-3-(methylcarbamoyl)-6-(3,3,3-trifluoropropyl)furo[2,3-b]pyridin-5-yl)-2-methoxybenzoate consistent by LCMS. LC-MS retention time: 2.27 min; m/z (MH+): 573. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode. The solid obtained was taken up in 7 mL of DCM and was treated with 3 mL of TFA and the reaction was allowed to stir for 1 h at rt. The reaction was then concentrated and azeotroped with toluene and triturated with DCM to give 5424-fluorophenyl)-3-(methylcarbamoyl)-6-(3,3,3-trifluoropropyl)furo[2,3-b]pyridin-5-yl)-2-methoxybenzoic acid (335 mg, 0.649 mmol, 74% yield) consistent by LCMS and NMR. LC-MS retention time: 1.91 min; m/z (MH+): 517. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode. $^1$H NMR (400 MHz, DMSO-$d_6$) δ 12.70 (br. s, 1H), 8.51-8.42 (m, 1H), 8.06 (dd, J=9.0, 5.5 Hz, 2H), 7.92 (s, 1H), 7.68 (d, J=2.3 Hz, 1H), 7.59 (s, 1H), 7.41 (t, J=9.0 Hz, 2H), 7.27 (d, J=8.5 Hz, 1H), 3.90 (s, 3H), 3.02 (d, J=8.3 Hz, 2H), 2.82 (d, J=4.5 Hz, 3H), 2.80-2.66 (m, 2H).

5-(6-chloro-2-(4-fluorophenyl)-3-(methylcarbamoyl) furo[2,3-b]pyridin-5-yl)-2-fluorobenzoic acid A mixture of 5-bromo-6-chloro-2-(4-fluorophenyl)-N-methylfuro[2,3-b]pyridine-3-carboxamide (3.0 g, 7.8 mmol), 5-borono-2-fluorobenzoic acid (1.58 g, 8.60 mmol), Pd(Ph$_3$P)$_4$ (0.90 g, 0.78 mmol) and cesium carbonate (3.82 g, 11.7 mmol) was evacuated and charged with N$_2$ (3×) and then diluted with water (0.95 ml)/DMF (9.5 ml). The mixture was again evacuated and charged with N$_2$ (3×) and heated to 65° C. under N$_2$ atmosphere. The reaction was allowed to stir at 65° C. for 16 h. LCMS showed peak with the expected M+H. The mixture was diluted with EtOAc (30 mL) and washed with 1M HCl, and sat aq NaCl. The organic phase was dried over Na$_2$SO$_4$, filtered and concentrated to give solid which was triturated with DCM to give the expected product 5-(6-chloro-2-(4-fluorophenyl)-3-(methylcarbamoyl)furo[2,3-b]pyridin-5-yl)-2-fluorobenzoic acid (2.4 g, 5.4 mmol, 69% yield) consistent by LCMS and NMR. LC-MS retention time: 2.64 min; m/z (MH+): 443. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 2 min, and an analysis time of 4 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode. 1H NMR (400 MHz, DMSO-d6) δ 13.46 (br. s, 1H), 8.55 (d, J=4.8 Hz, 1H), 8.21 (s, 1H), 8.10-8.04 (m, 2H), 8.00 (dd, J=7.0, 2.5 Hz, 1H), 7.82 (ddd, J=8.5, 4.5, 2.5 Hz, 1H), 7.52-7.39 (m, 3H), 2.82 (d, J=4.8 Hz, 3H).

tert-butyl 5-(6-chloro-2-(4-fluorophenyl)-3-(methylcarbamoyl)furo[2,3-b]pyridin-5-yl)-2-fluorobenzoate 1,1-di-tert-butoxy-N,N-dimethylmethanamine (6.50 mL, 27.1 mmol) was added drop wise to a stirring suspension of 5-(6-chloro-2-(4-fluorophenyl)-3-(methylcarbamoyl)furo[2,3-b]pyridin-5-yl)-2-fluorobenzoic acid (2.0 g, 4.5 mmol) in DMF (10 mL) at 100° C. The reaction mixture was allowed to stir at this temp overnight. Finally, the reaction was concentrated to an orange residue. This semisolid was flashed on silica gel end eluted with 0-100% EtOAc in hexanes over 15 CV to give tert-butyl 5-(6-chloro-2-(4-fluorophenyl)-3-(methylcarbamoyl)furo[2,3-b]pyridin-5-yl)-2-fluorobenzoate (1.5 g, 3.0 mmol, 67% yield) as a yellow solid. LC-MS retention time: 2.14 min; m/z (MH+): 499. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. $^1$H NMR (500 MHz, CHLOROFORM-d) δ 8.18 (s, 1H), 8.01-7.87 (m, 3H), 7.59 (ddd, J=8.5, 4.5, 2.5 Hz, 1H), 7.28-7.18 (m, 3H), 5.96 (d, J=4.3 Hz, 1H), 2.99 (d, J=4.9 Hz, 3H), 1.62 (s, 9H).

2-fluoro-5-(2-(4-fluorophenyl)-3-(methylcarbamoyl)-6-(3,3,3-trifluoropropyl)furo[2,3-b]pyridin-5-yl) benzoic acid tert-butyl 5-(6-chloro-2-(4-fluorophenyl)-3-(methylcarbamoyl)furo[2,3-b]pyridin-5-yl)-2-fluorobenzoate (500 mg, 1.00 mmol), 3,3,3-trifluoropropane-1-trifluoroborate (511 mg, 2.51 mmol), dicyclohexyl(2',6'-diisopropoxy-[1,1'-biphenyl]-2-yl)phosphine (187 mg, 0.401 mmol), PdOAc$_2$ (45.0 mg, 0.200 mmol), cesium carbonate (980 mg, 3.01 mmol) were degassed and backfilled with N$_2$ then dissolved in toluene (23 ml) and water (2.3 ml) at rt then heated at 70° C. The reaction was allowed to stir 16 h. The mixture was diluted with ethyl acetate and washed with sat NaHCO$_3$ aq, and sat NaCl aq. The organic phase was concentrated and was purified on silica gel (Biotage, EtOAc/hexanes gradient, fraction collection at λ=254 nm) to give tert-butyl 2-fluoro-5-(2-(4-fluorophenyl)-3-(methylcarbamoyl)-6-(3,3,3-trifluoropropyl)furo[2,3-b]pyridin-5-yl)benzoate (469 mg, 0.837 mmol) consistent by LCMS. LC-MS retention time: 2.18 min; m/z (MH+): 561. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. This material was taken up in 8 mL of DCM and was treated with 3.5 mL of TFA and the reaction was allowed to stir for 1 h. The reaction was concentrated and azeotroped with toluene to give a solid which was triturated with DCM to give 2-fluoro-5-(2-(4-fluorophenyl)-3-(methylcarbamoyl)-6-(3,3,3-trifluoropropyl)furo[2,3-b]pyridin-5-yl)benzoic acid (395 mg, 0.783 mmol, 78% yield) consistent by LCMS and NMR. LC-MS retention time: 1.90 min; m/z (MH+): 505. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode. $^1$H NMR (400 MHz, DMSO-$d_6$) δ 13.42 (br. s, 1H), 8.52-8.45 (m, 1H), 8.06 (dd, J=9.0, 5.5 Hz, 2H), 7.98 (s, 1H), 7.93-7.88 (m, 1H), 7.77-7.70 (m, 1H), 7.52-7.37 (m, 3H), 2.99 (d, J=8.3 Hz, 2H), 2.82 (d, J=4.8 Hz, 3H), 2.80-2.69 (m, 2H).

2-(1,2,4-oxadiazol-3-yl)propan-2-amine hydrochloride

Step 1: Preparation of N-(2-cyanopropan-2-yl)-2-methylpropane-2-sulfinamide: 2-methylpropane-2-sulfinic chloride (1.28 g, 9.12 mmol) was added to a stirring solution of 2-amino-2-methylpropanenitrile hydrochloride (1.0 g, 8.3 mmol) in DCM (21 ml) and N-ethyl-N-isopropylpropan-2-amine (3.04 ml, 17.4 mmol) at rt. DMAP (10 mg, 0.083 mmol) was added and the reaction was allowed to stir 1 h. The mixture was then diluted with dichloromethane and washed with sat NH$_4$Cl aq, and sat NaCl aq. The organic phase was dried over Na$_2$SO$_4$, filtered and concentrated to give the expected product N-(2-cyanopropan-2-yl)-2-methylpropane-2-sulfinamide (1.45 g, 7.71 mmol, 93% yield) consistent by LCMS and NMR. LC-MS retention time: 2.15 min; m/z (MH+): 189. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode. $^1$H NMR (400 MHz, CHLOROFORM-d) δ 1.76 (s, 3H), 1.69 (s, 3H), 1.24 (s, 9H).

Step 2: Preparation of 2-(1,1-dimethylethylsulfinamido)-N'-hydroxy-2-methylpropanimidamide: Potassium carbonate (2.94 g, 21.2 mmol) was added to a stirring solution of N-(2-cyanopropan-2-yl)-2-methylpropane-2-sulfinamide (1.0 g, 5.3 mmol) and hydroxylamine hydrochloride (738 mg, 10.6 mmol) in EtOH (18 mL) at rt. The reaction was heated to 60° C. for 16 h. The reaction was then concentrated and the resulting residue was diluted with EtOAc and washed with water, and sat NaCl aq. The organic phase was dried over Na$_2$SO$_4$, filtered and concentrated azeotroping with toluene to give the expected product 2-(1,1-dimethylethylsulfinamido)-N'-hydroxy-2-methylpropanimidamide (1.0 g, 4.5 mmol, 85% yield) as a white solid consistent by LCMS and NMR. LC-MS retention time: 0.35 min; m/z (MH+): 222. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. $^1$H NMR (400 MHz, DMSO-$d_6$) δ 9.14 (s, 1H), 5.27 (s, 1H), 5.25 (s, 2H), 1.36 (d, J=5.0 Hz, 6H), 1.12 (s, 9H).

Step 3: Preparation of N-(2-(1,2,4-oxadiazol-3-yl)propan-2-yl)-2-methylpropane-2-sulfinamide: 2-(1,1-dimethylethylsulfinamido)-N'-hydroxy-2-methylpropanimidamide (1.0 g, 4.5 mmol) in triethoxymethane (7.5 ml, 45 mmol) was treated with AcOH (7.5 ml) at rt. The reaction was allowed to stir at rt for 16 h. The reaction was then concentrated to dryness azeotroping with toluene 3×. The resulting yellow oil was purified on silica gel (Biotage, EtOAc/hexanes gradient) to give the expected product N-(2-(1,2,4-oxadiazol-3-yl)propan-2-yl)-2-methylpropane-2-sulfinamide (750 mg, 3.24 mmol, 72% yield) consistent by LCMS and NMR. LC-MS retention time: 0.987 min; m/z (MH+): 232. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. $^1$H NMR (400 MHz, DMSO-$d_6$) δ 9.51 (s, 1H), 5.54 (s, 1H), 1.65 (s, 3H), 1.59 (s, 3H), 1.08 (s, 9H).

Step 4: Preparation of the titled compound: 2-(1,2,4-oxadiazol-3-yl)propan-2-amine hydrochloride: HCl (6 mL, 12 mmol) (2.0 M in Et$_2$O) was added to a stirring solution of N-(2-(1,2,4-oxadiazol-3-yl)propan-2-yl)-2-methylpropane-2-sulfinamide (750 mg, 3.24 mmol) in MeOH (6 mL) at rt. The reaction was allowed to stir for 1 h at rt. The reaction was then concentrated to dryness azeotroping with toluene 3× to give the expected product 2-(1,2,4-oxadiazol-3-yl)propan-2-amine hydrochloride (500 mg, 3.06 mmol, 94% yield) consistent NMR as a white solid. $^1$H NMR (400 MHz, DMSO-$d_6$) δ 9.78 (s, 1H), 8.96 (br. s., 3H), 1.67 (s, 6H).

2-(1,2,4-oxadiazol-3-yl)($^2$H$_6$)propan-2-amine hydrochloride

Step 1: Preparation of (R)—N-[1-cyano-1-($^2$H$_3$)methyl($^2$H$_3$)ethyl]-2-methylpropane-2-sulfinamide: Trimethylsilanecarbonitrile (10 ml, 78 mmol) was added to a stirring solution of (R)-2-methylpropane-2-sulfinamide (9.5 g, 78 mmol), Acetone-d6 (99.96% D) (6.3 ml, 78 mmol), titatium (IV) ethoxide (35.6 g, 156 mmol) in DCM (130 ml) along with activated 3 A mol sieves (cylinderial) (20 g) at rt in a 350 mL wide mouth pressure vessel. The vessel was sealed and the mixture was stirred at 40° C. for 16 h. The reaction was transferred to a 500 mL Erlenmeyer flask and while stirring was quenched with H$_2$O (10 mL) and Celite was added to mixture. A thick slurry formed which after 5 min of stirring became less viscous. This slurry was filtered through a trilayer pad of Celite/Na$_2$SO$_4$/Celite washing with DCM. The filtrate was concentrated, adsorbed onto Celite and was purified on silica gel (Biotage, EtOAc/hexanes gradient, TLC (75% EtOAc/Hex) product was visualized with permanganate stain) to give the expected product (8.8 g, 45.0 mmol, 58% yield) consistent by LCMS and NMR. LC-MS retention time: 1.09 min; m/z (MH+): 195. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode. $^1$H NMR (500 MHz, DMSO-$d_6$) δ 6.08 (s, 1H), 1.13 (s, 9H).

Step 2: Preparation of (Z)—N'-hydroxy-2-($^2$H$_3$)methyl-2-{[(R)-2-methylpropane-2-sulfinyl]amino}($^2$H$_3$)propimidamide: In a 500 mL RB flask potassium carbonate (24.9 g, 180 mmol) was added to a stirring solution of (R)—N-[1-cyano-1-($^2$H$_3$)methyl($^2$H$_3$)ethyl]-2-methylpropane-2-sulfinamide (8.8 g, 45 mmol) and hydroxylamine hydrochloride (6.3 g, 90 mmol) in EtOH (150 ml) at rt. The reaction was allowed to stir overnight 16 h at 60° C. under a balloon of N$_2$. The reaction was then allowed to cool to rt and was filtered through a pad of Celite washing with EtOAc to filter off most of the K$_2$CO$_3$. The filtrate was concentrated and taken up in EtOAc. Celite was then added to the mixture and it was filtered through another pad of Celite washing with EtOAc to filter off the rest of the K$_2$CO$_3$. The filtrate was concentrated azeotroping with toluene 2× to give the expected product (6.1 g, 27 mmol, 60% yield) as a white solid consistent by LCMS and NMR LC-MS retention time: 0.98 min; m/z (MH+): 228. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode. $^1$H NMR (500 MHz, DMSO-d$_6$) δ 9.14 (br. s, 1H), 5.34-5.17 (m, 3H), 1.12 (s, 9H).

Step 3: Preparation of (R)-2-methyl-N-[2-(1,2,4-oxadiazol-3-yl)($^2$H$_6$)propan-2-yl]propane-2-sulfinamide: (Z)—N'-hydroxy-2-($^2$H$_3$)methyl-2-{[(R)-2-methylpropane-2-sulfinyl]amino}($^2$H$_3$)propimidamide (6.1 g, 27 mmol) in triethoxymethane (40.2 ml, 241 mmol) was treated with AcOH (40 ml) at rt. The reaction was allowed to stir at rt for 16 h. The reaction was concentrated to dryness azeotroping with toluene 3×. The resulting yellow oil was absorbed onto Celite and was purified on silica gel (Biotage, EtOAc/hexanes gradient (TLC with 70% EtOAc/Hex, visualized with permangante stain), to give the expected product (5.1 g, 21 mmol, 80% yield) as a clear oil consistent by LCMS and NMR. LC-MS retention time: 1.13 min; m/z (MH+): 238. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% MeOH/90% H$_2$O/0.1% trifluoroacetic acid and solvent B was 10% H$_2$O/90% MeOH/0.1% trifluoroacetic acid. MS data was determined using a Micromass Platform for LC in electrospray mode. $^1$H NMR (500 MHz, DMSO-d$_6$). δ 9.52 (s, 1H), 5.55 (s, 1H), 1.08 (s, 9H) Step 4: Preparation of the titled compound: 2-(1,2,4-oxadiazol-3-yl)($^2$H$_6$)propan-2-amine hydrochloride HCl (42 ml, 84 mmol) (2.0 M in Et$_2$O) was added to a stirring solution of (R)-2-methyl-N-[2-(1,2,4-oxadiazol-3-yl)($^2$H$_6$)propan-2-yl]propane-2-sulfinamide (5.0 g, 21 mmol) in MeOH (42 ml) at rt. The reaction was allowed to stir for 1 h at rt. The reaction was then concentrated to dryness azeotroping with toluene 3× to give the expected product 2-(1,2,4-oxadiazol-3-yl)($^2$H$_6$)propan-2-amine hydrochloride (2.9 g, 17 mmol, 80% yield) consistent by NMR as a white solid. $^1$H NMR (500 MHz, DMSO-d$_6$) δ 9.79 (s, 1H), 8.89 (br. s., 3H).

2-[($^2$H)-1,2,4-oxadiazol-3-yl]($^2$H$_6$)propan-2-amine hydrochloride

Step 1: Preparation of (R)-2-methyl-N-{2-[($^2$H)-1,2,4-oxadiazol-3-yl]($^2$H$_6$)propan-2-yl}propane-2-sulfinamide: (Z)—N'-hydroxy-2-($^2$H$_3$)methyl-2-{[(R)-2-methylpropane-2-sulfinyl]amino}($^2$H$_3$)propimidamide (140 mg, 0.616 mmol) in AcOH (0.5 ml) was treated with [diethoxy($^2$H)methoxy]ethane (0.103 ml, 0.616 mmol) at rt. The reaction was allowed to stir at rt for 40 h. The reaction was concentrated to dryness azeotroping with toluene 2×. The resulting oil was purified on silica gel (Biotage, EtOAc/hexanes gradient (Rf ~0.2 in 70% EtOAc/Hex, visualized with permanganate stain), to give the expected product (64 mg, 0.27 mmol, 44% yield) consistent by LCMS and NMR. LC-MS retention time: 1.09 min; m/z (MH+): 239. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode. $^1$H NMR (500 MHz, DMSO-d$_6$) δ 5.54 (s, 1H), 1.08 (s, 9H)

Step 2: Preparation of the titled compound: 2-[($^2$H)-1,2,4-oxadiazol-3-yl]($^2$H$_6$)propan-2-amine hydrochloride HCl (0.5 ml, 1 mmol) (2.0 M in Et2O) was added to a stirring solution of (R)-2-methyl-N-{2-[($^2$H)-1,2,4-oxadiazol-3-yl]($^2$H$_6$)propan-2-yl}propane-2-sulfinamide (60 mg, 0.25 mmol) in MeOH (0.5 ml) at rt. The reaction was allowed to stir for 1 hr at rt. The reaction was then concentrated to dryness azeotroping with toluene 3× to give the expected product (41 mg, 0.24 mmol, 95% yield) as a white solid.

($^2$H$_3$)methyl 2-($^2$H$_3$)methoxy-5-(tetramethyl-1,3,2-dioxaborolan-2-yl)pyridine-3-carboxylate Step 1: Preparation of ($^2$H$_3$)methyl 5-bromo-2-chloropyridine-3-carboxylate: To a solution of 5-bromo-2-chloronicotinic acid (7.26 g, 30.7 mmol) in CD$_3$OD (50 mL) was added 1 mL of conc. H$_2$SO$_4$. The mixture was heated to 60° C. After 48 h at 60° C., the mixture was concentrated and then taken up in EtOAc and water. The layers were separated and the aq layer was extracted with EtOAc (2×30 mL). The combined organic extracts were washed with water, brine, dried over Na$_2$SO$_4$, filtered and concentrated to give approximately 7.5 grams of crude desired product. This material was flashed on silica gel eluting with a 0-50% EtOAc in hexanes gradient to give the expected product (7.0 g, 28 mmol, 90% yield) consistent by LCMS and NMR. LC-MS retention time: 1.44 min; m/z (MH+): 253, 255. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode. $^1$H NMR (500 MHz, CHLOROFORM-d) δ 8.58 (d, J=2.5 Hz, 1H), 8.30 (d, J=2.5 Hz, 1H).

Step 2: Preparation of ($^2$H$_3$)methyl 5-bromo-2-($^2$H$_3$)methoxypyridine-3-carboxylate. Sodium (3.4 g, 150 mmol) was dissolved in Methanol-d4 (30 mL) in a 25° C. water bath. Next, to the d3-sodium methoxide solution was added methyl ($^2$H$_3$)methyl 5-bromo-2-chloropyridine-3-carboxylate (10 g, 40 mmol) as a solid at rt. The mixture was allowed to stir at room temperature for several hours resulting in a heavy white ppt. The mixture was quenched with the addition of sat NH$_4$Cl aq and then concentrated to an aq mixture. The mixture was diluted with EtOAc (35 mL) and 1 M HCl (50 mL). The layers were separated and the aq layer was extracted with EtOAc (30 mL). The combined organic extracts were washed with water, brine, dried over Na$_2$SO$_4$, filtered and concentrated to give the expected product (7.6 g, 30 mmol, 76% yield) as a white solid. LC-MS retention time: 1.47 min; m/z (MH+): 252, 254. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode.

$^1$H NMR (500 MHz, CHLOROFORM-d) δ 8.34 (d, J=2.5 Hz, 1H), 8.25 (d, J=2.5 Hz, 1H).

Step 3: Preparation of the titled compound: ($^2$H$_3$)methyl 2-($^2$H$_3$)methoxy-5-(tetramethyl-1,3,2-dioxaborolan-2-yl) pyridine-3-carboxylate ($^2$H$_3$)methyl 5-bromo-2-($^2$H$_3$)methoxypyridine-3-carboxylate (3.85 g, 15.3 mmol), BIS(PINACOLATO)DIBORON (7.76 g, 30.5 mmol), PdC12(dppf)-CH$_2$Cl$_2$ adduct (0.624 g, 0.764 mmol), and potassium acetate (3.75 g, 38.2 mmol) were combined, degassed, backfilled with N$_2$ and taken up in Dioxane (153 ml) at rt. The reaction was allowed to stir at 80° C. for 16 h. LCMS showed a major peak with M+H of 218 however TLC suggests boronic ester. The mixture was concentrated and adsorbed onto Celite and was purified on silica gel (Biotage, EtOAc/hexanes gradient, fraction collection at λ=254 nm) to give the expected boronic ester (4.46 g, 14.9 mmol, 98% yield) as a white solid. NMR is consistent with the boronic ester. $^1$H NMR (500 MHz, DMSO-d$_6$) δ 8.55 (d, J=1.9 Hz, 1H), 8.30 (d, J=2.0 Hz, 1H), 1.30 (s, 12H).

LC-MS retention time: 0.899 min; m/z (observed boronic acid M+H): 218. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode.

5-[2-(4-fluorophenyl)-3-(methylcarbamoyl)-6-(3,3,3-trifluoropropyl)furo[2,3-b]pyridin-5-yl]-2-($^2$H$_3$) methoxypyridine-3-carboxylic acid Step 1: Preparation of ($^2$H$_3$)methyl 5-[6-chloro-2-(4-fluorophenyl)-3-(methylcarbamoyl)furo[2,3-b]pyridin-5-yl]-2-($^2$H$_3$)methoxypyridine-3-carboxylate: A dry mixture of 5-bromo-6-chloro-2-(4-fluorophenyl)-N-methylfuro[2,3-b] pyridine-3-carboxamide (5.7 g, 15 mmol), ($^2$H$_3$)methyl 2-($^2$H$_3$)methoxy-5-(tetramethyl-1,3,2-dioxaborolan-2-yl) pyridine-3-carboxylate (4.5 g, 15 mmol), PdCl$_2$(dppf) (1.1 g, 1.5 mmol) and cesium carbonate (7.3 g, 22 mmol) was degassed and diluted DMF (180 ml)/Water (18 ml). The mixture was degassed and heated to 55° C. under N$_2$. The reaction was allowed to stir at 55° C. for 6 h. LCMS showed a peak with the expected M+H of 476. The reaction was concentrated to dryness and absorbed onto Celite and was purified on silica gel (Biotage, EtOAc/DCM gradient, fraction collection at λ=254 nm) to give the expected product (3.85 g, 8.09 mmol, 54% yield) consistent by LCMS and NMR. LC-MS retention time: 1.62 min; m/z (MH+): 476. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% MeOH/90% H$_2$O/0.1% trifluoroacetic acid and solvent B was 10% H$_2$O/90% MeOH/0.1% trifluoroacetic acid. MS data was determined using a Micromass Platform for LC in electrospray mode. $^1$H NMR (500 MHz, DMSO-d$_6$) δ 8.59-8.50 (m, 2H), 8.32-8.26 (m, 2H), 8.06 (dd, J=8.7, 5.4 Hz, 2H), 7.43 (t, J=8.8 Hz, 2H), 2.83 (d, J=4.4 Hz, 3H).

Step 2: Preparation of ($^2$H$_3$)methyl 5-[2-(4-fluorophenyl)-3-(methylcarbamoyl)-6-(3,3,3-trifluoropropyl)furo[2,3-b] pyridin-5-yl]-2-($^2$H$_3$)methoxypyridine-3-carboxylate. ($^2$H$_3$) methyl 5-[6-chloro-2-(4-fluorophenyl)-3-(methylcarbamoyl)furo[2,3-b]pyridin-5-yl]-2-($^2$H$_3$) methoxypyridine-3-carboxylate (3.45 g, 7.25 mmol), 3,3,3-trifluoropropane-1-trifluoroborate (3.70 g, 18.1 mmol), dicyclohexyl(2',6'-diisopropoxy-[1,1'-biphenyl]-2-yl)phosphine (1.35 g, 2.90 mmol), PdOAc$_2$ (0.326 g, 1.45 mmol), and cesium carbonate (7.09 g, 21.8 mmol) were combined, degassed and backfilled with N$_2$ then taken up in toluene (250 ml) and water (25 ml) at rt then heated at 80° C. The reaction was allowed to stir at this temp for 16 h overnight. LCMS showed complete conversion to peak with M+H of 538. The reaction was concentrated to dryness and absorbed onto Celite and was purified on silica gel (Biotage, EtOAc/DCM gradient, fraction collection at λ=254 nm) to give the expected product ($^2$H$_3$)methyl 5-[2-(4-fluorophenyl)-3-(methylcarbamoyl)-6-(3,3,3-trifluoropropyl)furo[2,3-b]pyridin-5-yl]-2-($^2$H$_3$)methoxypyridine-3-carboxylate (2.99 g, 5.56 mmol, 77% yield) consistent by LCMS and NMR. LC-MS retention time: 1.69 min; m/z (MH+): 538. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% MeOH/90% H$_2$O/0.1% trifluoroacetic acid and solvent B was 10% H$_2$O/90% MeOH/0.1% trifluoroacetic acid. MS data was determined using a Micromass Platform for LC in electrospray mode. $^1$H NMR (500 MHz, DMSO-d$_6$) δ 8.51-8.46 (m, 2H), 8.21 (d, J=2.4 Hz, 1H), 8.07 (dd, J=9.0, 5.4 Hz, 2H), 8.03 (s, 1H), 7.42 (t, J=8.9 Hz, 2H), 3.06-2.98 (m, 2H), 2.86-2.71 (m, 5H).

Step 3: Preparion of the titled intermediate: 5-[2-(4-fluorophenyl)-3-(methylcarbamoyl)-6-(3,3,3-trifluoropropyl)

furo[2,3-b]pyridin-5-yl]-2-($^2$H$_3$)methoxypyridine-3-carboxylic acid. ($^2$H$_3$)methyl 5-[2-(4-fluorophenyl)-3-(methylcarbamoyl)-6-(3,3,3-trifluoropropyl)furo[2,3-b]pyridin-5-yl]-2-($^2$H$_3$)methoxypyridine-3-carboxylate (2.9 g, 5.4 mmol) was dissolved in THF (28 mL) and MeOH (28 mL). 1M aq NaOH (27 mL, 27 mmol) was added at rt. The reaction was stirred at 60° C. for 1 h. The mixture was diluted with EtOAc and washed with 1M HCl, and sat NaCl. The organic phase was concentrated and azeotroped with toluene 3× to give 5-[2-(4-fluorophenyl)-3-(methylcarbamoyl)-6-(3,3,3-trifluoropropyl)furo[2,3-b]pyridin-5-yl]-2-($^2$H$_3$)methoxypyridine-3-carboxylic acid (2.8 g, 5.3 mmol, 98% yield) consistent by LCMS and NMR. LC-MS retention time: 1.59 min; m/z (MH+): 521. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% MeOH/90% H$_2$O/0.1% trifluoroacetic acid and solvent B was 10% H$_2$O/90% MeOH/0.1% trifluoroacetic acid. MS data was determined using a Micromass Platform for LC in electrospray mode. $^1$H NMR (500 MHz, DMSO-d$_6$) δ 13.13 (br. s, 1H), 8.53-8.46 (m, 1H), 8.45 (d, J=2.5 Hz, 1H), 8.19 (d, J=2.5 Hz, 1H), 8.10-8.04 (m, 2H), 8.02 (s, 1H), 7.46-7.37 (m, 2H), 3.07-2.99 (m, 2H), 2.85-2.72 (m, 5H).

5-[2-(4-fluorophenyl)-3-(methylcarbamoyl)-6-[(2,2,2-trifluoroethyl)amino]furo[2,3-b]pyridin-5-yl]-2-($^2$H$_3$)methoxypyridine-3-carboxylic acid Sodium 2-methylbutan-2-olate (116 mg, 1.05 mmol), 54244-fluorophenyl)-3-(methylcarbamoyl)-6-[(chloro)furo[2,3-b]pyridin-5-yl]-2-($^2$H$_3$)methoxypyridine-3-carboxylic acid (100 mg, 0.210 mmol), 2,2,2-trifluoroethanamine (104 mg, 1.05 mmol), Chloro[2-(dicyclohexylphosphino)-3,6-dimethoxy-2'-4'-6'-tri-1-propyl-1,1'-biphenyl][2-(2-aminoethyl)phenyl]palladium(II) (17 mg, 0.021 mmol) was combined, degassed, and taken up in dioxane (4 ml) at rt and then was heated to 90° C. for 2 hrs. LCMS showed major peak with M+H of 522. The reaction was concentrated and was purified by preparative reverse phase HPLC on a C18 column using a suitably buffered H$_2$O/CH$_3$CN gradient, and concentrated to give the expected product (40 mg, 0.077 mmol, 37% yield) consistent by LCMS and NMR. LC-MS retention time: 1.58 min; m/z (observed boronic acid M+H): 522. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode. $^1$H NMR (500 MHz, DMSO-d$_6$) δ 13.06 (br. s, 1H), 8.36 (d, J=2.5 Hz, 1H), 8.35-8.30 (m, 1H), 8.12 (d, J=2.5 Hz, 1H), 7.98 (dd, J=9.0, 5.4 Hz, 2H), 7.71 (s, 1H), 7.34 (t, J=8.9 Hz, 2H), 6.92-6.84 (m, 1H), 4.21-4.09 (m, 2H), 2.80 (d, J=4.6 Hz, 3H).

5-[2-(4-fluorophenyl)-3-(methylcarbamoyl)-6-(3,3,3-trifluoropropyl)furo[2,3-b]pyridin-5-yl]-2-methoxypyridine-3-carboxylic acid Step 1: Preparation of methyl 5-[6-chloro-2-(4-fluorophenyl)-3-(methylcarbamoyl)furo[2,3-b]pyridin-5-yl]-2-methoxypyridine-3-carboxylate: A mixture of 5-bromo-6-chloro-2-(4-fluorophenyl)-N-methylfuro[2,3-b]pyridine-3-carboxamide (1.15 g, 2.99 mmol), commercially available methyl 2-methoxy-5-(4,4,5,5-tetramethyl-1,3,2-dioxaborolan-2-yl)nicotinate (1.05 g, 3.58 mmol), Pd(Ph$_3$P)$_4$ (0.517 g, 0.448 mmol) and cesium carbonate (1.95 g, 5.97 mmol) was degassed/charged with N$_2$ and diluted with Water (0.5 ml)/DMF (5 mL). The resultant mixture was then degassed, charged with N$_2$, and heated in a 65° C. oil bath and allowed to stir under N$_2$ atmosphere for 4 h. LCMS shows desired product as well as some SM. The reaction was halted by cooling to rt and, the reaction mixture was diluted with EtOAc and sat. 1M HCl. The layers were separated and the aq layer was extracted with EtOAc (3×10 mL). The combined organic extracts were washed with water, brine, dried over Na$_2$SO$_4$ filtered and concentrated. The resultant solid was then flashed on silica gel eluting with a 0-100% EtOAc in hexanes mixture over 12 CV and then held at 100% EtOAc for 8 CV to give methyl 5-(6-chloro-2-(4-fluorophenyl)-3-(methylcarbamoyl)furo[2,3-b]pyridin-5-yl)-2-methoxynicotinate (630 mg, 1.31 mmol, 45% yield) as a tan solid. LC-MS retention time: 1.69 min; m/z (observed boronic acid M+H): 470. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode. $^1$H NMR (500 MHz, DMSO-d$_6$) δ 8.43 (d, J=2.5 Hz, 1H), 8.29 (d, J=2.5 Hz, 1H), 8.22 (s, 1H), 7.93 (dd, J=8.9, 5.1 Hz, 2H), 7.26-7.20 (m, 2H), 5.91 (br. s., 1H), 4.13 (s, 3H), 3.94 (s, 3H), 2.99 (d, J=5.0 Hz, 3H).

Step 2: Preparation of methyl 5-[2-(4-fluorophenyl)-3-(methylcarbamoyl)-6-(3,3,3-trifluoropropyl)furo[2,3-b]pyridin-5-yl]-2-methoxypyridine-3-carboxylate. Methyl 5-(6-chloro-2-(4-fluorophenyl)-3-(methylcarbamoyl)furo[2,3-b]pyridin-5-yl)-2-methoxynicotinate (600 mg, 1.28 mmol), 3,3,3-trifluoropropane-1-trifluoroborate (651 mg, 3.19 mmol), dicyclohexyl(2',6'-diisopropoxy-[1,1'-biphenyl]-2-yl)phosphine (238 mg, 0.511 mmol), PdOAc$_2$ (57.3 mg, 0.255 mmol), cesium carbonate (1250 mg, 3.83 mmol) were degassed and backfilled with N$_2$ then dissolved in toluene (2 mL) and water (0.2 mL) at rt then heated at 80° C. The reaction was allowed to stir 16 h. LCMS indicated a major peak with the expected M+H. The reaction mixture was diluted with EtOAc and washed with 1M HCl, and sat NaCl. The organic layer was dried over Na$_2$SO$_4$, filtered and concentrted to give a yellow solid. This solid was flashed on silica gel (Biotage) eluting with a 0-100% EtOAc in hexanes gradient over 15 CV to give methyl 5-(2-(4-fluorophenyl)-3-(methylcarbamoyl)-6-(3,3,3-trifluoropropyl)furo[2,3-b]pyridin-5-yl)-2-methoxynicotinate (0.638 g, 1.20 mmol, 94% yield) as a white solid. LC-MS retention time: 2:12 min; m/z (MH+): 532. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H$_2$O/10 mM ammonium acetate and solvent B was 5% H$_2$O/95% MeOH/

10 mM ammonium acetate. MS data was determined using a Micromass Platform for LC in electrospray mode. $^1$H NMR (500 MHz, DMSO-d$_6$) δ 8.51-8.46 (m, 2H), 8.24-8.19 (m, 1H), 8.09-8.04 (m, 2H), 8.04-8.01 (m, 1H), 7.45-7.37 (m, 2H), 4.01 (s, 3H), 3.84 (s, 3H), 3.05-3.00 (m, 2H), 2.85-2.74 (m, 5H).

Step 3: Preparation of the titled compound: 5-[2-(4-fluorophenyl)-3-(methylcarbamoyl)-6-(3,3,3-trifluoropropyl)furo[2,3-b]pyridin-5-yl]-2-methoxypyridine-3-carboxylic acid. NaOH (2.97 mL, 2.97 mmol) (1M aq) was added to a stirring solution of methyl 5-(2-(4-fluorophenyl)-3-(methylcarbamoyl)-6-(3,3,3-trifluoropropyl)furo[2,3-b]pyridin-5-yl)-2-methoxynicotinate (158 mg, 0.297 mmol) in MeOH (3 mL)/THF (3 mL) at 60° C. The reaction was allowed to stir for 1 h. Then the mixture was diluted with EtOAc and washed with 1M HCl. The organic phase was concentrated azeotroping with toluene to give the expected product 5-(2-(4-fluorophenyl)-3-(methylcarbamoyl)-6-(3,3,3-trifluoropropyl)furo[2,3-b]pyridin-5-yl)-2-methoxynicotinic acid (157 mg, 0.303 mmol) consistent by LCMS. LC-MS retention time: 1.70 min; m/z (MH+): 518. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode. $^1$H NMR (500 MHz, DMSO-d$_6$) δ 13.16 (br. s., 1H), 8.49 (d, J=4.6 Hz, 1H), 8.45 (d, J=2.5 Hz, 1H), 8.19 (d, J=2.5 Hz, 1H), 8.10-8.04 (m, 2H), 8.02 (s, 1H), 7.45-7.38 (m, 2H), 4.00 (s, 3H), 3.03 (dd, J=9.0, 6.6 Hz, 2H), 2.85-2.81 (m, 3H), 2.81-2.72 (m, 2H).

5-[2-(4-fluorophenyl)-3-(methylcarbamoyl)-6-[(2,2,2-trifluoroethyl)amino]furo[2,3-b]pyridin-5-yl]-2-methoxypyridine-3-carboxylic acid Sodium 2-methylbutan-2-olate (0.281 g, 2.55 mmol) was added to a stirring solution of methyl 5-(6-chloro-2-(4-fluorophenyl)-3-(methylcarbamoyl)furo[2,3-b]pyridin-5-yl)-2-methoxynicotinate (0.120 g, 0.255 mmol), 2,2,2-trifluoroethanamine (0.253 g, 2.55 mmol), Chloro[2-(dicyclohexylphosphino)-3,6-dimethoxy-2'-4'-6'-tri-1-propyl-1,1'-biphenyl][2-(2-aminoethyl)phenyl]palladium (II) (0.020 g, 0.026 mmol), in dioxane (2.55 ml) at 100° C. Immediately, the reaction mixture turned to a dark amber color. LCMS after 1 h shows complete conversion to the desired coupled product with simultaneous deprotection of the tButyl ester. The reaction mixture was cooled to rt and concentrated to a dry solid. The resultant solid was then taken up in EtOAc and diluted with 1 M HCl. The layers were separated and the aq layer was extracted with EtOAc (2×15 mL). The layers were washed with water, brine, dried over Na$_2$SO$_4$, filtered and concentrated to give a yellow solid. This solid was then triturated with DCM (25 mL) for 3 h. The solids were filtered to give the desired 5-(2-(4-fluorophenyl)-3-(methylcarbamoyl)-6-((2,2,2-trifluoroethyl)amino)furo[2,3-b]pyridin-5-yl)-2-methoxynicotinic acid (110 mg, 0.21 mmol, 83% yield) as a yellow solid. LC-MS retention time: 1.68 min; m/z (observed boronic acid M+H): 519. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode. $^1$H NMR (500 MHz, METHANOL-d$_4$) δ 8.38 (d, J=2.5 Hz, 1H), 8.29 (d, J=2.5 Hz, 1H), 7.91 (dd, J=8.2, 6.1 Hz, 3H), 7.69 (s, 1H), 7.23-7.19 (m, 3H), 4.18 (d, J=9.3 Hz, 2H), 4.07 (s, 3H), 2.91 (s, 3H).

5-[2-(4-fluorophenyl)-3-(methylcarbamoyl)-6-(2,2,2-trifluoroethoxy)furo[2,3-b]pyridin-5-yl]-2-($^2$H$_3$)methoxypyridine-3-carboxylic acid Step 1: Preparation of 2,2,2-trifluoroethyl 5-[2-(4-fluorophenyl)-3-(methylcarbamoyl)-6-(2,2,2-trifluoroethoxy)furo[2,3-b]pyridin-5-yl]-2-($^2$H$_3$)methoxypyridine-3-carboxylate: ($^2$H$_3$)methyl 5-[6-chloro-2-(4-fluorophenyl)-3-(methylcarbamoyl)furo[2,3-b]pyridin-5-yl]-2-($^2$H$_3$) methoxypyridine-3-carboxylate (125 mg, 0.263 mmol), dicyclohexyl({3,6-dimethoxy-2-[2,4,6-tris(propan-2-yl)phenyl]phenyl})phosphane[2-(2-aminophenyl)phenyl]palladio methanesulfonate (24 mg, 0.026 mmol), KOH (118 mg, 2.10 mmol) were combined in Dioxane (4.8 ml) and Water (0.48 ml). The reaction was heated to 100° C. for 2 h. The reaction was then diluted with EtOAc and washed with 1M HCl. The organic phase was concentrated and azeotroped with toluene 2× to give the expected alcohol product. The crude material was taken up in Cs$_2$CO$_3$ (148 mg, 0.454 mmol) in DMF (2.3 ml) and was treated with 2,2,2-trifluoroethyl trifluoromethanesulfonate (393 µl, 2.72 mmol) at rt. The reaction was allowed to stir overnight 16 h. The reaction was then concentrated and absorbed onto Celite and was purified on silica gel (Biotage, EtOAC/DCM gradient, fraction collection at λ=254 nm) to give the expected product (78 mg, 0.130 mmol) consistent by LCMS. LC-MS retention time: 2.0 min; m/z (M+H): 605. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode.

Step 2: Preparation of the titled compound: 5-[2-(4-fluorophenyl)-3-(methylcarbamoyl)-6-(2,2,2-trifluoroethoxy)furo[2,3-b]pyridin-5-yl]-2-($^2$H$_3$)methoxypyridine-3-carboxylic acid. 1M aq NaOH (1.3 ml, 1.3 mmol) was added to a stirring solution of 2,2,2-trifluoroethyl 5-[2-(4-fluorophenyl)-3-(methylcarbamoyl)-6-(2,2,2-trifluoroethoxy)furo[2,3-b]pyridin-5-yl]-2-($^2$H$_3$)methoxypyridine-3-carboxylate (78 mg, 0.13 mmol) in THF (0.65 ml) and MeOH (0.65 ml) at rt. The reaction was heated to 60° C. for 1 h. LCMS showed a peak with the expected M+H. The mixture was diluted with EtOAc and washed with 1M HCl, and sat NaCl. The organic phase was concentrated azeotroping with toluene to give 5-[2-(4-fluorophenyl)-3-(methylcarbamoyl)-6-(2,2,2-trifluoroethoxy)furo[2,3-b]pyridin-5-yl]-2-($^2$H$_3$)methoxypyridine-3-carboxylic acid (65 mg, 0.12 mmol, 96% yield) consistent by LCMS and NMR. LC-MS retention time: 1.69 min;

m/z (M+H): 523. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% $H_2O$/0.1% trifluoroacetic acid and solvent B was 10% $H_2O$/90% acetonitrile/0.1% trifluoroacetic acid. MS data was determined using a Micromass Platform for LC in electrospray mode. $^1$H NMR (500 MHz, DMSO-$d_6$) δ 13.08 (br. s., 1H), 8.59 (d, J=2.5 Hz, 1H), 8.37 (d, J=2.5 Hz, 1H), 8.24 (s, 1H), 8.05-8.01 (m, 2H), 7.41-7.37 (m, 2H), 5.13 (q, J=8.9 Hz, 2H), 2.85 (d, J=4.6 Hz, 3H).

2-[($^2$H)-1,2,4-oxadiazol-3-yl]propan-2-amine hydrochloride

Step 1: Preparation of 2-methyl-N-{2-[($^2$H)-1,2,4-oxadiazol-3-yl]propan-2-yl}propane-2-sulfinamide: (Z)-2-(1,1-dimethylethylsulfinamido)-N'-hydroxy-2-methylpropanimidamide (140 mg, 0.633 mmol) in AcOH (4 ml) was treated with [diethoxy($^2$H)methoxy]ethane (0.106 ml, 0.633 mmol) at rt. The reaction was allowed to stir at rt for 16 h. LCMS showed a major peak with the expected M+H. The reaction was concentrated to dryness azeotroping with toluene 3×. The resulting oil was purified on silica gel (Biotage, EtOAc/hexanes gradient (Rf ~0.2 in 70% EtOAc/Hex, visualized with permanganate stain), to give the expected product (27 mg, 0.12 mmol, 18% yield) consistent by LCMS. LC-MS retention time: 1.47 min; m/z (MH+): 233. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode. Step 2: Preparation of the titled compound: 2-[($^2$H)-1,2,4-oxadiazol-3-yl]propan-2-amine hydrochloride HCl (1.0 mL, 1.9 mmol) (2 M in $Et_2O$) was added to a stirring solution of 2-methyl-N-{2-[($^2$H)-1,2,4-oxadiazol-3-yl]propan-2-yl}propane-2-sulfinamide (27 mg, 0.12 mmol) in MeOH (1 mL) at rt. The reaction was allowed to stir for 2 h and then concentrated azeotroping with toluene to give the expected product (15 mg, 0.091 mmol, 78% yield) consistent by NMR. $^1$H NMR (400 MHz, METHANOL-$d_4$) δ 1.77 (s, 6H).

1-cyclopropyl-1-(1,2,4-oxadiazol-3-yl)ethan-1-amine hydrochloride

Step 1: Preparation of (R)—N-[(1E/Z)-1-cyclopropylethylidene]-2-methylpropane-2-sulfinamide: (R)-2-methylpropane-2-sulfinamide (6.05 g, 49.9 mmol) and titanium (IV) ethoxide (22 g, 95 mmol) were added sequentially to a solution of 1-cyclopropylethanone (4.71 ml, 47.6 mmol) in THF (95 ml) at rt in a pressure vessel. The mixture was stirred at 55° C. for 16 h. The reaction was diluted with water (ppt formed) followed by EtOAc. Celite was added and the mixture was filtered through a pad of Celite. The organic phase was washed with $H_2O$, and sat aq NaCl. The organic phase was dried over $Na_2SO_4$, filtered and concentrated. The residue was absorbed onto Celite was purified on silica gel (Biotage, EtOAc/hexanes gradient) to give the expected product (5.89 g, 31.4 mmol, 66% yield) consistent by LCMS and NMR. LC-MS retention time: 1.56 min; m/z (MH+): 188. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode. $^1$H NMR (500 MHz, DMSO-$d_6$) δ 2.28 (s, 3H), 1.83-1.77 (m, 1H), 1.09 (s, 9H), 0.96-0.89 (m, 4H).

Step 2: Preparation of (R)—N-(1-cyano-1-cyclopropylethyl)-2-methylpropane-2-sulfinamide. Titanium (IV) ethoxide (7.06 g, 31.0 mmol) was added to a stirring solution of (R)—N-(1-cyclopropylethylidene)-2-methylpropane-2-sulfinamide (5.8 g, 31 mmol) and trimethylsilyl cyanide (8.30 ml, 61.9 mmol) in DCM (155 ml) at rt. The reaction was allowed to stir for 16 h. The reaction was quenched with $H_2O$ and Celite was added to mixture which was subsequently filtered through a trilayer pad of Celite/$Na_2SO_4$/Celite washing with DCM. The filtrate which was concentrated, absorbed onto Celite and was purified on silica gel (Biotage, EtOAc/hexanes gradient, TLC (75% EA/Hex) visualized with permanganate stain) to give 300 mg, 1.40 mmol of the faster eluting diastereomer (10:1) as well as 366 mg, 1.71 mmol of the slower eluting diastereomer (1:10) both consistent by NMR. Additionally, 2.7 g, 14 mmol of starting material was recovered. First eluting diastereomer: $^1$H NMR (500 MHz, DMSO-$d_6$) δ 6.10 (s, 1H), 1.59 (s, 3H), 1.14 (s, 9H), 0.71-0.56 (m, 3H), 0.43-0.37 (m, 1H); Second eluting diastereomer: $^1$H NMR (500 MHz, DMSO-$d_6$) δ 6.07 (s, 1H), 1.56 (s, 3H), 1.14 (s, 9H), 0.67-0.57 (m, 3H), 0.50-0.45 (m, 1H).

Step 3: Preparation of (Z)-2-cyclopropyl-N'-hydroxy-2-{[(R)-2-methylpropane-2-sulfinyl]amino}propimidamide. Potassium carbonate (774 mg, 5.60 mmol) was added to a stirring solution of the first eluting diastereomer (R)—N-(1-cyano-1-cyclopropylethyl)-2-methylpropane-2-sulfinamide (300 mg, 1.40 mmol) and hydroxylamine hydrochloride (195 mg, 2.80 mmol) in EtOH (4.7 ml) at rt. The reaction was allowed to stir 16 h overnight at 50° C. The reaction was allowed to cool to rt and Celite was then added to the reaction mixture and it was filtered through a pad of Celite washing with EtOAc. The filtrate was concentrated to give the expected product (321 mg, 1.30 mmol, 93% yield) consistent by LCMS. LC-MS retention time: 1.09 min; m/z M+H: 248. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% $H_2O$/0.1% trifluoroacetic acid and solvent B was 10% $H_2O$/90% acetonitrile/0.1% trifluoroacetic acid. MS data was determined using a Micromass Platform for LC in electrospray mode.

Step 4: Preparation of (R)—N-[1-cyclopropyl-1-(1,2,4-oxadiazol-3-yl)ethyl]-2-methylpropane-2-sulfinamide. (Z)-2-cyclopropyl-2-((R)-1,1-dimethylethylsulfinamido)-N'-hydroxypropanimidamide (321 mg, 1.30 mmol) in triethoxymethane (2.0 ml, 12 mmol) was treated with AcOH (2 ml) at rt. The reaction was allowed to stir at rt for 16 h. LCMS showed a major peak with the expected M+H. The reaction was concentrated to dryness azeotroping with toluene 2×. The resulting yellow oil was purified on silica gel (Biotage, EtOAc/hexanes gradient (Rf ~0.2 in 70% EtOAc/Hex, visualized with permanganate stain), to give the expected product (first eluting diastereomer, 120 mg, 0.466 mmol, 36% yield) consistent by LCMS and NMR. LC-MS retention time: 1.21 min; m/z M+H: 258. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% $H_2O$/0.1% trifluoroacetic acid and solvent B was 10% $H_2O$/90% acetonitrile/0.1% trifluoroacetic acid. MS data was determined using a Micromass Platform for LC in electrospray mode. $^1$H NMR (500 MHz, DMSO-$d_6$) δ 9.53 (s, 1H), 5.29 (s, 1H), 1.53-1.49 (m, 1H), 1.47 (s, 3H), 1.10 (s, 9H), 0.49-0.40 (m, 4H).

Step 5: 1-cyclopropyl-1-(1,2,4-oxadiazol-3-yl)ethan-1-amine hydrochloride. HCl (1 ml, 2 mmol) (2.0 M in $Et_2O$) was added to a stirring solution of (R)—N-(1-cyclopropyl-1-(1,2,4-oxadiazol-3-yl)ethyl)-2-methylpropane-2-sulfinamide (120 mg, 0.466 mmol) in MeOH (1 ml) at rt. The reaction was allowed to stir for 1 h at rt. The reaction was then concentrated to dryness azeotroping with toluene 3× to give the expected product 1-cyclopropyl-1-(1,2,4-oxadiazol-3-yl)ethanamine hydrochloride (87 mg, 0.46 mmol, 98% yield) consistent by NMR as a white solid. $^1$H NMR (500 MHz, METHANOL-$d_4$) δ 9.38 (s, 1H), 1.67 (s, 3H), 1.44 (s, 1H), 0.74-0.66 (m, 2H), 0.62-0.56 (m, 1H), 0.51-0.45 (m, 1H).

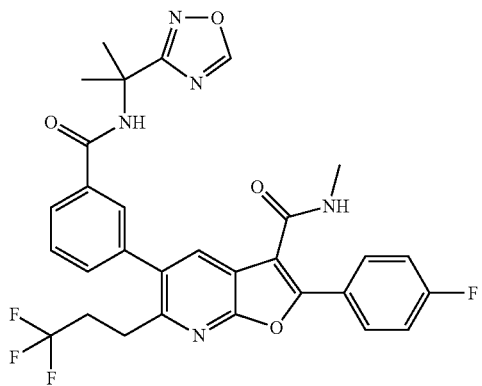 [SMILES: CNC(=O)c1c(-c2ccc(F)cc2)oc2nc(CCC(F)(F)F)c(-c3cccc(C(=O)NC(C)(C)c4ncon4)c3)cc12]

5-(3-((2-(1,2,4-oxadiazol-3-yl)propan-2-yl)carbamoyl)phenyl)-2-(4-fluorophenyl)-N-methyl-6-(3,3,3-trifluoropropyl)furo[2,3-b]pyridine-3-carboxamide 2-(3H-[1,2,3]triazolo[4,5-b]pyridin-3-yl)-1,1,3,3-tetramethylisouronium hexafluorophosphate(V) (879 mg, 2.31 mmol) was added to stirring solution of 3-(2-(4-fluorophenyl)-3-(methylcarbamoyl)-6-(3,3,3-trifluoropropyl)furo[2,3-b]pyridin-5-yl)benzoic acid (750 mg, 1.54 mmol), N-ethyl-N-isopropylpropan-2-amine (0.81 ml, 4.6 mmol) and 2-(1,2,4-oxadiazol-3-yl)propan-2-amine hydrochloride (277 mg, 1.70 mmol) in DMF (10 ml) at rt. The mixture was allowed to stir at rt for 1 h. The reaction mixture was then concentrated and purified on silica gel (Biotage, EtOAc/DCM gradient, fraction collection at λ=254 nm) to give the expected product 5-(3-(2-(1,2,4-oxadiazol-3-yl)propan-2-yl)carbamoyl)phenyl)-2-(4-fluorophenyl)-N-methyl-6-(3,3,3-trifluoropropyl) furo[2,3-b]pyridine-3-carboxamide (711 mg, 1.17 mmol, 76% yield) consistent by LCMS and NMR. LC-MS retention time: 1.76 min; m/z (MH+): 596. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% $H_2O$/0.1% trifluoroacetic acid and solvent B was 10% $H_2O$/90% acetonitrile/0.1% trifluoroacetic acid. MS data was determined using a Micromass Platform for LC in electrospray mode. $^1$H NMR (500 MHz, DMSO-$d_6$) δ 9.43 (s, 1H), 8.77 (s, 1H), 8.51 (q, J=4.3 Hz, 1H), 8.11-8.03 (m, 1H), 7.98 (s, 1H), 7.93 (d, J=7.6 Hz, 1H), 7.90 (s, 1H), 7.70 (m, 1H), 7.62 (m, 1H), 7.41 (t, J=8.8 Hz, 2H), 3.04 (m, 2H), 2.82 (d, J=4.4 Hz, 3H), 2.75 (m, 2H), 1.71 (s, 6H); $^{13}$C NMR (126 MHz, DMSO-$d_6$) δ 173.9, 166.4, 165.7, 162.4, 163.0 (d, J=247.5 Hz), 158.7, 151.9, 151.3, 138.7, 134.7, 133.0, 132.2, 131.6, 129.9 (d, J=8.2 Hz), 128.4, 127.1, 127.4 (q, J=275.0 Hz), 125.2, 117.5, 116.0 (d, J=22.5 Hz), 112.6, 51.1, 31.4 (q, J=27.5 Hz), 27.2, 26.6, 26.2; $^{19}$F NMR (470 MHz, DMSO-$d_6$) δ 64.8, −109.9 HRMS (+ESI)(MH+) Calcd for $C_{30}H_{26}F_4N_5O_4$: 596.1915. Found 596.1901; IR (KBr powder) 3600-2800, 1650-1638, 1510 cm$^{-1}$. Anal Calcd. (%) for $C_{30}H_{25}F_4N_5O_4$: C, 60.50; H, 4.23; N, 11.76. Found: C, 60.61; H, 4.01; N, 11.56.

Spray dried dispersions (SDD) were prepared at 10%, 15%, and 25% active ingredient with HPMCAS-MG (medium granular grade of hydroxypropylmethylcellulose acetate succinate) using Bend Research Mini SD and Pro-CepT microspray dryers. Two additional SDDs were prepared at 15% active ingredient with HPMCAS-HG and PVP VA64 using Bend Research Mini SD microspray dryer. The SDDs were prepared with active ingredient and co-polymers. The SDDs using HPMCAS-MG and -HG were prepared using THF/water solution (95:5) and the PVP VA64 was prepared using acetone. The inlet temperature of the spray dry apparatus is typically about 60-100° C., while the outlet temperature is about 30-60° C.

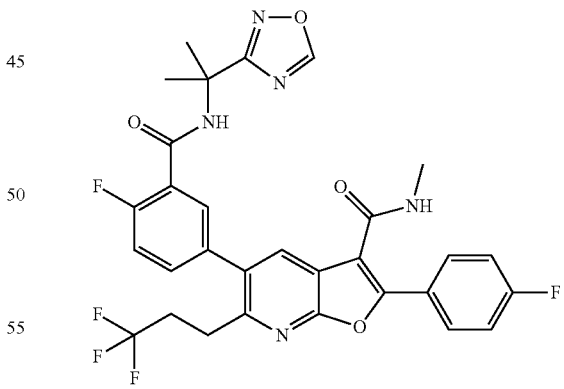

5-(3-((2-(1,2,4-oxadiazol-3-yl)propan-2-yl)carbamoyl)-4-fluorophenyl)-2-(4-fluorophenyl)-N-methyl-6-(3,3,3-trifluoropropyl)furo[2,3-b]pyridine-3-carboxamide 2-(3H-[1,2,3]triazolo[4,5-b]pyridin-3-yl)-1,1,3,3-tetramethylisouronium hexafluorophosphate(V) (23 mg, 0.059 mmol) was added to stirring solution of 2-fluoro-5-(2-(4- fluorophenyl)-3-(methylcarbamoyl)-6-(3,3,3-trifluoropropyl)furo[2,3-b]pyridin-5-yl)benzoic acid (20 mg, 0.040 mmol), N-ethyl-N-isopropylpropan-2-amine (0.021 mL, 0.12 mmol) and 2-(1,2,4-oxadiazol-3-yl)propan-2-amine hydrochloride (10 mg, 0.059 mmol) in DMF (1 mL) at rt. The mixture was allowed to stir at rt for 30 min. The crude reaction mixture was purified via preparative LC/MS with the following conditions: Column:Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 20-100% B over 20 minutes, then a 5-minute hold at 100% B; Flow: 20 mL/min. Fractions containing the desired product were combined and dried via centrifugal evaporation. The material was further purified via preparative LC/MS with the following conditions: Column:Waters XBridge C18, 19×200 mm, 5-μm particles; Mobile Phase A: water with 20-mM ammonium acetate; Mobile Phase B: 95:5 methanol:water with 20-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 40-80% B over 40 minutes, then a 5-minute hold at 100% B; Flow: 20 mL/min. Fractions containing the desired product were combined and dried via centrifugal evaporation. The yield of the product was 7.7 mg, and its estimated purity by LCMS analysis was 100%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. retention time: 3.04 min; M+H: 614. Injection 2 conditions: Column:Waters BEH C18, 2.0×50 mm, 1.7-μm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. retention time: 4.03 min; M+H: 614. Proton NMR was acquired in deuterated DMSO. $^1$H NMR (500 MHz, DMSO-d$_6$) δ 9.45 (s, 1H), 8.85 (s, 1H), 8.55-8.48 (m, 1H), 8.08-8.01 (m, 2H), 7.93 (s, 1H), 7.66-7.59 (m, 1H), 7.57-7.51 (m, 1H), 7.46-7.37 (m, 3H), 3.04-2.96 (m, 2H), 2.85-2.69 (m, J=3.7 Hz, 5H), 1.68 (s, 6H).

5-(3-((2-(1,2,4-oxadiazol-3-yl)propan-2-yl)carbamoyl)-4-methoxyphenyl)-2-(4-fluorophenyl)-N-methyl-6-(3,3,3-trifluoropropyl)furo[2,3-b]pyridine-3-carboxamide 2-(3H-[1,2,3]triazolo[4,5-b]pyridin-3-yl)-1,1,3,3-tetramethylisouronium hexafluorophosphate(V) (33 mg, 0.087 mmol) was added to stirring solution of 5-(2-(4-fluorophenyl)-3-(methylcarbamoyl)-6-(3,3,3-trifluoropropyl)furo[2,3-b]pyridin-5-yl)-2-methoxybenzoic acid (30 mg, 0.058 mmol), N-ethyl-N-isopropylpropan-2-amine (0.030 mL, 0.17 mmol) and 2-(1,2,4-oxadiazol-3-yl)propan-2-amine hydrochloride (14 mg, 0.087 mmol) in DMF (1 mL) at rt. The mixture was allowed to stir at rt for 30 min. The crude reaction mixture was then purified via preparative LC/MS with the following conditions: Column:Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 25-100% B over 20 minutes, then a 5-minute hold at 100% B; Flow: 20 mL/min. Fractions containing the desired product were combined and dried via centrifugal evaporation. The material was further purified via preparative LC/MS with the following conditions: Column:Waters XBridge C18, 19×200 mm, 5-μm particles; Mobile Phase A: water with 20-mM ammonium acetate; Mobile Phase B: 95:5 methanol:water with 20-mM ammonium acetate; Gradient: 0-100% B over 20 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 97%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. retention time: 3.12 min; M+H: 626. Injection 2 conditions: Column:Waters BEH C18, 2.0×50 mm, 1.7-μm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. retention time: 4.00 min; M+H: 626. Proton NMR was acquired in deuterated DMSO. $^1$H NMR (500 MHz, DMSO-d$_6$) δ 9.46 (s, 1H), 8.67 (s, 1H), 8.53-8.46 (m, 1H), 8.08-8.01 (m, 2H), 7.88 (s, 1H), 7.72 (s, 1H), 7.62-7.57 (m, 1H), 7.40 (s, 2H), 7.35-7.29 (m, 1H), 4.03 (s, 3H), 3.04-2.96 (m, 2H), 2.83-2.69 (m, 5H), 1.72 (s, 6H).

N-(1-(1,2,4-oxadiazol-3-yl)cyclobutyl)-2-methylpropane-2-sulfinamide

Step 1: Preparation of N-cyclobutylidene-2-methylpropane-2-sulfinamide: 2-methylpropane-2-sulfinamide (4.32 g, 35.7 mmol) and titanium(IV) ethoxide (16.3 g, 71.3 mmol) were added sequentially to a solution of cyclobutanone (2.5 g, 35.7 mmol) in THF (102 ml) at 22° C. The mixture was stirred at 60° C. for 5 h. The reaction mixture poured over a stirring saturated aqueous sodium chloride solution (60 mL). Celite was added to the suspension and it was filtered through a pad of Celite, washing with ethyl acetate (300 mL). The filtrate was washed with brine and the organic layers were combined and dried with anhydrous sodium sulfate. The dried solution was filtered and the filtrate was concentrated, yielding an oil

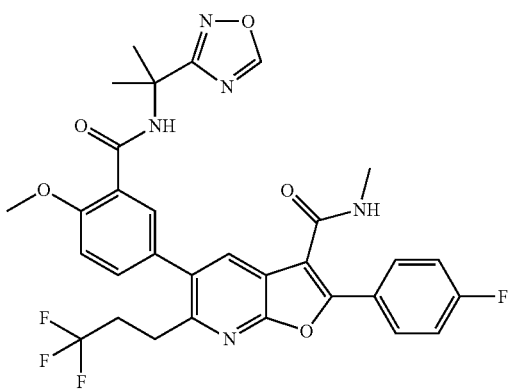 [SMILES: CNC(=O)c1c(-c2ccc(F)cc2)oc2nc(CCC(F)(F)F)c(-c3ccc(OC)c(C(=O)NC(C)(C)c4ncon4)c3)cc12]

which was purified on silica gel (Biotage, 25 g column, EtOAc/hexanes gradient, fraction collection at λ=254 nm) to give the expected product N-cyclobutylidene-2-methylpropane-2-sulfinamide (4.6 g, 27 mmol, 74% yield) consistent by NMR. $^1$H NMR (400 MHz, CHLOROFORM-d) δ 3.59-3.22 (m, 2H), 3.21-3.03 (m, 2H), 2.12 (t, J=8.2 Hz, 2H), 1.24 (s, 9H).

Step 2: Preparation of N-(1-cyanocyclobutyl)-2-methylpropane-2-sulfinamide: Titanium (IV) ethoxide (3.03 g, 13.3 mmol) was added to a stirring solution of trimethylsilyl cyanide (7.12 mL, 53.1 mmol) and N-cyclobutylidene-2-methylpropane-2-sulfinamide (4.6 g, 27 mmol) in DCM (100 mL) at rt. The reaction was allowed to stir for 16 h. An additional 1.7 mL of TMS-CN was added followed by 1.5 g of TiOEt$_4$. The reaction was allowed to stir at rt for an additional 16 h. The mixture was diluted with EtOAc and washed with sat NaHCO$_3$, and sat NaCl. The organic phase was dried over Na$_2$SO$_4$, filtered and concentrated to give N-(1-cyanocyclobutyl)-2-methylpropane-2-sulfinamide (4.5 g, 22 mmol, 85% yield) consistent by NMR. $^1$H NMR (400 MHz, CHLOROFORM-d) δ 2.82-2.67 (m, 2H), 2.62-2.34 (m, 2H), 2.26-2.02 (m, 2H), 1.26 (s, 9H).

Step 3: Preparation of (Z)-1-(1,1-dimethylethylsulfinamido)-N'-hydroxycyclobutanecarboximidamide: Potassium carbonate (1.38 g, 9.98 mmol) was added to a stirring solution of hydroxylamine hydrochloride (347 mg, 4.99 mmol) and N-(1-cyanocyclobutyl)-2-methylpropane-2-sulfinamide (500 mg, 2.50 mmol) in EtOH (8 ml) at rt. The reaction was then heated to 60° C. for 16 h. The mixture was then concentrated and the resulting residue was diluted with EtOAc and washed with H$_2$O followed by sat NaCl (aq). The organic phase was dried over Na$_2$SO$_4$, filtered and concentrated to give the expected product (Z)-1-(1,1-dimethylethylsulfinamido)-N'-hydroxycyclobutanecarboximidamide (305 mg, 1.31 mmol, 52% yield) as a white solid consistent by LCMS and NMR. LC-MS retention time: 0.456 min; m/z (MH+): 234. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. $^1$H NMR (400 MHz, DMSO-d$_6$) δ 9.20 (s, 1H), 5.60 (s, 1H), 5.10 (s, 2H), 2.35-2.30 (m, 1H), 2.27-2.17 (m, 1H), 2.10-2.03 (m, 1H), 1.99 (s, 1H), 1.80-1.75 (m, 1H), 1.73-1.62 (m, 1H), 1.13 (s, 9H).

Step 4: Preparation of the titled compound: (Z)-1-(1,1-dimethylethylsulfinamido)-N'-hydroxycyclobutanecarboximidamide (300 mg, 1.29 mmol) was taken up in dioxane (6 ml) and treated with N,N-Dimethylformamide dimethyl acetal (2.6 ml, 19 mmol) at rt. The reaction was then heated to 70° C. for 4 h. LCMS showed that starting material had been consumed. The expected M+H of 244 was observed in one of the minor peaks. The reaction was concentrated under high vacuum and the residue was purified by preparative reverse phase HPLC on a C18 column using a NH$_4$OAc buffered H$_2$O/CH$_3$CN gradient, and concentrated to give N-(1-(1,2,4-oxadiazol-3-yl)cyclobutyl)-2-methylpropane-2-sulfinamide (45 mg, 0.19 mmol, 14% yield) as a light brown oil consistent by LCMS. LC-MS retention time: 1.31 min; m/z (MH+): 244. LC data was recorded on a Shimadzu LC-10AS liquid chromatograph equipped with a Phenomenex-Luna 3u C18 2.0× 30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

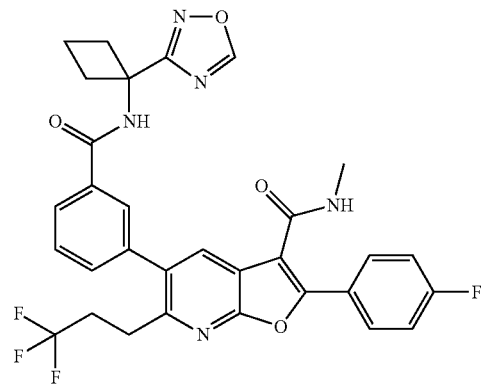 [SMILES: CNC(=O)c1c(-c2ccc(F)cc2)oc2nc(CCC(F)(F)F)c(-c3cccc(C(=O)NC4(c5ncon5)CCC4)c3)cc12]

5-(3-((1-(1,2,4-oxadiazol-3-yl)cyclobutyl)carbamoyl)phenyl)-2-(4-fluorophenyl)-N-methyl-6-(3,3,3-trifluoropropyl)furo[2,3-b]pyridine-3-carboxamide N-(1-(1,2,4-oxadiazol-3-yl)cyclobutyl)-2-methylpropane-2-sulfinamide (45 mg, 0.19 mmol) was taken up in 1 mL of MeOH and treated with 1 mL of HCl (2M in Et$_2$O) at rt and allowed to stir for 30 min at rt. The reaction was then concentrated to dryness azeotroping with toluene 3× to give 1-(1,2,4-oxadiazol-3-yl)cyclobutanamine hydrochloride (32 mg, 0.18 mmol). Then 14 mg (0.077 mmol) of this material was combined with 3-(2-(4-fluorophenyl)-3-(methylcarbamoyl)-6-(3,3,3-trifluoropropyl)furo[2,3-b]pyridin-5-yl)benzoic acid (25 mg, 0.051 mmol) and N-ethyl-N-isopropylpropan-2-amine (0.027 mL, 0.15 mmol) in DMF (1 mL) at rt. To this stirring solution 2-(3H-[1,2,3]triazolo[4,5-b]pyridin-3-yl)-1,1,3,3-tetramethylisouronium hexafluorophosphate(V) (29 mg, 0.077 mmol) was added. The mixture was allowed to stir at rt for 30 min. The crude reaction mixture was purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 20.2 mg, and its estimated purity by LCMS analysis was 100%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. retention time: 3.02 min; M+H: 608. Injection 2 conditions: Column:Waters BEH C18, 2.0×50 mm, 1.7-μm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. retention time: 4.06 min; M+H: 608. Proton NMR was acquired in deuterated DMSO. ¹H NMR (500 MHz, DMSO-$d_6$) δ 9.48 (s, 1H), 9.33 (s, 1H), 8.55-8.46 (m, 1H), 8.10-8.02 (m, 2H), 7.98 (s, 3H), 7.69-7.59 (m, 2H), 7.46-7.37 (m, 2H), 3.05-2.97 (m, 2H), 2.85-2.71 (m, 5H), 2.67-2.56 (m, 4H), 2.10-1.99 (m, 2H).

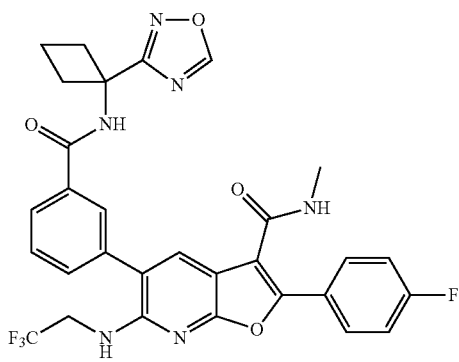 [SMILES: CNC(=O)c1c(-c2ccc(F)cc2)oc2nc(NCC(F)(F)F)c(-c3cccc(C(=O)NC4(c5ncon5)CCC4)c3)cc12]

5-(3-((1-(1,2,4-oxadiazol-3-yl)cyclobutyl)carbamoyl)phenyl)-2-(4-fluorophenyl)-N-methyl-6-((2,2,2-trifluoroethyl)amino)furo[2,3-b]pyridine-3-carboxamide 2-(3H-[1,2,3]triazolo[4,5-b]pyridin-3-yl)-1,1,3,3-tetramethylisouronium hexafluorophosphate(V) (29 mg, 0.077 mmol) was added to stirring solution of 3-(2-(4-fluorophenyl)-3-(methylcarbamoyl)-6-((2,2,2-trifluoroethyl)amino) furo[2,3-b]pyridin-5-yl)benzoic acid (25 mg, 0.051 mmol), N-ethyl-N-isopropylpropan-2-amine (0.027 mL, 0.15 mmol) and 1-(1,2,4-oxadiazol-3-yl)cyclobutanamine hydrochloride (14 mg, 0.077 mmol) in DMF (1 mL) at rt. The mixture was allowed to stir at rt. for 30 min. The crude material was purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 4.0 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. retention time: 2.95 min; M+H: 609. Injection 2 conditions: Column: Waters Acquity UPLC BEH C18, 2.1×50 mm, 1.7-μm particles; Mobile Phase A: 5:95 acetonitrile: water with 0.05% TFA; Mobile Phase B: 95:5 acetonitrile: water with 0.1% TFA; Temperature: 50° C.; Gradient: 0-100% B over 3 minutes, then a 0.75-minute hold at 100% B; Flow: 1.11 mL/min. retention time: 3.02 min; M+H: 609. Proton NMR was acquired in deuterated DMSO. ¹H NMR (500 MHz, DMSO-$d_6$) δ 9.49 (s, 1H), 9.31 (s, 1H), 8.42-8.32 (m, 1H), 8.01-7.90 (m, 4H), 7.69 (s, 1H), 7.66-7.55 (m, 2H), 7.39-7.29 (m, 2H), 6.65-6.59 (m, 1H), 4.23-4.11 (m, 2H), 2.79 (d, J=4.3 Hz, 3H), 2.68-2.55 (m, 4H), 2.10-2.00 (m, 2H).

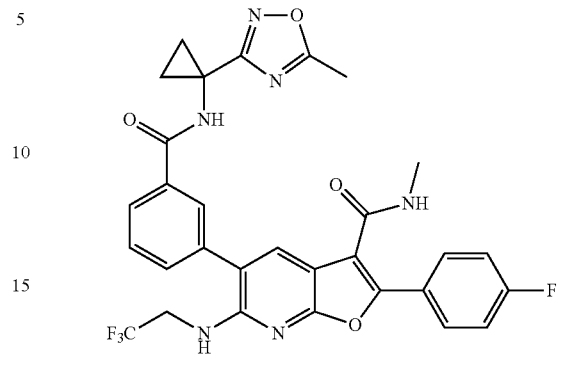

2-(4-fluorophenyl)-N-methyl-5-(3-((1-(5-methyl-1,2,4-oxadiazol-3-yl)cyclopropyl)carbamoyl)phenyl)-6-((2,2,2-trifluoroethyl)amino)furo[2,3-b]pyridine-3-carboxamide 2-(3H-[1,2,3]triazolo[4,5-b]pyridin-3-yl)-1,1,3,3-tetramethylisouronium hexafluorophosphate(V) (23 mg, 0.062 mmol) was added to stirring solution of 3-(2-(4-fluorophenyl)-3-(methylcarbamoyl)-6-((2,2,2-trifluoroethyl)amino) furo[2,3-b]pyridin-5-yl)benzoic acid (20 mg, 0.041 mmol), N-ethyl-N-isopropylpropan-2-amine (0.022 mL, 0.12 mmol) and 1-(5-methyl-1,2,4-oxadiazol-3-yl)cyclopropanamine hydrochloride (18 mg, 0.10 mmol) in DMF (1 mL) at rt. The mixture was allowed to stir at rt for 1 h. Then, separately an additional amount of the amine: 1-(5-methyl-1,2,4-oxadiazol-3-yl)cyclopropanamine hydrochloride (18 mg, 0.10 mmol) was taken up in 2 mL of a 1:1 mixture of DMF: N-ethyl-N-isopropylpropan-2-amine and then concentrated. The resulting residue along with additional 3-(2-(4-fluorophenyl)-3-(methylcarbamoyl)-6-((2,2,2-trifluoroethyl) amino)furo[2,3-b]pyridin-5-yl)benzoic acid (20 mg, 0.041 mmol), N-ethyl-N-isopropylpropan-2-amine (0.022 mL, 0.12 mmol), and 2-(3H-[1,2,3]triazolo[4,5-b]pyridin-3-yl)-1, 1,3,3-tetramethylisouronium hexafluorophosphate(V) (23 mg, 0.062 mmol) was added to the original reaction mixture and the mixture was allowed to stir for 1 h at rt. The crude mixture was purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 30-70% B over 20 minutes, then a 5-minute hold at 100% B; Flow: 20 mL/min. Fractions containing the desired product were combined and dried via centrifugal evaporation. The yield of the product was 2.3 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. retention time: 2.77 min; M+H: 609. Injection 2 conditions: Column: Waters BEH C18, 2.0× 50 mm, 1.7-μm particles; Mobile Phase A: 5:95 methanol: water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. retention time: 3.81 min; M+H: 609. Proton NMR was acquired in deuterated DMSO. ¹H NMR (500 MHz, DMSO-d₆) δ 9.36 (s, 1H), 8.42-8.33 (m, 1H), 8.00-7.90 (m, 4H), 7.70-7.56 (m, 3H), 7.39-7.30 (m, 2H), 6.65-6.58 (m, 1H), 4.25-4.11 (m, 2H), 2.83-2.75 (m, 3H), 2.52 (s, 3H), 1.48-1.42 (m, 2H), 1.37-1.30 (m, 2H).

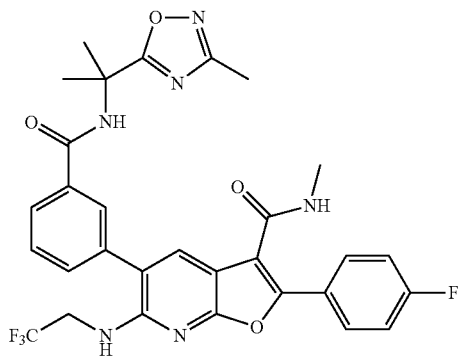 [SMILES: CNC(=O)c1c(-c2ccc(F)cc2)oc2nc(NCC(F)(F)F)c(-c3cccc(C(=O)NC(C)(C)c4nc(C)no4)c3)cc12]

2-(4-fluorophenyl)-N-methyl-5-(3-((2-(3-methyl-1,2,4-oxadiazol-5-yl)propan-2-yl)carbamoyl)phenyl)-6-((2,2,2-trifluoroethyl)amino)furo[2,3-b]pyridine-3-carboxamide 3-(2-(4-fluorophenyl)-3-(methylcarbamoyl)-6-((2,2,2-trifluoroethyl)amino)furo[2,3-b]pyridin-5-yl)benzoic acid (40 mg, 0.082 mmol) was taken up in DMF (1 ml) and treated with N-ethyl-N-isopropylpropan-2-amine (43 μL, 0.25 mmol), 2-(3-methyl-1,2,4-oxadiazol-5-yl)propan-2-amine hydrochloride (17 mg, 0.098 mmol) followed by 2-(3H-[1,2,3]triazolo[4,5-b]pyridin-3-yl)-1,1,3,3-tetramethylisouronium hexafluorophosphate(V) (47 mg, 0.12 mmol). The reaction mixture was allowed to stir for 1 h then the reaction was quenched with MeOH (1 mL) and the crude mixture was purified via preparative LC/MS with the following conditions: Column:Waters XBridge C18, 19×200 mm, 5-μm particles; Guard Column:Waters XBridge C18, 19×10 mm, 5-μm particles; Mobile Phase A: water with 20-mM ammonium acetate; Mobile Phase B: 95:5 methanol:water with 20-mM ammonium acetate; Gradient: 50-90% B over 40 minutes, then a 4-minute hold at 100% B; Flow: 20 mL/min. Fractions containing the desired product were combined and dried via centrifugal evaporation. The yield of the product was 17.0 mg, and its estimated purity by LCMS analysis was 96%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. retention time: 2.95 min; M+H: 611. Injection 2 conditions: Column:Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. retention time: 3.89 min; M+H: 611. Proton NMR was acquired in deuterated DMSO. ¹H NMR (500 MHz, DMSO-d₆) δ 8.99 (s, 1H), 8.41-8.33 (m, 1H), 8.01-7.88 (m, 4H), 7.68 (s, 1H), 7.65-7.57 (m, 2H), 7.34 (t, J=8.7 Hz, 2H), 6.62 (t, J=6.3 Hz, 1H), 4.24-4.09 (m, 2H), 2.79 (d, J=4.6 Hz, 3H), 2.31 (s, 3H), 1.70 (s, 6H.

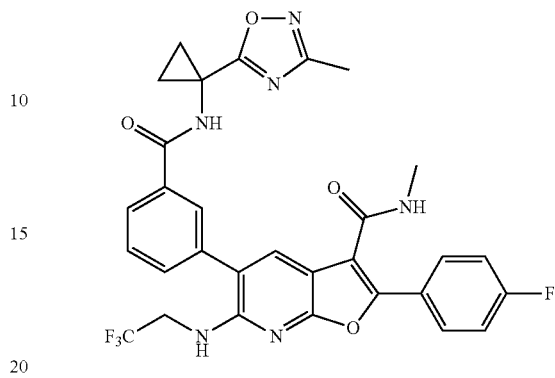

2-(4-fluorophenyl)-N-methyl-5-(3-((1-(3-methyl-1,2,4-oxadiazol-5-yl)cyclopropyl)carbamoyl)phenyl)-6-((2,2,2-trifluoroethyl)amino)furo[2,3-b]pyridine-3-carboxamide 3-(2-(4-fluorophenyl)-3-(methylcarbamoyl)-6-((2,2,2-trifluoroethyl)amino)furo[2,3-b]pyridin-5-yl)benzoic acid (40 mg, 0.082 mmol) was taken up in DMF (1 ml) and treated with N-ethyl-N-isopropylpropan-2-amine (43 μl, 0.25 mmol), 1-(3-methyl-1,2,4-oxadiazol-5-yl)cyclopropanamine hydrochloride (17 mg, 0.098 mmol) followed by 2-(3H-[1,2,3]triazolo[4,5-b]pyridin-3-yl)-1,1,3,3-tetramethylisouronium hexafluorophosphate(V) (47 mg, 0.12 mmol). The reaction was allowed to stir for 1 h. Then the reaction was quenched with MeOH (1 mL) and the crude mixture was purified via preparative LC/MS with the following conditions: Column:Waters XBridge C18, 19×200 mm, 5-μm particles; Guard Column:Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 20-100% B over 20 minutes, then a 5-minute hold at 100% B; Flow: 20 mL/min. Fractions containing the desired product were combined and dried via centrifugal evaporation. The yield of the product was 15.4 mg, and its estimated purity by LCMS analysis was 98%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. retention time: 2.87 min; M+H: 609. Injection 2 conditions: Column:Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. retention time: 3.84 min; M+H: 609. Proton NMR was acquired in deuterated DMSO. ¹H NMR (500 MHz, DMSO-d₆) δ 9.54 (s, 1H), 8.42-8.32 (m, 1H), 7.98-7.92 (m, 4H), 7.69-7.61 (m, 3H), 7.34 (t, J=8.9 Hz, 2H), 6.61 (t, J=6.3 Hz, 1H), 4.21-4.14 (m, 2H), 2.79 (d, J=4.6 Hz, 3H), 2.26 (s, 3H), 1.67-1.63 (m, 2H), 1.52-1.47 (m, 2H).

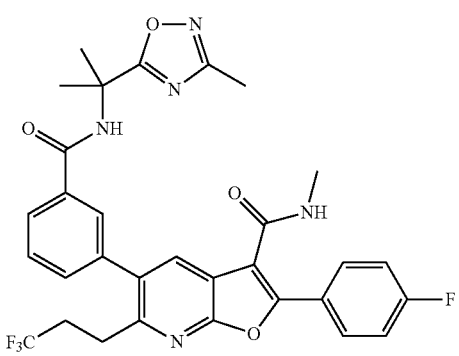 [SMILES: CNC(=O)c1c(-c2ccc(F)cc2)oc2nc(CCC(F)(F)F)c(-c3cccc(C(=O)NC(C)(C)c4nc(C)no4)c3)cc12]

2-(4-fluorophenyl)-N-methyl-5-(3-((2-(3-methyl-1,2,4-oxadiazol-5-yl)propan-2-yl)carbamoyl)phenyl)-6-(3,3,3-trifluoropropyl)furo[2,3-b]pyridine-3-carboxamide Step 1: Preparation of 2-(3-methyl-1,2,4-oxadiazol-5-yl)propan-2-amine hydrochloride: CDI (886 mg, 5.47 mmol) was added portion wise to a stirring solution of 2-((tert-butoxycarbonyl)amino)-2-methylpropanoic acid (1.01 g, 4.97 mmol) in DMF (2.0 ml) at rt. The reaction was allowed to stir for 5 h resulting in a slurry. (Z)—N'-hydroxyacetimidamide (442 mg, 5.96 mmol) was added and the reaction became a solution again after minor gas evolution was observed. This mixture was allowed to stir for 1 h at rt then 100° C. for 16 h. The reaction was concentrated and then diluted with Et$_2$O and washed with H$_2$O. The organic phase was concentrated, taken up in Et$_2$O and treated with excess 2M HCl in Et$_2$O. The resulting mixture was allowed to stir for 30 min and then concentrated azeotroping with toluene 2×. The resulting solid was triturated with Et$_2$O to give the 2-(3-methyl-1,2,4-oxadiazol-5-yl)propan-2-amine hydrochloride (545 mg, 3.07 mmol, 62% yield) consistent by NMR. $^1$H NMR (400 MHz, DMSO-d$_6$) δ 9.26 (br s, 3H), 2.40 (s, 3H), 1.71 (s, 6H).

Step 2: Preparation of the titled compound: 3-(2-(4-fluorophenyl)-3-(methylcarbamoyl)-6-(3,3,3-trifluoropropyl)furo[2,3-b]pyridin-5-yl)benzoic acid (30 mg, 0.062 mmol) was taken up in DMF (1 ml) and treated with N-ethyl-N-isopropylpropan-2-amine (32 μl, 0.19 mmol), 2-(3-methyl-1,2,4-oxadiazol-5-yl)propan-2-amine hydrochloride (13 mg, 0.074 mmol) followed by 2-(3H-[1,2,3]triazolo[4,5-b]pyridin-3-yl)-1,1,3,3-tetramethylisouronium hexafluorophosphate(V) (35 mg, 0.093 mmol). The reaction was allowed to stir for 1 h. The crude material was purified via preparative LC/MS with the following conditions: Column:Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 18.1 mg, and its estimated purity by LCMS analysis was 98%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. retention time: 3.02 min; M+H: 610. Injection 2 conditions: Column:Waters BEH C18, 2.0×50 mm, 1.7-μm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. retention time: 4.06 min; M+H: 610. Proton NMR was acquired in deuterated DMSO. $^1$H NMR (500 MHz, DMSO-d$_6$) δ 9.03 (s, 1H), 8.56-8.46 (m, 1H), 8.09-7.99 (m, 2H), 7.98-7.86 (m, 3H), 7.68-7.58 (m, 2H), 7.41 (t, J=8.7 Hz, 2H), 3.04-2.95 (m, 2H), 2.84-2.69 (m, 5H), 1.70 (s, 6H).

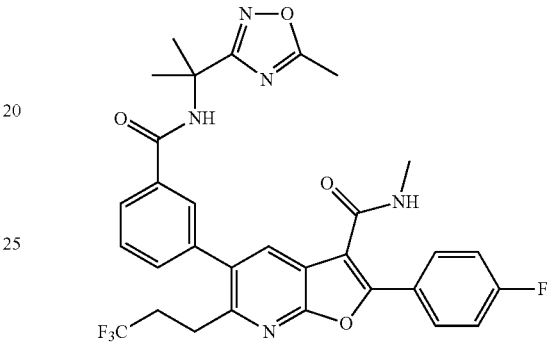

2-(4-fluorophenyl)-N-methyl-5-(3-((2-(5-methyl-1,2,4-oxadiazol-3-yl)propan-2-yl)carbamoyl)phenyl)-6-(3,3,3-trifluoropropyl)furo[2,3-b]pyridine-3-carboxamide N-ethyl-N-isopropylpropan-2-amine (0.043 mL, 0.25 mmol) was added to stirring solution of 3-(2-(4-fluorophenyl)-3-(methylcarbamoyl)-6-(3,3,3-trifluoropropyl)furo[2,3-b]pyridin-5-yl)benzoic acid (15 mg, 0.031 mmol), 2-(3H-[1,2,3]triazolo[4,5-b]pyridin-3-yl)-1,1,3,3-tetramethylisouronium hexafluorophosphate(V) (18 mg, 0.046 mmol) and 1,2,4-Oxadiazole-3-methanamine, α,α,5-trimethyl hydrochloride (5.5 mg, 0.031 mmol) in DMF (1 mL) at rt. The mixture was allowed to stir at rt for 1 h. LCMS shows complete reaction. The solution was diluted with MeOH, filtered and purified via preparative LC/MS with the following conditions: Column:Waters XBridge C18, 19×200 mm, 5-μm particles; Guard Column:Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 20-80% B over 20 minutes, then a 5-minute hold at100% B; Flow: 20 mL/min. Fractions containing the desired product were combined and dried via centrifugal evaporation. The yield of the product was 2.4 mg, and its estimated purity by LCMS analysis was 100%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column:Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. LC-MS retention time: 1.86 min; m/z (MH+): 610. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. $^1$H NMR (500 MHz, DMSO-$d_6$) δ 8.68 (br s, 1H), 8.50 (br s, 1H), 8.05 (br s, 2H), 8.00-7.86 (m, 3H), 7.61 (d, J=11.0 Hz, 2H), 7.41 (t, J=8.4 Hz, 2H), 3.03-2.97 (m, 2H), 3.22.81 (s, 3H), 2.79-2.71 (m, 2H), 2.53 (s, 3H), 1.67 (s, 6H).

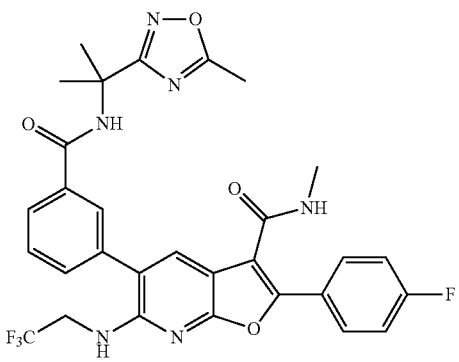 [SMILES: CNC(=O)c1c(-c2ccc(F)cc2)oc2nc(NCC(F)(F)F)c(-c3cccc(C(=O)NC(C)(C)c4noc(C)n4)c3)cc12]

2-(4-fluorophenyl)-N-methyl-5-(3-((2-(5-methyl-1,2,4-oxadiazol-3-yl)propan-2-yl)carbamoyl)phenyl)-6-((2,2,2-trifluoroethyl)amino)furo[2,3-b]pyridine-3-carboxamide N-ethyl-N-isopropylpropan-2-amine (0.043 mL, 0.25 mmol) was added to stirring solution of 3-(2-(4-fluorophenyl)-3-(methylcarbamoyl)-6-((2,2,2-trifluoroethyl)amino)furo[2,3-b]pyridin-5-yl)benzoic acid (15 mg, 0.031 mmol), 2-(3H-[1,2,3]triazolo[4,5-b]pyridin-3-yl)-1,1,3,3-tetramethylisouronium hexafluorophosphate(V) (18 mg, 0.046 mmol) and 1,2,4-Oxadiazole-3-methanamine, α,α,5-trimethyl hydrochloride (5.5 mg, 0.031 mmol) in DMF (1 mL) at rt. The mixture was allowed to stir at rt. for 1 h. LCMS shows complete reaction. The solution was diluted with MeOH, filtered and purified via preparative LC/MS with the following conditions: Column:Waters XBridge C18, 19×100 mm, 5-µm particles; Guard Column:Waters XBridge C18, 19×10 mm, 5-µm particles; Mobile Phase A: water; Mobile Phase B: acetonitrile; Buffer: 20-mM ammonium acetate; Gradient: 20-95% B over 10.9 minutes, then a 4.0 minute hold at 95% B; Flow: 25 mL/min. Fractions containing the desired product were combined and dried via centrifugal evaporation. The yield of the product was 2.3 mg, and its estimated purity by LCMS analysis was 100%. Two analytical LC/MS injections were used to determine the final purity. Injection 1 conditions: Column:Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column:Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. LC-MS retention time: 1.81 min; m/z (MH+): 611. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. $^1$H NMR (500 MHz, DMSO-$d_6$) δ 8.64 (br s, 1H), 8.38 (d, J=4.3 Hz, 1H), 8.00-7.84 (m, 4H), 7.68 (s, 1H), 7.63-7.55 (m, 2H), 7.34 (t, J=8.7 Hz, 2H), 6.63 (br s, 1H), 4.18 (m, 2H), 3.32 (m, 3H), 2.79 (d, J=4.3 Hz, 3H), 2.53 (s, 3H), 1.67 (s, 6H).

tert-butyl 3-(2-(4-fluorophenyl)-3-(methylcarbamoyl)-6-((2,2,2-trifluoroethyl)amino)furo[2,3-b]pyridin-5-yl)benzoate Sodium 2-methylbutan-2-olate (229 mg, 2.08 mmol), tert-butyl 3-(6-chloro-2-(4-fluorophenyl)-3-(methylcarbamoyl)furo[2,3-b]pyridin-5-yl)benzoate (200 mg, 0.416 mmol), 2,2,2-trifluoroethanamine (206 mg, 2.08 mmol), Chloro[2-(dicyclohexylphosphino)-3,6-dimethoxy-2'-4'-6'-tri-1-propyl-1,1'-biphenyl][2-(2-aminoethyl)phenyl]palladium (II) (33 mg, 0.042 mmol) was combined, degassed, and taken up in dioxane (8.3 ml) at rt and then was heated to 80° C. LCMS at 30 min showed major peak with M+H matching that of the expected product. The mixture was diluted with EtOAc and washed with 1M HCl aq, and sat NaCl aq. The organic phase was concentrated and triturated with DCM to give the expected product tert-butyl 3-(2-(4-fluorophenyl)-3-(methylcarbamoyl)-6-((2,2,2-trifluoroethyl)amino)furo[2,3-b]pyridin-5-yl)benzoate (130 mg, 0.239 mmol, 58% yield) consistent by LCMS. LC-MS retention time: 2.13 min; m/z (MH+): 544. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

3-(2-(4-fluorophenyl)-3-(methylcarbamoyl)-6-((2,2,2-trifluoroethyl)amino)furo[2,3-b]pyridin-5-yl)benzoic acid TFA (921 µl, 11.9 mmol) was added to a stirring solution of tert-butyl 3-(2-(4-fluorophenyl)-3-(methylcarbamoyl)-6-((2,2,2-trifluoroethyl)amino)furo[2,3-b]pyridin-5-yl)benzoate (130 mg, 0.239 mmol) in DCM (2.4 ml) at rt. The reaction was allowed to stir for 2 h then concentrated azeotroping with toluene to dryness. The resulting solid was triturated with DCM to give the expected product 3-(2-(4-fluorophenyl)-3-(methylcarbamoyl)-6-((2,2,2-trifluoroethyl)amino)furo[2,3-b]pyridin-5-yl)benzoic acid (97 mg, 0.20 mmol, 83% yield) consistent by LCMS and NMR. LC-MS retention time: 1.73 min; m/z (MH+): 488. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. $^1$H NMR (400 MHz, DMSO-d$_6$) δ 13.07 (br. s, 1H), 8.37-8.30 (m, J=4.5 Hz, 1H), 8.05-7.94 (m, 4H), 7.70-7.66 (m, 3H), 7.34 (t, J=8.9 Hz, 2H), 6.67 (s, 1H), 4.23-4.10 (m, J=3.0 Hz, 2H), 2.80 (d, J=4.8 Hz, 3H).

5-(2-(4-fluorophenyl)-3-(methylcarbamoyl)-6-((2,2,2-trifluoroethyl)amino)furo[2,3-b]pyridin-5-yl)-2-methoxybenzoic acid Sodium 2-methylbutan-2-olate (333 mg, 3.02 mmol), 5-(6-chloro-2-(4-fluorophenyl)-3-(methylcarbamoyl)furo[2,3-b]pyridin-5-yl)-2-methoxybenzoic acid (275 mg, 0.605 mmol), 2,2,2-trifluoroethanamine (299 mg, 3.02 mmol), Chloro[2-(dicyclohexylphosphino)-3,6-dimethoxy-2'-4'-6'-tri-1-propyl-1,1'-biphenyl][2-(2-aminoethyl)phenyl]palladium(II) (48 mg, 0.060 mmol) were combined, degassed, and taken up in dioxane (12 ml) at rt and then was heated to 90° C. The reaction was allowed to stir for 1 h. The mixture was then diluted with EtOAc and washed with 1M HCl aq, and sat NaCl aq. The organic phase was concentrated the resulting residue was purified by preparative reverse phase HPLC on a C18 column using a suitably buffered H$_2$O/CH$_3$CN gradient, and concentrated to give the expected product 5-(2-(4-fluorophenyl)-3-(methylcarbamoyl)-6-((2,2,2-trifluoroethyl)amino)furo[2,3-b]pyridin-5-yl)-2-methoxybenzoic acid (41 mg, 0.079 mmol, 13% yield) consistent by LCMS. LC-MS retention time: 1.87 min; m/z (MH+): 518. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode.

2-fluoro-5-(2-(4-fluorophenyl)-3-(methylcarbamoyl)-6-((2,2,2-trifluoroethyl)amino)furo[2,3-b]pyridin-5-yl)benzoic acid Sodium 2-methylbutan-2-olate (311 mg, 2.82 mmol), 5-(6-chloro-2-(4-fluorophenyl)-3-(methylcarbamoyl)furo[2,3-b]pyridin-5-yl)-2-fluorobenzoic acid (250 mg, 0.565 mmol), 2,2,2-trifluoroethanamine (280 mg, 2.82 mmol), Chloro[2-(dicyclohexylphosphino)-3,6-dimethoxy-2'-4'-6'-tri-1-propyl-1,1'-biphenyl][2-(2-aminoethyl)phenyl]palladium(II) (45 mg, 0.056 mmol) were combined, degassed, and taken up in dioxane (12 ml) at rt and then was heated to 90° C. for 1 h. The mixture was then diluted with EtOAc and washed with 1M HCl aq, and sat NaCl aq. The organic phase was dried over Na$_2$SO$_4$, filtered and concentrated. The resulting solid was triturated with DCM to give 250 mg crude material which was purified by preparative reverse phase HPLC on a C18 column using a suitably buffered H$_2$O/CH$_3$CN gradient, and concentrated to give the expected product 2-fluoro-5-(2-(4-fluorophenyl)-3-(methylcarbamoyl)-6-((2,2,2-trifluoroethyl)amino)furo[2,3-b]pyridin-5-yl)benzoic acid (100 mg, 0.198 mmol, 35% yield) consistent by LCMS and NMR. LC-MS retention time: 1.74 min; m/z (MH+): 506. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. $^1$H NMR (400 MHz, DMSO-d$_6$) δ 13.34 (br. s, 1H), 8.38-8.29 (m, 1H), 7.98 (dd, J=8.8, 5.5 Hz, 2H), 7.89 (dd, J=7.0, 2.3 Hz, 1H), 7.70-7.62 (m, 2H), 7.51-7.43 (m, 1H), 7.34 (t, J=8.9 Hz, 2H), 6.72 (s, 1H), 4.23-4.10 (m, 2H), 2.80 (d, J=4.8 Hz, 3H).

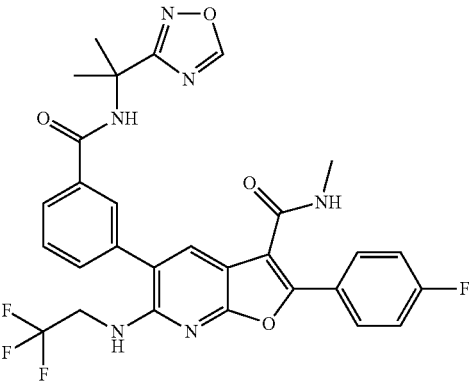 [SMILES: CNC(=O)c1c(-c2ccc(F)cc2)oc2nc(NCC(F)(F)F)c(-c3cccc(C(=O)NC(C)(C)c4ncon4)c3)cc12]

5-(3-((2-(1,2,4-oxadiazol-3-yl)propan-2-yl)carbamoyl)phenyl)-2-(4-fluorophenyl)-N-methyl-6-((2,2,2-trifluoroethyl)amino)furo[2,3-b]pyridine-3-carboxamide 2-(3H-[1,2,3]triazolo[4,5-b]pyridin-3-yl)-1,1,3,3-tetramethylisouronium hexafluorophosphate(V) (117 mg, 0.308 mmol) was added to stirring solution of 3-(2-(4-fluorophenyl)-3-(methylcarbamoyl)-6-((2,2,2-trifluoroethyl)amino)furo[2,3-b]pyridin-5-yl)benzoic acid (100 mg, 0.205 mmol), N-ethyl-N-isopropylpropan-2-amine (0.11 mL, 0.62 mmol) and 2-(1,2,4-oxadiazol-3-yl)propan-2-amine hydrochloride (50 mg, 0.31 mmol) in DMF (1 mL) at rt. The mixture was allowed to stir at rt for 1 h. The reaction mixture was then purified by preparative reverse phase HPLC on a C18 column using a suitably buffered H$_2$O/CH$_3$CN gradient, and concentrated to give the expected product 5-(3-((2-(1,2,4-oxadiazol-3-yl)propan-2-yl)carbamoyl)phenyl)-2-(4-fluorophenyl)-N-methyl-6-((2,2,2-trifluoroethyl)amino)furo[2,3-b]pyridine-3-carboxamide (61 mg, 0.10 mmol, 49% yield)) consistent by LCMS and NMR. LC-MS retention time: 1.73 min; m/z (MH+): 597. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. $^1$H NMR (400 MHz, DMSO-$d_6$) δ 9.43 (s, 1H), 8.70 (s, 1H), 8.40-8.32 (m, 1H), 8.01-7.94 (m, 2H), 7.93 (s, 1H), 7.90-7.85 (m, 1H), 7.69 (s, 1H), 7.64-7.57 (m, 2H), 7.38-7.31 (m, 2H), 6.63 (t, J=6.4 Hz, 1H), 4.26-4.12 (m, 2H), 2.80 (d, J=4.8 Hz, 3H), 1.70 (s, 6H).

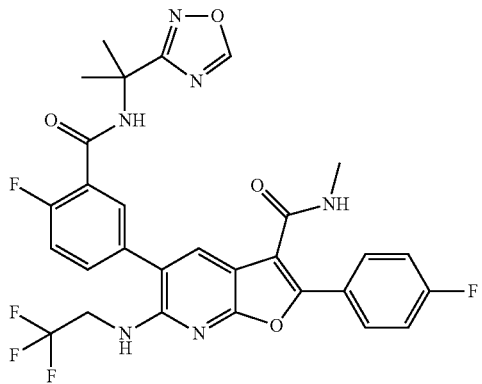 [SMILES: CNC(=O)c1c(-c2ccc(F)cc2)oc2nc(NCC(F)(F)F)c(-c3ccc(F)c(C(=O)NC(C)(C)c4ncon4)c3)cc12]

5-(3-((2-(1,2,4-oxadiazol-3-yl)propan-2-yl)carbamoyl)-4-fluorophenyl)-2-(4-fluorophenyl)-N-methyl-6-((2,2,2-trifluoroethyl)amino)furo[2,3-b]pyridine-3-carboxamide 2-(3H-[1,2,3]triazolo[4,5-b]pyridin-3-yl)-1,1,3,3-tetramethylisouronium hexafluorophosphate(V) (20 mg, 0.053 mmol) was added to stirring solution of 2-fluoro-5-(2-(4-fluorophenyl)-3-(methylcarbamoyl)-6-((2,2,2-trifluoroethyl)amino)furo[2,3-b]pyridin-5-yl)benzoic acid (18 mg, 0.036 mmol), N-ethyl-N-isopropylpropan-2-amine (0.019 mL, 0.11 mmol) and 2-(1,2,4-oxadiazol-3-yl)propan-2-amine hydrochloride (7.6 mg, 0.046 mmol) in DMF (1 mL) at rt. The mixture was allowed to stir at rt. for 30 min. The crude reaction mixture was purified via preparative LC/MS with the following conditions: Column:Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 30-70% B over 20 minutes, then a 5-minute hold at 100% B; Flow: 20 mL/min. Fractions containing the desired product were combined and dried via centrifugal evaporation. The yield of the product was 15.9 mg, and its estimated purity by LCMS analysis was 100%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. retention time: 2.92 min; M+H: 615. Injection 2 conditions: Column:Waters BEH C18, 2.0× 50 mm, 1.7-μm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. retention time: 3.91 min; M+H: 615. Proton NMR was acquired in deuterated DMSO. $^1$H NMR (500 MHz, DMSO-$d_6$) δ 9.47 (s, 1H), 8.73 (s, 1H), 8.41-8.34 (m, 1H), 8.00-7.92 (m, 2H), 7.68 (s, 1H), 7.64-7.54 (m, 2H), 7.44 (t, J=9.2 Hz, 1H), 7.35 (t, J=9.0 Hz, 2H), 6.70 (t, J=6.4 Hz, 1H), 4.24-4.13 (m, 2H), 2.80 (d, J=4.6 Hz, 3H), 1.69 (s, 6H).

5-(3-((2-(1,2,4-oxadiazol-3-yl)propan-2-yl)carbamoyl)-4-methoxyphenyl)-2-(4-fluorophenyl)-N-methyl-6-((2,2,2-trifluoroethyl)amino)furo[2,3-b]pyridine-3-carboxamide 2-(3H-[1,2,3]triazolo[4,5-b]pyridin-3-yl)-1,1,3,3-tetramethylisouronium hexafluorophosphate(V) (22 mg, 0.058 mmol) was added to stirring solution of 5-(2-(4-fluorophenyl)-3-(methylcarbamoyl)-6-((2,2,2-trifluoroethyl)amino) furo[2,3-b]pyridin-5-yl)-2-methoxybenzoic acid (20 mg, 0.039 mmol), N-ethyl-N-isopropylpropan-2-amine (0.020 mL, 0.12 mmol) and 2-(1,2,4-oxadiazol-3-yl)propan-2-amine hydrochloride (10 mg, 0.058 mmol) in DMF (1 mL) at rt. The mixture was allowed to stir at rt for 30 min. The crude reaction mixture was then purified via preparative LC/MS with the following conditions: Column:Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 20-100% B over 20 minutes, then a 5-minute hold at 100% B; Flow: 20 mL/min. Fractions containing the desired product were combined and dried via centrifugal evaporation. The yield of the product was 9.5 mg, and its estimated purity by LCMS analysis was 97%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. retention time: 3.02 min; M+H: 627. Injection 2 conditions: Column:Waters BEH C18, 2.0×50 mm, 1.7-μm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. retention time: 3.85 min; M+H: 627. Proton NMR was acquired in deuterated DMSO. $^1$H NMR (500 MHz, DMSO-d$_6$) δ 9.47 (s, 1H), 8.65 (s, 1H), 8.39-8.31 (m, 1H), 7.97 (dd, J=8.9, 5.5 Hz, 2H), 7.79-7.73 (m, 1H), 7.60 (s, 1H), 7.54 (dd, J=8.5, 2.1 Hz, 1H), 7.37-7.28 (m, 3H), 6.58-6.53 (m, 1H), 4.22-4.08 (m, 2H), 4.01 (s, 3H), 2.79 (d, J=4.6 Hz, 3H), 1.73 (s, 6H).

1-(1,2,4-oxadiazol-3-yl)cyclopropanamine hydrochloride

Step 1: Preparation of N-(1-cyanocyclopropyl)-2-methylpropane-2-sulfinamide: 2-methylpropane-2-sulfinic chloride (1.0 ml, 8.4 mmol) was added to a stirring solution of 1-aminocyclopropanecarbonitrile hydrochloride (1 g, 8 mmol) in dichloromethane (21 ml) and N-ethyl-N-isopropylpropan-2-amine (3.0 ml, 17 mmol) at 0° C. DMAP (10 mg, 0.084 mmol) was added and the reaction was allowed to stir 2 h at rt. The mixture was diluted with dichloromethane and washed with sat NH$_4$Cl aq, and sat NaCl aq. The organic phase was dried over Na$_2$SO$_4$, filtered and concentrated to give the expected product N-(1-cyanocyclopropyl)-2-methylpropane-2-sulfinamide (1.5 g, 8.1 mmol, 95% yield) as a sticky yellow solid consistent by LCMS. LC-MS retention time: 1.40 min; m/z (MH+): 187. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode.

Step 2: Preparation of (Z)-1-(1,1-dimethylethylsulfinamido)-N'-hydroxycyclopropanecarboximidamide: Potassium carbonate (4.45 g, 32.2 mmol) and hydroxylamine hydrochlordie (1.1 g, 16 mmol) was added to a stirring solution of N-(1-cyanocyclopropyl)-2-methylpropane-2-sulfinamide (1.5 g, 8.1 mmol) in EtOH (27 ml) at rt. The reaction was heated to 60° C. for 2 h. Then the reaction was allowed to cool to rt. Celite was added and the mixture was filtered through a pad of celite washing with 100 mL of EtOAc. The filtrate was concentrated to give the expected product (Z)-1-(1,1-dimethylethylsulfinamido)-N'-hydroxycyclopropanecarboximidamide (1.7 g, 7.8 mmol, 96% yield) consistent by LCMS. LC-MS retention time: 1.09 min; m/z (MH+): 220. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode.

Step 3: Preparation of N-(1-(1,2,4-oxadiazol-3-yl)cyclopropyl)-2-methylpropane-2-sulfinamide: (Z)-1-(1,1-dimethylethylsulfinamido)-N'-hydroxycyclopropanecarboximidamide (1.0 g, 4.6 mmol) in triethoxymethane (6.0 ml, 36 mmol) was treated with AcOH (6 ml) at rt. The reaction was allowed to stir at rt for 16 h. The reaction was concentrated to dryness azeotroping with toluene 3×. The resulting yellow oil which was purified on silica gel (Biotage, EtOAc/hexanes gradient (Rf ~approximately 2 in 70% EtOAc/Hex) to give the expected product N-(1-(1,2,4-oxadiazol-3-yl)cyclopropyl)-2-methylpropane-2-sulfinamide (340 mg, 1.5 mmol, 33% yield) consistent by LCMS and NMR. LC-MS retention time: 1.06 min; m/z (MH+): 230. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. $^1$H NMR (400 MHz, DMSO-d$_6$) δ 9.44 (s, 1H), 6.36 (s, 1H), 1.57-1.51 (m, 1H), 1.45-1.32 (m, 3H), 1.15 (s, 9H).

Step 4: Preparation of the titled compound: 1-(1,2,4-oxadiazol-3-yl)cyclopropanamine hydrochloride: HCl (3 ml, 6 mmol) (2.0 M in Et$_2$O) was added to a stirring solution of N-(1-(1,2,4-oxadiazol-3-yl)cyclopropyl)-2-methylpropane-2-sulfinamide (340 mg, 1.5 mmol) in MeOH (3 ml) at rt. The reaction was allowed to stir for 1 h at rt. The reaction was then concentrated to dryness azeotroping with toluene 3× to give the expected product 1-(1,2,4-oxadiazol-3-yl)cyclopropanamine hydrochloride (220 mg, 1.38 mmol, 93% yield) consistent by NMR as a white solid. $^1$H NMR (400 MHz, MeOH-d$_4$) δ 9.29 (s, 1H), 1.65-1.61 (m, 2H), 1.61-1.58 (m, 2H).

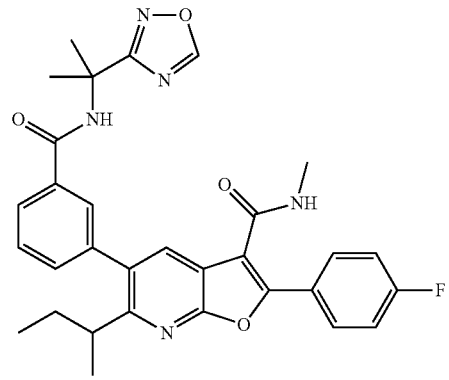 [SMILES: CCC(C)c1nc2oc(-c3ccc(F)cc3)c(C(=O)NC)c2cc1-c1cccc(C(=O)NC(C)(C)c2ncon2)c1]

5-(3-((2-(1,2,4-oxadiazol-3-yl)propan-2-yl)carbamoyl)phenyl)-6-(sec-butyl)-2-(4-fluorophenyl)-N-methylfuro[2,3-b]pyridine-3-carboxamide and separation into pure isomers Step 1: Preparation of (E)-tert-butyl 3-(6-(but-2-en-2-yl)-2-(4-fluorophenyl)-3-(methylcarbamoyl)furo[2,3-b]pyridin-5-yl)benzoate: tert-butyl 3-(6-chloro-2-(4-fluorophenyl)-3-(methylcarbamoyl)furo[2,3-b]pyridin-5-yl)benzoate (250 mg, 0.520 mmol), potassium (Z)-but-2-en-2-yltrifluoroborate (100 mg, 0.617 mmol), sodium 6-(dicyclohexylphosphino)-2',6'-dimethoxy-[1,1'-biphenyl]-3-sulfonate (107 mg, 0.208 mmol), diacetoxypalladium (23.3 mg, 0.104 mmol), cesium carbonate (254 mg, 0.780 mmol) were combined dry, degassed with N$_2$ and then taken up in DMF (4.7 ml) and water (0.47 ml) and heated to 80° C. for 1 h. The reaction was then concentrated to dryness azeotroping with toluene and the crude mixture was adsorbed onto Celite and was purified on silica gel (Biotage, EtOAc/hexanes gradient, fraction collection at λ=254 nm) give the expected product (E)-tert-butyl 3-(6-(but-2-en-2-yl)-2-(4-fluorophenyl)-3-(methylcarbamoyl)furo[2,3-b]pyridin-5-yl)benzoate (118 mg, 0.236 mmol, 45% yield) consistent by LCMS and NMR. LC-MS retention time: 2.22 min; m/z (MH+): 501. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. $^1$H NMR (400 MHz, DMSO-$d_6$) δ 8.51-8.43 (m, 1H), 8.10-8.04 (m, 2H), 8.01 (s, 1H), 7.96-7.93 (m, 1H), 7.91-7.87 (m, 1H), 7.68-7.64 (m, 1H), 7.60-7.54 (m, 1H), 7.45-7.37 (m, 2H), 5.44-5.37 (m, 1H), 2.83 (d, J=4.5 Hz, 3H), 1.87-1.82 (m, 3H), 1.59-1.52 (m, 12H).

Step 2: Preparation of tert-butyl 3-(6-(sec-butyl)-2-(4-fluorophenyl)-3-(methylcarbamoyl)furo[2,3-b]pyridin-5-yl) benzoate: Pd/C (50 mg, 0.047 mmol, 10%) was added to a stirring solution of (E)-tert-butyl 3-(6-(but-2-en-2-yl)-2-(4-fluorophenyl)-3-(methylcarbamoyl)furo[2,3-b]pyridin-5-yl) benzoate (118 mg, 0.236 mmol) in EtOH (4.7 ml) at rt. The reaction was placed in a Parr bomb and charged with 50 PSI of H$_2$ and the mixture was allowed to stir for 16 h at rt. Celite was added to the reaction mixture and the slurry was filtered through a pad of Celite washing with EtOAc. The filtrate was concentrated to give the expected product tert-butyl 3-(6-(sec-butyl)-2-(4-fluorophenyl)-3-(methylcarbamoyl)furo[2,3-b]pyridin-5-yl)benzoate (118 mg, 0.235 mmol, 100% yield) consistent by LCMS. LC-MS retention time: 2.38 min; m/z (MH+): 503. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 2 min, and an analysis time of 4 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode.

Step 3: Preparation of 3-(6-(sec-butyl)-2-(4-fluorophenyl)-3-(methylcarbamoyl)furo[2,3-b]pyridin-5-yl)benzoic acid: TFA (0.90 ml, 12 mmol) was added to a stirring solution of tert-butyl 3-(6-(sec-butyl)-2-(4-fluorophenyl)-3-(methylcarbamoyl)furo[2,3-b]pyridin-5-yl)benzoate (118 mg, 0.235 mmol) in DCM (2.3 ml) at rt. The reaction was allowed to stir for 2 h and then was concentrated to dryness azeotroping with toluene 2×. The resulting solid was triturated with DCM to give 3-(6-(sec-butyl)-2-(4-fluorophenyl)-3-(methylcarbamoyl)furo[2,3-b]pyridin-5-yl)benzoic acid (98 mg, 0.22 mmol, 93% yield) consistent by LCMS. LC-MS retention time: 1.84 min; m/z (MH+): 447. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 4: Preparation of the titled compound 2-(3H-[1,2,3] triazolo[4,5-b]pyridin-3-yl)-1,1,3,3-tetramethylisouronium hexafluorophosphate(V) (38 mg, 0.10 mmol) was added to stirring solution of 3-(6-(sec-butyl)-2-(4-fluorophenyl)-3-(methylcarbamoyl)furo[2,3-b]pyridin-5-yl)benzoic acid (30 mg, 0.067 mmol), N-ethyl-N-isopropylpropan-2-amine (35 µl, 0.20 mmol) and 2-(1,2,4-oxadiazol-3-yl)propan-2-amine hydrochloride (13 mg, 0.081 mmol) in DMF (1 ml) at rt. The mixture was allowed to stir at rt for 30 min. The crude material was purified via preparative LC/MS with the following conditions: Column:Waters XBridge C18, 19×200 mm, 5-µm particles; Mobile Phase A: water with 20-mM ammonium acetate; Mobile Phase B: 95:5 acetonitrile:water with 20-mM ammonium acetate; Gradient: 25-95% B over 20 minutes, then a 5-minute hold at 100% B; Flow: 20 mL/min. Fractions containing the desired product were combined and dried via centrifugal evaporation. The material was then purified via prep HPLC using a chiral column. The yield of the first eluting isomer was 11.0 mg, and its purity was 100%. Two analytical LC/MS injections were used to determine the final purity. Injection 1 conditions: Column:Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. retention time: 3.08 min; M+H: 556. Injection 2 conditions: Column:Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. retention time: 4.08 min; M+H: 556. Proton NMR was acquired in deuterated DMSO.

Example 15

First eluting isolate NMR: $^1$H NMR (500 MHz, DMSO-$d_6$) δ 9.43 (s, 1H), 8.76 (s, 1H), 8.49-8.44 (m, 1H), 8.06 (dd, J=9.0, 5.3 Hz, 2H), 7.95-7.88 (m, 2H), 7.82 (s, 1H), 7.62-7.57 (m, 1H), 7.55-7.50 (m, 1H), 7.40 (t, J=8.9 Hz, 2H), 2.91-2.87 (m, 1H), 2.81 (d, J=4.6 Hz, 3H), 1.83-1.74 (m, 1H), 1.70 (s, 6H), 1.57-1.46 (m, 1H), 1.19 (d, J=6.7 Hz, 3H), 0.65 (t, J=7.3 Hz, 3H). The yield of the second eluting isomer was 10.8 mg, and its purity was 100%. Two analytical LC/MS injections were used to determine the final purity. Injection 1 conditions: Column:Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. retention time: 3.08 min; M+H: 556. Injection 2 conditions: Column:Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. retention time: 4.08 min; M+H: 556 Proton NMR was acquired in deuterated DMSO.

Example 16

Second eluting isolate NMR: $^1$H NMR (500 MHz, DMSO-$d_6$) δ 9.43 (s, 1H), 8.76 (s, 1H), 8.50-8.44 (m, 1H), 8.06 (dd, J=8.4, 5.6 Hz, 2H), 7.96-7.89 (m, 2H), 7.82 (s, 1H), 7.62-7.57 (m, 1H), 7.53 (d, J=7.6 Hz, 1H), 7.40 (t, J=8.9 Hz, 2H), 2.92-2.89 (m, 1H), 2.81 (d, J=4.6 Hz, 3H), 1.83-1.75 (m, 1H), 1.70 (s, 6H), 1.53 (dt, J=13.6, 6.6 Hz, 1H), 1.19 (d, J=6.7 Hz, 3H), 0.65 (t, J=7.3 Hz, 3H).

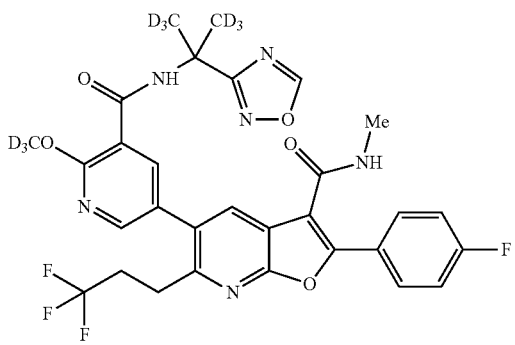

5-[2-(4-fluorophenyl)-3-(methylcarbamoyl)-6-(3,3,3-trifluoropropyl)furo[2,3-b]pyridin-5-yl]-2-($^2$H$_3$)methoxy-N-[2-(1,2,4-oxadiazol-3-yl)($^2$H$_6$)propan-2-yl]pyridine-3-carboxamide 2-(3H-[1,2,3]triazolo[4,5-b]pyridin-3-yl)-1,1,3,3-tetramethylisouronium hexafluorophosphate(V) (71.2 mg, 0.187 mmol) was added to stirring solution of 5-[2-(4-fluorophenyl)-3-(methylcarbamoyl)-6-(3,3,3-trifluoropropyl)furo[2,3-b]pyridin-5-yl]-2-($^2$H$_3$)methoxypyridine-3-carboxylic acid (65 mg, 0.13 mmol), N-ethyl-N-isopropylpropan-2-amine (65 µl, 0.38 mmol) and 2-(1,2,4-oxadiazol-3-yl)($^2$H$_6$)propan-2-amine hydrochloride (23.3 mg, 0.137 mmol) in DMF (1.2 ml) at rt. The mixture was allowed to stir at rt for 1 h. The mixture was then diluted with EtOAc and washed with 1M HCl, and sat NaCl. The organic phase was concentrated and absorbed onto Celite and was purified on silica gel (Biotage, EtOAc/DCM gradient, fraction collection at λ=254 nm) to give the expected product (68 mg, 0.11 mmol, 85% yield) consistent by LCMS and NMR, with sufficient purity by HPLC. LC-MS retention time: 1.86 min; m/z (MH+): 636. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode. $^1$H NMR (500 MHz, DMSO-d$_6$) δ 9.48 (s, 1H), 8.68 (s, 1H), 8.51-8.45 (m, 1H), 8.43 (d, J=2.5 Hz, 1H), 8.10 (d, J=2.4 Hz, 1H), 8.06 (dd, J=9.1, 5.4 Hz, 2H), 7.98 (s, 1H), 7.41 (t, J=8.9 Hz, 2H), 3.05-2.97 (m, 2H), 2.84-2.72 (m, 5H). Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=30 min, Stop time=32 min, Flow Rate=1 ml/min. Column:Waters Sunfire C-18, 4.6×150 mm, 3.5 mm, Rt=21.94 min, purity=100%; Column:Waters Xbridge Phenyl column 4.6×150 mm, 3.5 mm, Rt=18.34 min, purity=100%.

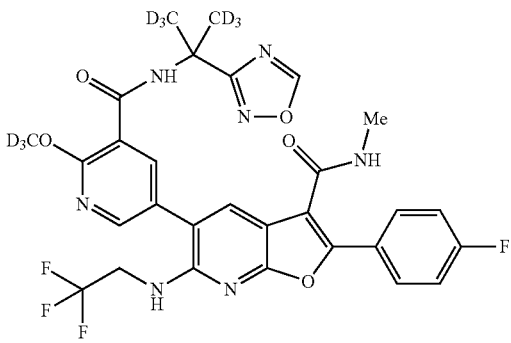

5-[2-(4-fluorophenyl)-3-(methylcarbamoyl)-6-[(2,2,2-trifluoroethyl)amino]furo[2,3-b]pyridin-5-yl]-2-($^2$H$_3$)methoxy-N-[2-(1,2,4-oxadiazol-3-yl)($^2$H$_6$)propan-2-yl]pyridine-3-carboxamide 2-(3H-[1,2,3]triazolo[4,5-b]pyridin-3-yl)-1,1,3,3-tetramethylisouronium hexafluorophosphate(V) (13 mg, 0.035 mmol) was added to stirring solution of 5-[2-(4-fluorophenyl)-3-(methylcarbamoyl)-6-[(2,2,2-trifluoroethyl)amino]furo[2,3-b]pyridin-5-yl]-2-($^2$H$_3$)methoxypyridine-3-carboxylic acid (12 mg, 0.023 mmol), N-ethyl-N-isopropylpropan-2-amine (0.012 ml, 0.069 mmol) and 2-(1,2,4-oxadiazol-3-yl)($^2$H$_6$)propan-2-amine hydrochloride (4.3 mg, 0.025 mmol) in DMF (1 ml) at rt. The mixture was allowed to stir at rt for 1 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammoniumacetate; Gradient: 35-75% B over 20 minutes, then a 5-minute hold at 100% B; Flow: 20 mL/min. Fractions containing the desired product were combined and dried via centrifugal evaporation. The yield of the product was 6.3 mg, and its estimated purity by LCMS analysis was 99%. Two analytical LC/MS injections were used to determine the final purity. Injection 1 conditions: Column:Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Rt: 2.74 min, M+H=637. Injection 2 conditions: Column:Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Rt: 3.77 min, M+H=637. Proton NMR was acquired in deuterated DMSO. $^1$H NMR (500 MHz, DMSO-d$_6$) δ 9.49 (s, 1H), 8.65 (s, 1H), 8.40-8.27 (m, 2H), 8.09 (s, 1H), 8.03-7.92 (m, 2H), 7.69 (s, 1H), 7.41-7.28 (m, 2H), 6.89-6.75 (m, 1H), 4.22-4.08 (m, 2H), 2.79 (d, J=4.3 Hz, 3H).

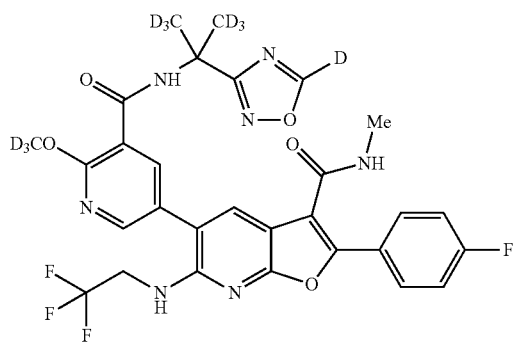

5-[2-(4-fluorophenyl)-3-(methylcarbamoyl)-6-[(2,2,2-trifluoroethyl)amino]furo[2,3-b]pyridin-5-yl]-2-($^2H_3$)methoxy-N-{2-[($^2H$)-1,2,4-oxadiazol-3-yl]($^2H_6$)propan-2-yl}pyridine-3-carboxamide 2-(3H-[1,2,3]triazolo[4,5-b]pyridin-3-yl)-1,1,3,3-tetramethylisouronium hexafluorophosphate(V) (16 mg, 0.043 mmol) was added to stirring solution of 5-[2-(4-fluorophenyl)-3-(methylcarbamoyl)-6-[(2,2,2-trifluoroethyl)amino]furo[2,3-b]pyridin-5-yl]-2-($^2H_3$)methoxypyridine-3-carboxylic acid (15 mg, 0.029 mmol), N-ethyl-N-isopropylpropan-2-amine (0.015 ml, 0.086 mmol) and 2-[($^2H$)-1,2,4-oxadiazol-3-yl]($^2H_6$)propan-2-amine hydrochloride (5.4 mg, 0.032 mmol) in DMF (1 ml) at rt. The mixture was allowed to stir at rt for 1 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-85% B over 20 minutes, then a 5-minute hold at 100% B; Flow: 20 mL/min. Fractions containing the desired product were combined and dried via centrifugal evaporation. The yield of the product was 15.1 mg, and its estimated purity by LCMS analysis was 99%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Rt: 1.97 min, M+H: 638. Injection 2 conditions: Column:Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Rt: 2.75 min, M+H=638 Proton NMR was acquired in deuterated DMSO. $^1$H NMR (500 MHz, DMSO-$d_6$) δ 8.66 (s, 1H), 8.37-8.32 (m, 2H), 8.09 (d, J=2.4 Hz, 1H), 7.97 (dd, J=8.5, 5.5 Hz, 2H), 7.69 (s, 1H), 7.34 (t, J=8.9 Hz, 2H), 6.86-6.77 (m, 1H), 4.22-4.09 (m, 2H), 2.79 (d, J=4.6 Hz, 3H).

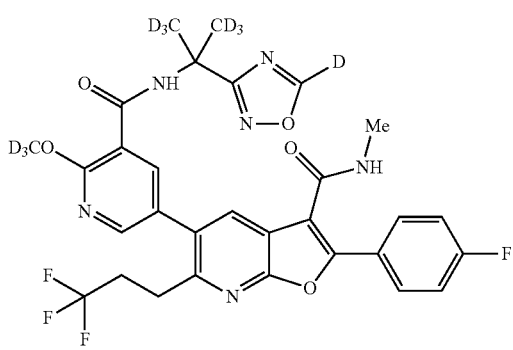

5-[2-(4-fluorophenyl)-3-(methylcarbamoyl)-6-(3,3,3-trifluoropropyl)furo[2,3-b]pyridin-5-yl]-2-($^2H_3$)methoxy-N-[2-[($^2H$)-1,2,4-oxadiazol-3-yl]($^2H_6$)propan-2-yl]pyridine-3-carboxamide 2-(3H-[1,2,3]triazolo[4,5-b]pyridin-3-yl)-1,1,3,3-tetramethylisouronium hexafluorophosphate(V) (16 mg, 0.043 mmol) was added to stirring solution of 5-[2-(4-fluorophenyl)-3-(methylcarbamoyl)-6-(3,3,3-trifluoropropyl)furo[2,3-b]pyridin-5-yl]-2-($^2H_3$)methoxypyridine-3-carboxylic acid (15 mg, 0.029 mmol), N-ethyl-N-isopropylpropan-2-amine (0.015 ml, 0.086 mmol) and 2-[($^2H$)-1,2,4-oxadiazol-3-yl]($^2H_6$)propan-2-amine hydrochloride (5.4 mg, 0.032 mmol) in DMF (1 ml) at rt. The mixture was allowed to stir at rt for 1 h. The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 30 minutes, then a 7-minute hold at 100% B; Flow: 20 mL/min. Fractions containing the desired product were combined and dried via centrifugal evaporation. The yield of the product was 11.9 mg, and its estimated purity by LCMS analysis was 99%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Rt: 2.16 min, M+H: 637. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Rt: 2.98, M+H: =637. Proton NMR was acquired in deuterated DMSO. $^1$H NMR (500 MHz, DMSO-$d_6$) δ 8.69 (s, 1H), 8.52-8.46 (m, 1H), 8.43 (d, J=2.4 Hz, 1H), 8.10 (d, J=2.4 Hz, 1H), 8.05 (dd, J=8.9, 5.5 Hz, 2H), 7.98 (s, 1H), 7.41 (t, J=8.9 Hz, 2H), 3.05-2.97 (m, 2H), 2.85-2.71 (m, 5H).

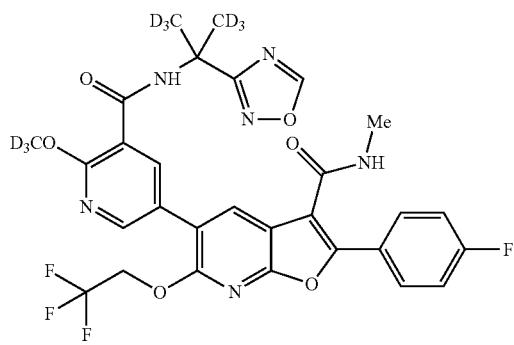

5-[2-(4-fluorophenyl)-3-(methylcarbamoyl)-6-(2,2,2-trifluoroethoxy)furo[2,3-b]pyridin-5-yl]-2-($^2$H$_3$)methoxy-N-[2-(1,2,4-oxadiazol-3-yl)($^2$H$_6$)propan-2-yl]pyridine-3-carboxamide 2-(3H-[1,2,3]triazolo[4,5-b]pyridin-3-yl)-1,1,3,3-tetramethylisouronium hexafluorophosphate(V) (16 mg, 0.043 mmol) was added to stirring solution of 5-[2-(4-fluorophenyl)-3-(methylcarbamoyl)-6-(2,2,2-trifluoroethoxy)furo[2,3-b]pyridin-5-yl]-2-($^2$H$_3$)methoxypyridine-3-carboxylic acid (15 mg, 0.029 mmol), N-ethyl-N-isopropylpropan-2-amine (15 μl, 0.086 mmol) and 2-(1,2,4-oxadiazol-3-yl)($^2$H$_6$)propan-2-amine hydrochloride (5.4 mg, 0.032 mmol) in DMF (0.5 ml) at rt. The mixture was allowed to stir at rt for 1 h. The crude material was purified via preparative LC/MS with the following conditions: Column: XBridge C18, 19×200 mm, 5 μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 20 minutes, then a 7-minute hold at 100% B; Flow: 20 mL/min. Fractions containing the desired product were combined and dried via centrifugal evaporation. The yield of the product was 6.5 mg, and its estimated purity by LCMS analysis was 97%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Rt: 2.17 min. M+H=638. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Rt: 3.03 min. M+H=638. Proton NMR was acquired in deuterated DMSO. $^1$H NMR (500 MHz, DMSO-d$_6$) δ 9.45 (s, 1H), 8.65 (s, 1H), 8.55-8.45 (m, 2H), 8.26 (s, 1H), 8.16 (s, 1H), 8.02-7.93 (m, 2H), 7.37 (t, J=8.9 Hz, 2H), 5.10 (q, J=8.7 Hz, 2H), 2.83 (d, J=4.6 Hz, 3H).

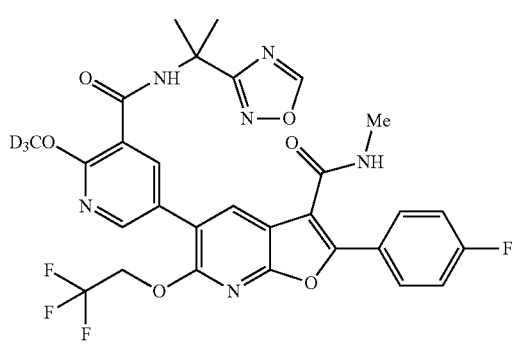

5-[2-(4-fluorophenyl)-3-(methylcarbamoyl)-6-(2,2,2-trifluoroethoxy)furo[2,3-b]pyridin-5-yl]-2-($^2$H$_3$)methoxy-N-[2-(1,2,4-oxadiazol-3-yl)propan-2-yl]pyridine-3-carboxamide 2-(3H-[1,2,3]triazolo[4,5-b]pyridin-3-yl)-1,1,3,3-tetramethylisouronium hexafluorophosphate(V) (16 mg, 0.043 mmol) was added to stirring solution of 5-[2-(4-fluorophenyl)-3-(methylcarbamoyl)-6-(2,2,2-trifluoroethoxy)furo[2,3-b]pyridin-5-yl]-2-($^2$H$_3$)methoxypyridine-3-carboxylic acid (15 mg, 0.029 mmol), N-ethyl-N-isopropylpropan-2-amine (15 μl, 0.086 mmol) and 2-(1,2,4-oxadiazol-3-yl)propan-2-amine hydrochloride (5.2 mg, 0.032 mmol) in DMF (0.5 ml) at rt. The mixture was allowed to stir at rt for 1 h. The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 20 minutes, then a 5-minute hold at 100% B; Flow: 20 mL/min. Fractions containing the desired product were combined and dried via centrifugal evaporation. The yield of the product was 7.9 mg, and its estimated purity by LCMS analysis was 97%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Rt: 2.18 min; M+H=632. Injection 2 conditions: Column:Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Rt: 3.04 min; M+H=632. Proton NMR was acquired in deuterated DMSO. $^1$H NMR (500 MHz, DMSO-d$_6$) δ 9.48 (s, 1H), 8.66 (s, 1H), 8.55 (s, 1H), 8.52-8.46 (m, 1H), 8.27 (s, 1H), 8.19 (s, 1H), 8.05-7.98 (m, 2H), 7.39 (t, J=8.5 Hz, 2H), 5.12 (q, J=9.0 Hz, 2H), 2.84 (d, J=4.3 Hz, 3H), 1.73 (s, 6H).

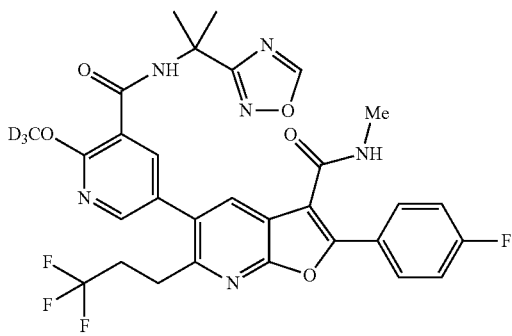

5-[2-(4-fluorophenyl)-3-(methylcarbamoyl)-6-(3,3,3-trifluoropropyl)furo[2,3-b]pyridin-5-yl]-2-($^2H_3$)methoxy-N-[2-(1,2,4-oxadiazol-3-yl)propan-2-yl]pyridine-3-carboxamide N-ethyl-N-isopropylpropan-2-amine (18 μA, 0.108 mmol) was added to stirring solution of 5-[2-(4-fluorophenyl)-3-(methylcarbamoyl)-6-(3,3,3-trifluoropropyl)furo[2,3-b]pyridin-5-yl]-2-($^2H_3$)methoxypyridine-3-carboxylic acid (7.0 mg, 0.013 mmol), 2-(3H-[1,2,3]triazolo[4,5-b]pyridin-3-yl)-1,1,3,3-tetramethylisouronium hexafluorophosphate(V) (7.7 mg, 0.020 mmol) and 2-(1,2,4-oxadiazol-3-yl)propan-2-amine hydrochloride (3.3 mg, 0.020 mmol) in DMF (1) at rt. The mixture was allowed to stir at rt for 1 h. LCMS shows complete reaction. The reaction mixture was filtered and then purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-90% B over 15 minutes, then a 5-minute hold at 100% B; Flow: 20 mL/min. Fractions containing the desired product were combined and dried via centrifugal evaporation. The yield of the product was 3.1 mg, and its estimated purity by LCMS analysis was 97%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Rt: 2.96 min, M+H=630. Injection 2 conditions: Column:Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Rt: 4.08 min, M+H=630. Proton NMR was acquired in deuterated methanol. $^1H$ NMR (500 MHz, DMSO-$d_6$) δ 9.48 (s, 1H), 8.70 (s, 1H), 8.49 (d, J=4.3 Hz, 1H), 8.43 (d, J=2.1 Hz, 1H), 8.10 (d, J=2.1 Hz, 1H), 8.06 (dd, J=8.4, 5.6 Hz, 2H), 7.98 (s, 1H), 7.41 (t, J=8.7 Hz, 2H), 3.01 (t, J=7.8 Hz, 2H), 2.81 (d, J=4.3 Hz, 3H), 2.80-2.69 (m, 2H), 1.73 (s, 6H).

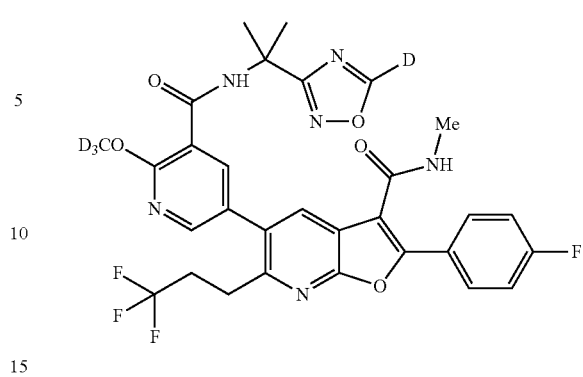

5-[2-(4-fluorophenyl)-3-(methylcarbamoyl)-6-(3,3,3-trifluoropropyl)furo[2,3-b]pyridin-5-yl]-2-($^2H_3$)methoxy-N-[2-[($^2H$)-1,2,4-oxadiazol-3-yl]propan-2-yl]pyridine-3-carboxamide 2-(3H-[1,2,3]triazolo[4,5-b]pyridin-3-yl)-1,1,3,3-tetramethylisouronium hexafluorophosphate(V) (16 mg, 0.043 mmol) was added to stirring solution of 5-[2-(4-fluorophenyl)-3-(methylcarbamoyl)-6-(3,3,3-trifluoropropyl)furo[2,3-b]pyridin-5-yl]-2-($^2H_3$)methoxypyridine-3-carboxylic acid (15 mg, 0.029 mmol), N-ethyl-N-isopropylpropan-2-amine (0.015 ml, 0.086 mmol) and 2-[($^2H$)-1,2,4-oxadiazol-3-yl]propan-2-amine hydrochloride (5.2 mg, 0.032 mmol) in DMF (1 ml) at rt. The mixture was allowed to stir at rt for 1 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 13.2 mg, and its estimated purity by LCMS analysis was 99%. Two analytical LC/MS injections were used to determine the final purity. Injection 1 conditions: Column:Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Rt: 2.17 min; M+H=631. Injection 2 conditions: Column:Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Rt: 3.01 min; M+H=631. Proton NMR was acquired in deuterated DMSO. $^1H$ NMR (500 MHz, DMSO-$d_6$) δ 8.70 (s, 1H), 8.53-8.45 (m, 1H), 8.43 (s, 1H), 8.10 (s, 1H), 8.07-8.01 (m, 2H), 7.98 (s, 1H), 7.41 (t, J=8.7 Hz, 2H), 3.05-2.96 (m, 2H), 2.85-2.71 (m, 5H), 1.73 (s, 6H).

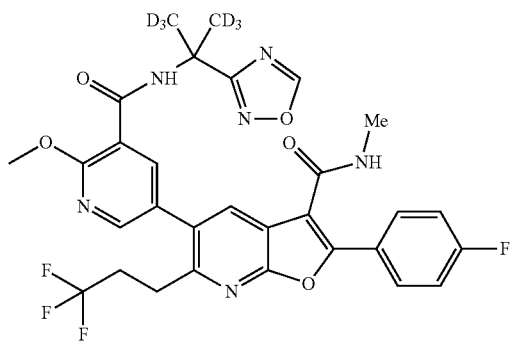 [SMILES: [2H]C([2H])([2H])C(NC(=O)c1cc(-c2cc3c(C(=O)NC)c(-c4ccc(F)cc4)oc3nc2CCC(F)(F)F)cnc1OC)(c1ncon1)C([2H])([2H])[2H]]

5-[2-(4-fluorophenyl)-3-(methylcarbamoyl)-6-(3,3,3-trifluoropropyl)furo[2,3-b]pyridin-5-yl]-2-methoxy-N-[2-(1,2,4-oxadiazol-3-yl)($^2$H$_6$)propan-2-yl]pyridine-3-carboxamide

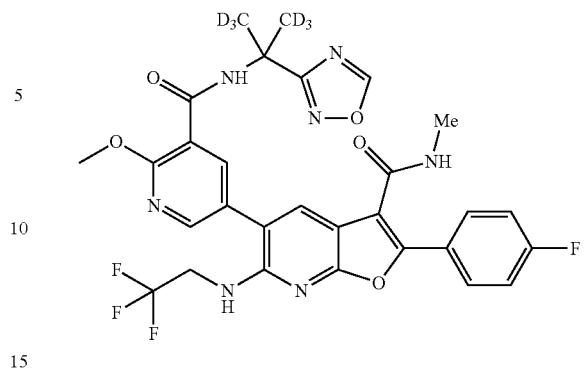

5-[2-(4-fluorophenyl)-3-(methylcarbamoyl)-6-[(2,2,2-trifluoroethyl)amino]furo[2,3-b]pyridin-5-yl]-2-methoxy-N-[2-(1,2,4-oxadiazol-3-yl)($^2$H$_6$)propan-2-yl]pyridine-3-carboxamide 2-(3H-[1,2,3]triazolo[4,5-b]pyridin-3-yl)-1,1,3,3-tetramethylisouronium hexafluorophosphate(V) (22 mg, 0.058 mmol) was added to stirring solution of 5-(2-(4-fluorophenyl)-3-(methylcarbamoyl)-6-(3,3,3-trifluoropropyl)furo[2,3-b]pyridin-5-yl)-2-methoxynicotinic acid (20 mg, 0.039 mmol), N-ethyl-N-isopropylpropan-2-amine (0.020 ml, 0.12 mmol) and 2-(1,2,4-oxadiazol-3-yl)($^2$H$_6$)propan-2-amine hydrochloride (7.2 mg, 0.043 mmol) in DMF (1 ml) at rt. The mixture was allowed to stir at rt for 1 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 7-minute hold at 100% B; Flow: 20 mL/min. Fractions containing the desired product were combined and dried via centrifugal evaporation. The yield of the product was 17.9 mg, and its estimated purity by LCMS analysis was 100%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Rt: 3.33 min, M+H=633. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Rt: 4.34 min, M+H=633. Proton NMR was acquired in deuterated DMSO. $^1$H NMR (500 MHz, DMSO-d$_6$) δ 9.48 (s, 1H), 8.69 (s, 1H), 8.53-8.45 (m, 1H), 8.43 (s, 1H), 8.13-8.02 (m, 3H), 7.98 (s, 1H), 7.41 (t, J=8.1 Hz, 2H), 4.10 (s, 3H), 3.06-2.98 (m, 2H), 2.86-2.71 (m, 5H).

2-(3H-[1,2,3]triazolo[4,5-b]pyridin-3-yl)-1,1,3,3-tetramethylisouronium hexafluorophosphate(V) (13 mg, 0.035 mmol) was added to stirring solution of 5-(2-(4-fluorophenyl)-3-(methylcarbamoyl)-6-((2,2,2-trifluoroethyl)amino)furo[2,3-b]pyridin-5-yl)-2-methoxynicotinic acid (12 mg, 0.023 mmol), N-ethyl-N-isopropylpropan-2-amine (0.012 ml, 0.069 mmol) and 2-(1,2,4-oxadiazol-3-yl)($^2$H$_6$)propan-2-amine hydrochloride (4.3 mg, 0.025 mmol) in DMF (1 ml) at rt. The mixture was allowed to stir at rt for 1 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 20 minutes, then a 5-minute hold at 100% B; Flow: 20 mL/min. Fractions containing the desired product were combined and dried via centrifugal evaporation. The yield of the product was 5.2 mg, and its estimated purity by LCMS analysis was 100%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Rt: 2.74 min, M+H=634. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Rt: 3.78 min, M+H=634. Proton NMR was acquired in deuterated DMSO. $^1$H NMR (500 MHz, DMSO-d$_6$) δ 9.49 (s, 1H), 8.65 (s, 1H), 8.39-8.30 (m, 2H), 8.09 (s, 1H), 8.03-7.91 (m, 2H), 7.69 (s, 1H), 7.34 (t, J=8.9 Hz, 2H), 6.87-6.76 (m, 1H), 4.20-4.05 (m, 5H), 2.79 (d, J=4.3 Hz, 3H).

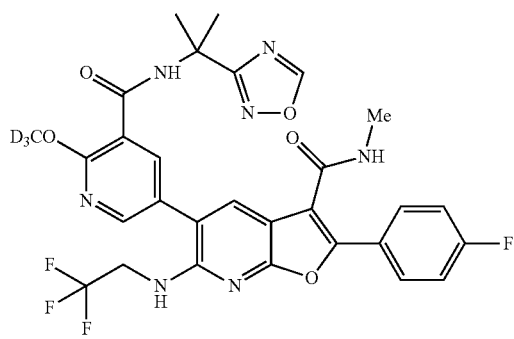

5-[2-(4-fluorophenyl)-3-(methylcarbamoyl)-6-[(2,2,2-trifluoroethyl)amino]furo[2,3-b]pyridin-5-yl]-2-($^2$H$_3$)methoxy-N-[2-(1,2,4-oxadiazol-3-yl)propan-2-yl]pyridine-3-carboxamide

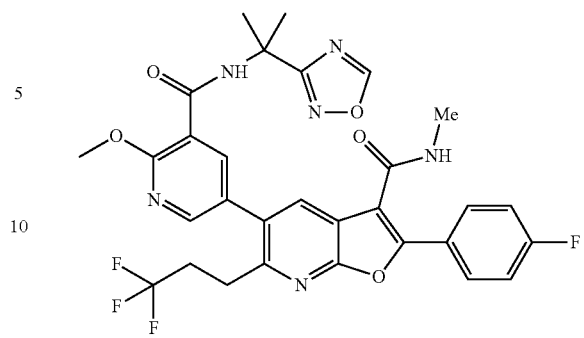

5-[2-(4-fluorophenyl)-3-(methylcarbamoyl)-6-(3,3,3-trifluoropropyl)furo[2,3-b]pyridin-5-yl]-2-methoxy-N-[2-(1,2,4-oxadiazol-3-yl)propan-2-yl]pyridine-3-carboxamide N-ethyl-N-isopropylpropan-2-amine (32 µl, 0.18 mmol) was added to stirring solution of 5-[2-(4-fluorophenyl)-3-(methylcarbamoyl)-6-[(2,2,2-trifluoroethyl)amino]furo[2,3-b]pyridin-5-yl]-2-($^2$H$_3$)methoxypyridine-3-carboxylic acid (12 mg, 0.023 mmol), 2-(3H-[1,2,3]triazolo[4,5-b]pyridin-3-yl)-1,1,3,3-tetramethylisouronium hexafluorophosphate(V) (13 mg, 0.035 mmol) and 2-(1,2,4-oxadiazol-3-yl)propan-2-amine hydrochloride (7.5 mg, 0.046 mmol) in DMF (1) at rt. The mixture was allowed to stir at rt for 1 h. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. The yield of the product was 8.5 mg, and its estimated purity by LCMS analysis was 100%. Two analytical LC/MS injections were used to determine the final purity. Injection 1 conditions: Column:Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Rt: 2.90 min, M–H=629. Injection 2 conditions: Column:Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Rt: 3.97 min, M–H=629. Proton NMR was acquired in deuterated DMSO. $^1$H NMR (500 MHz, DMSO-d$_6$) δ 9.49 (s, 1H), 8.66 (s, 1H), 8.34 (br. s., 2H), 8.09 (s, 1H), 8.04-7.92 (m, 2H), 7.69 (s, 1H), 7.34 (t, J=8.4 Hz, 2H), 6.82 (br. s., 1H), 4.21-4.09 (m, 2H), 2.79 (d, J=4.0 Hz, 3H), 1.74 (s, 6H).

N-ethyl-N-isopropylpropan-2-amine (67 µl, 0.39 mmol) was added to stirring solution of 5-(2-(4-fluorophenyl)-3-(methylcarbamoyl)-6-(3,3,3-trifluoropropyl)furo[2,3-b]pyridin-5-yl)-2-methoxynicotinic acid (25 mg, 0.048 mmol), 2-(3H-[1,2,3]triazolo[4,5-b]pyridin-3-yl)-1,1,3,3-tetramethylisouronium hexafluorophosphate(V) (28 mg, 0.072 mmol) and 2-(1,2,4-oxadiazol-3-yl)propan-2-amine hydrochloride (7.9 mg, 0.048 mmol) in DMF (1) at rt. The mixture was allowed to stir at rt for 1 h. LCMS shows complete reaction. The solution was filtered and then the crude material was purified via preparative LC/MS with the following conditions: Column:Waters XBridge C18, 19×200 mm, 5-µm particles; Mobile Phase A: water with 20-mM ammonium acetate; Mobile Phase B: 95:5 acetonitrile:water with 20-mM ammonium acetate; Gradient: 20-100% B over 15 minutes, then a 5-minute hold at 100% B; Flow: 20 mL/min. Fractions containing the desired product were combined and dried via centrifugal evaporation. The yield of the product was 26.2 mg, and its estimated purity by LCMS analysis was 96%. Two analytical LC/MS injections were used to determine the final purity. Injection 1 conditions: Column:Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Rt: 3.14 min, M+H=627. Injection 2 conditions: Column:Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Rt: 4.05 min, M+H=627. Proton NMR was acquired in deuterated DMSO. $^1$H NMR (500 MHz, DMSO-d$_6$) δ 9.48 (s, 1H), 8.70 (s, 1H), 8.49 (d, J=4.6 Hz, 1H), 8.43 (d, J=2.4 Hz, 1H), 8.10 (d, J=2.4 Hz, 1H), 8.08-8.02 (m, 2H), 7.98 (s, 1H), 7.41 (t, J=8.9 Hz, 2H), 4.10 (s, 3H), 3.04-2.98 (m, 2H), 2.81 (d, J=4.6 Hz, 3H), 2.80-2.74 (m, 2H), 1.73 (s, 6H).

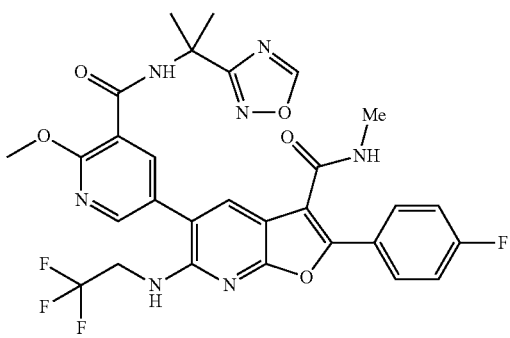 [SMILES: CNC(=O)c1c(-c2ccc(F)cc2)oc2nc(NCC(F)(F)F)c(-c3cnc(OC)c(C(=O)NC(C)(C)c4ncon4)c3)cc12]

5-[2-(4-fluorophenyl)-3-(methylcarbamoyl)-6-[(2,2,2-trifluoroethyl)amino]furo[2,3-b]pyridin-5-yl]-2-methoxy-N-[2-(1,2,4-oxadiazol-3-yl)propan-2-yl]pyridine-3-carboxamide

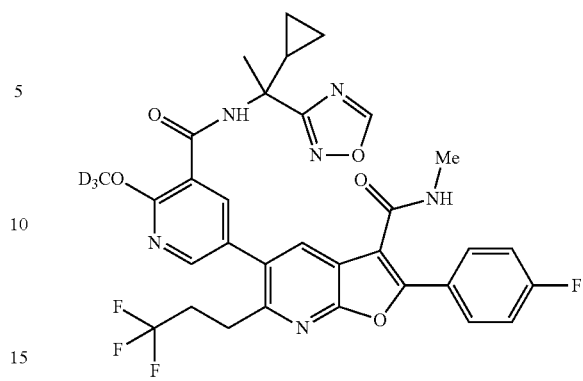

N-[1-cyclopropyl-1-(1,2,4-oxadiazol-3-yl)ethyl]-5-[2-(4-fluorophenyl)-3-(methylcarbamoyl)-6-(3,3,3-trifluoropropyl)furo[2,3-b]pyridin-5-yl]-2-($^2H_3$)methoxypyridine-3-carboxamide N-ethyl-N-isopropylpropan-2-amine (67 µl, 0.39 mmol) was added to stirring solution of 5-(2-(4-fluorophenyl)-3-(methylcarbamoyl)-6-((2,2,2-trifluoroethyl)amino)furo[2,3-b]pyridin-5-yl)-2-methoxynicotinic acid (25 mg, 0.048 mmol), 2-(3H-[1,2,3]triazolo[4,5-b]pyridin-3-yl)-1,1,3,3-tetramethylisouronium hexafluorophosphate(V) (28 mg, 0.072 mmol) and 2-(1,2,4-oxadiazol-3-yl)propan-2-amine hydrochloride (7.9 mg, 0.048 mmol) in DMF (1) at rt. The mixture was allowed to stir at rt for 1 h. LCMS shows complete reaction. The solution was filtered and then the crude material was purified via preparative LC/MS with the following conditions: Column: Waters XBridge C18, 19×200 mm, 5-µm particles; Mobile Phase A: water with 20-mM ammonium acetate; Mobile Phase B: 95:5 acetonitrile:water with 20-mM ammonium acetate; Gradient: 25-90% B over 25 minutes, then a 5-minute hold at 100% B; Flow: 20 mL/min. Fractions containing the desired product were combined and dried via centrifugal evaporation. The yield of the product was 7.6 mg, and its estimated purity by LCMS analysis was 94%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Rt: 2.95 min, M+H=628. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Rt: 3.86 min, M+H=628. Proton NMR was acquired in deuterated DMSO. $^1$H NMR (500 MHz, DMSO-$d_6$) δ 9.49 (s, 1H), 8.66 (s, 1H), 8.34 (s, 2H), 8.09 (s, 1H), 8.00-7.94 (m, 2H), 7.69 (s, 1H), 7.34 (t, J=8.9 Hz, 2H), 6.82 (t, J=6.3 Hz, 1H), 4.19-4.12 (m, 2H), 4.10 (s, 3H), 2.79 (d, J=4.3 Hz, 3H), 1.74 (s, 6H).

2-(3H-[1,2,3]triazolo[4,5-b]pyridin-3-yl)-1,1,3,3-tetramethylisouronium hexafluorophosphate(V) (16 mg, 0.043 mmol) was added to stirring solution of 5-[2-(4-fluorophenyl)-3-(methylcarbamoyl)-6-(3,3,3-trifluoropropyl)furo[2,3-b]pyridin-5-yl]-2-($^2H_3$)methoxypyridine-3-carboxylic acid (15 mg, 0.029 mmol), N-ethyl-N-isopropylpropan-2-amine (0.015 ml, 0.086 mmol) and 1-cyclopropyl-1-(1,2,4-oxadiazol-3-yl)ethanamine hydrochloride (prepared above) (6.0 mg, 0.032 mmol) in DMF (1 ml) at rt. The mixture was allowed to stir at rt for 1 h. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 7-minute hold at 100% B; Flow: 20 mL/min. Fractions containing the desired product were combined and dried via centrifugal evaporation. The yield of the product was 11.6 mg, and its estimated purity by LCMS analysis was 100%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Rt: 2.27 min, M+H=656. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Rt: 3.09 min, M+H=656. Proton NMR was acquired in deuterated DMSO. $^1$H NMR (500 MHz, DMSO-$d_6$) δ 9.47 (s, 1H), 8.68 (s, 1H), 8.52-8.47 (m, 1H), 8.45 (s, 1H), 8.15 (s, 1H), 8.11-8.02 (m, 2H), 7.98 (s, 1H), 7.41 (t, J=8.5 Hz, 2H), 3.06-2.96 (m, 2H), 2.84-2.72 (m, 5H), 1.70 (s, 3H), 1.64-1.54 (m, 1H), 0.62-0.49 (m, 2H), 0.48-0.43 (m, 1H), 0.42-0.35 (m, 1H).

Biological Methods

HCV NS5B RdRp Cloning, Expression, and Purification.

The cDNA encoding NS5B proteins of HCV genotype 1b (Con1), a genotype 1b variant with amino acid 316 mutated from cysteine to asparagine, and genotype 2a (JFH-1), were cloned into the pET21a expression vector. Each untagged protein was expressed with an 18 amino acid C-terminal truncation to enhance the solubility. The *E. coli* competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/mL lysozyme, 10 mM $MgCl_2$, 15 ug/mL deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 µm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease I, $MgCl_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

HCV NS5B RdRp Enzyme Assay.

An on-bead solid phase homogeneous assay was used in a 384-well format to assess NS5B inhibitors (Wang Y-K, Rigat K, Roberts S, and Gao M (2006) Anal Biochem, 359: 106-111). The biotinylated oligo $dT_{12}$ primer was captured on streptavidin-coupled imaging beads (GE, RPNQ0261) by mixing primer and beads in 1× buffer and incubating at room temperature for three hours. Unbound primer was removed after centrifugation. The primer-bound beads were resuspended in 3× reaction mix (20 mM Hepes buffer, pH 7.5, dT primer coupled beads, poly A template, $^3$H-UTP, and RNAse inhibitor (Promega N2515)). Compounds were serially diluted 1:3 in DMSO and aliquoted into assay plates. Equal volumes (5 µL) of water, 3× reaction mix, and enzyme in 3× assay buffer (60 mM Hepes buffer, pH 7.5, 7.5 mM $MgCl_2$, 7.5 mM KCl, 3 mM DTT, 0.03 mg/mL BSA, 6% glycerol) were added to the diluted compound on the assay plate. Final concentration of components in 384-well assay: 0.36 nM template, 15 nM primer, 0.29 µM $^3$H-UTP (0.3 KO, 1.6 U/µL RNAse inhibitor, 7 nM NS5B enzyme, 0.01 mg/mL BSA, 1 mM DTT, and 0.33 µg/µL beads, 20 mM Hepes buffer, pH 7.5, 2.5 mM $MgCl_2$, 2.5 mM KCl, and 0.1% DMSO.

Reactions were allowed to proceed for 24 hours at 30° C. and terminated by the addition of 50 mM EDTA (5 µL). After incubating for at least 15 minutes, plates were read on an Amersham LEADseeker multimodality imaging system.

$IC_{50}$ values for compounds were determined using ten different [I]. $IC_{50}$ values were calculated from the inhibition using the four-parameter logistic formula $y=A+((B-A)/(1+((C/x)\char`\^D)))$, where A and B denote minimal and maximal % inhibition, respectively, C is the $IC_{50}$, D is hill slope and x represents compound concentration.

Cell Lines.

The cell lines used to evaluate compounds consist of a human hepatocyte derived cell line (Huh-7) that constitutively expresses a genotype 1b (Con-1) HCV replicon or a genotype 1b (Con-1) HCV replicon with an asparagine replacing the cysteine at amino acid 316, or a genotype 2a (JFH-1) replicon, containing a *Renilla* luciferase reporter gene. These cells were maintained in Dulbecco's modified Eagle medium (DMEM) containing 10% FBS, 100 U/mL penicillin/streptomycin and 1.0 mg/mL G418.

HCV Replicon Luciferase Assay.

To evaluate compound efficacy, titrated compounds were transferred to sterile 384-well tissue culture treated plates, and the plates were seeded with HCV replicon cells (50 µL at a density of $2.4 \times 10^3$ cells/well) in DMEM containing 4% FBS (final DMSO concentration at 0.5%). After 3 days incubation at 37° C., cells were analyzed for *Renilla* Luciferase activity using the EnduRen substrate (Promega cat #E6485) according to the manufacturer's directions. Briefly, the EnduRen substrate was diluted in DMEM and then added to the plates to a final concentration of 7.5 µM. The plates were incubated for at least 1 h at 37° C. then read on a Viewlux Imager (PerkinElmer) using a luminescence program. The 50% effective concentration ($EC_{50}$) was calculated using the four-parameter logistic formula noted above.

To assess cytotoxicity of compounds, Cell Titer-Blue (Promega) was added to the EnduRen-containing plates and incubated for at least 4 h at 37° C. The fluorescence signal from each well was read using a Viewlux Imager. All $CC_{50}$ values were calculated using the four-parameter logistic formula.

1b replicon and enzyme data for compound I is reported in Table 2.

TABLE 2

| Example | Structure | EC$_{50}$, (μM) | IC$_{50}$ (μM) |
|---|---|---|---|
| Example 1 | 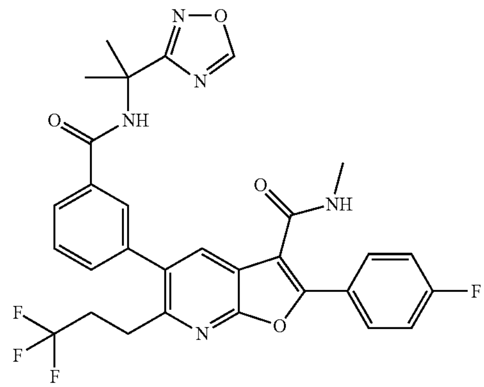 [SMILES: CNC(=O)c1c(-c2ccc(F)cc2)oc2nc(CCC(F)(F)F)c(-c3cccc(C(=O)NC(C)(C)c4ncon4)c3)cc12] | 3.02E−03 | 2.32E−03 |
| Example 2 | 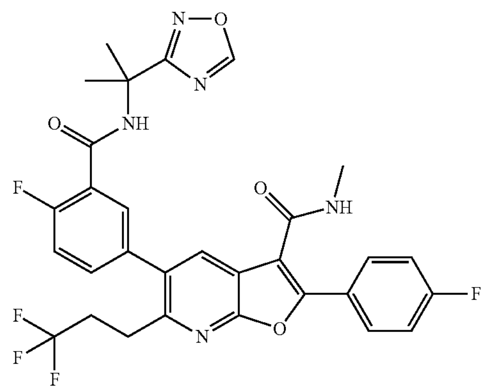 [SMILES: CNC(=O)c1c(-c2ccc(F)cc2)oc2nc(CCC(F)(F)F)c(-c3ccc(F)c(C(=O)NC(C)(C)c4ncon4)c3)cc12] | 4.03E−03 | N.D. |
| Example 3 | 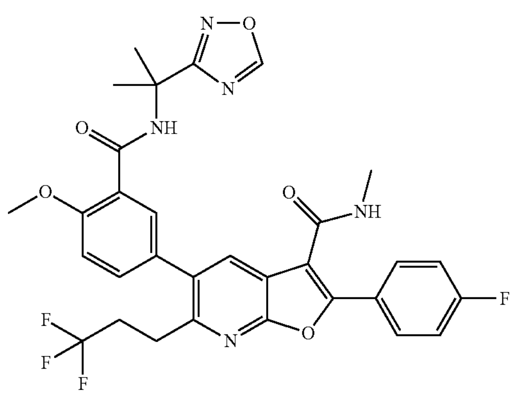 [SMILES: CNC(=O)c1c(-c2ccc(F)cc2)oc2nc(CCC(F)(F)F)c(-c3ccc(OC)c(C(=O)NC(C)(C)c4ncon4)c3)cc12] | 4.67E−03 | N.D. |
| Example 4 | 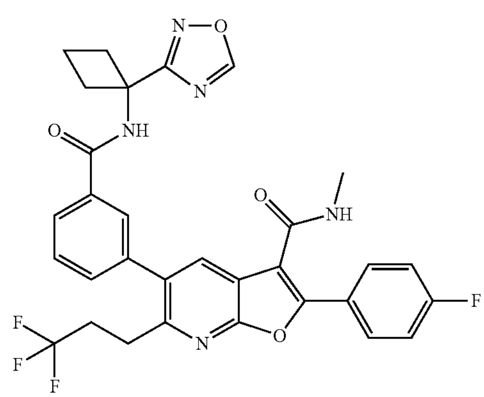 [SMILES: CNC(=O)c1c(-c2ccc(F)cc2)oc2nc(CCC(F)(F)F)c(-c3cccc(C(=O)NC4(c5ncon5)CCC4)c3)cc12] | 2.41E−03 | 2.05E−03 |

TABLE 2-continued

| Example | Structure | EC$_{50}$, (µM) | IC$_{50}$ (µM) |
|---|---|---|---|
| Example 5 | 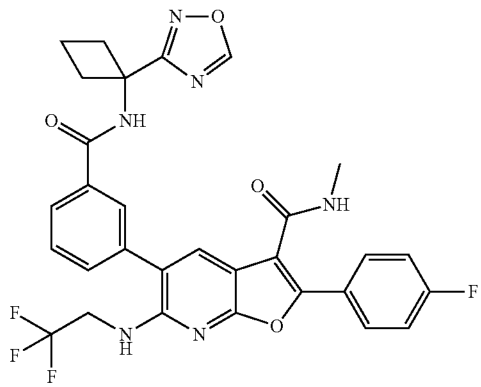 [SMILES: CNC(=O)c1c(-c2ccc(F)cc2)oc2nc(NCC(F)(F)F)c(-c3cccc(C(=O)NC4(c5ncon5)CCC4)c3)cc12] | 4.96E−03 | N.D. |
| Example 6 | 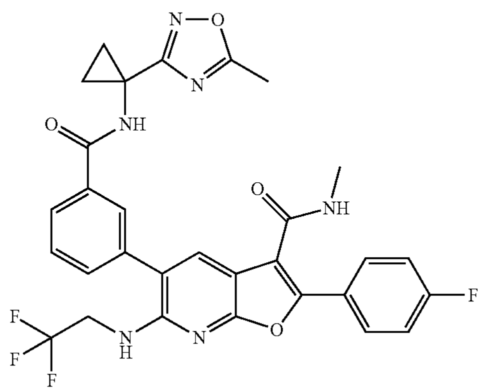 [SMILES: CNC(=O)c1c(-c2ccc(F)cc2)oc2nc(NCC(F)(F)F)c(-c3cccc(C(=O)NC4(c5noc(C)n5)CC4)c3)cc12] | 4.76E−03 | N.D. |
| Example 7 | 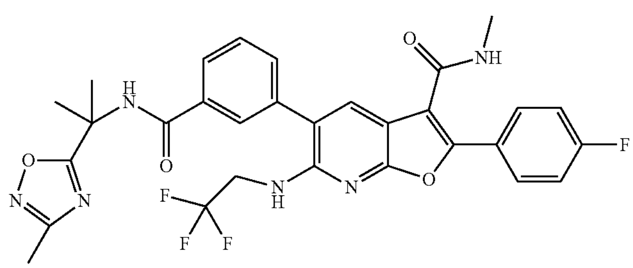 [SMILES: CNC(=O)c1c(-c2ccc(F)cc2)oc2nc(NCC(F)(F)F)c(-c3cccc(C(=O)NC(C)(C)c4nc(C)no4)c3)cc12] | 3.46E−03 | 4.13E−03 |
| Example 8 | 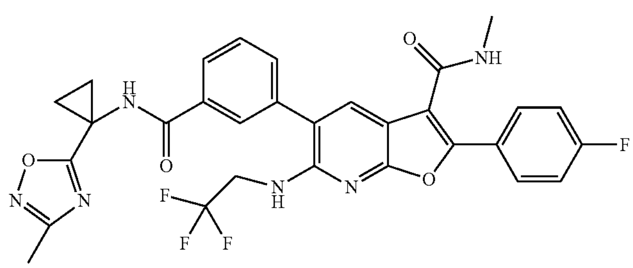 [SMILES: CNC(=O)c1c(-c2ccc(F)cc2)oc2nc(NCC(F)(F)F)c(-c3cccc(C(=O)NC4(c5nc(C)no5)CC4)c3)cc12] | 5.60E−03 | 4.80E−03 |
| Example 9 | 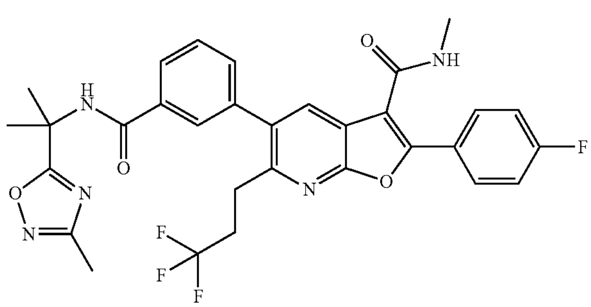 [SMILES: CNC(=O)c1c(-c2ccc(F)cc2)oc2nc(CCC(F)(F)F)c(-c3cccc(C(=O)NC(C)(C)c4nc(C)no4)c3)cc12] | 2.11E−03 | 2.87E−03 |

TABLE 2-continued
| Example | Structure | EC$_{50}$, (μM) | IC$_{50}$ (μM) |
|---------|-----------|-----------------|----------------|
| Example 10 | 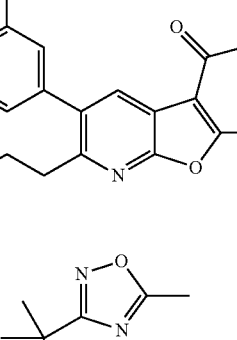 | 3.61E−03 | N.D. |
| Example 11 | 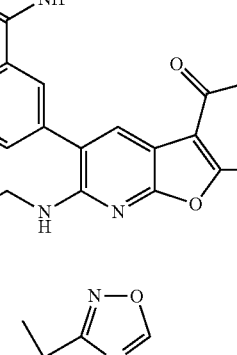 | 4.96E−03 | N.D. |
| Example 12 | 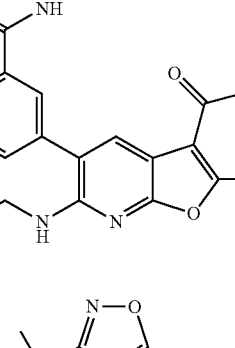 | 2.95E−03 | 9.25E−03 |
| Example 13 | 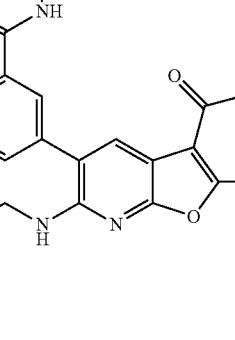 | 5.76E−03 | 3.42E−03 |

TABLE 2-continued

| Example | Structure | EC$_{50}$, (μM) | IC$_{50}$ (μM) |
|---|---|---|---|
| Example 14 | 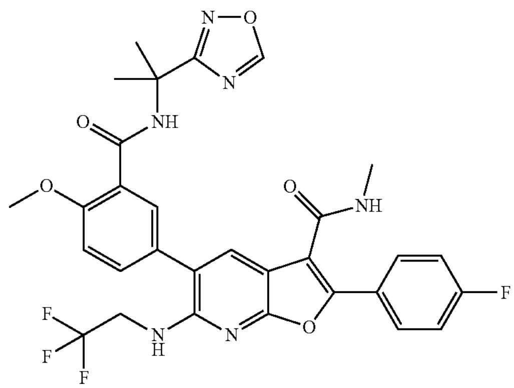 | 6.67E−03 | N.D. |
| Example 15 (fast eluting isomer) | 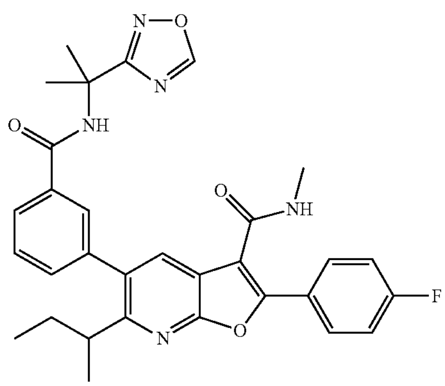 [SMILES: CCC(C)c1nc2oc(-c3ccc(F)cc3)c(C(=O)NC)c2cc1-c1cccc(C(=O)NC(C)(C)c2ncon2)c1] | 4.98E−03 | N.D. |
| Example 16 (slow eluting isomer) | 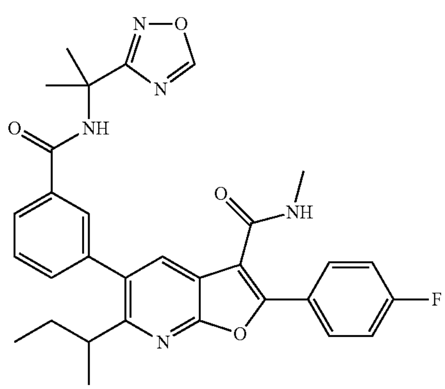 [SMILES: CCC(C)c1nc2oc(-c3ccc(F)cc3)c(C(=O)NC)c2cc1-c1cccc(C(=O)NC(C)(C)c2ncon2)c1] | 0.02 | N.D. |
| Example 17 | 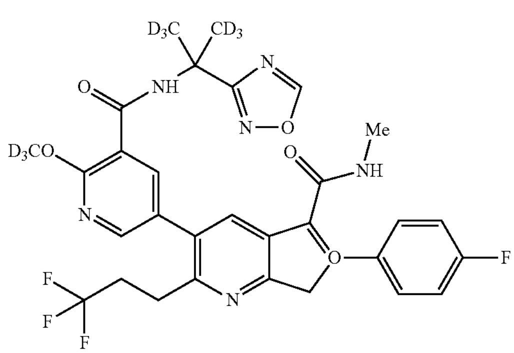 | 3.50E−03 | 2.40E−03 |

TABLE 2-continued
| Example | Structure | EC$_{50}$, (μM) | IC$_{50}$ (μM) |
|---|---|---|---|
| Example 18 | 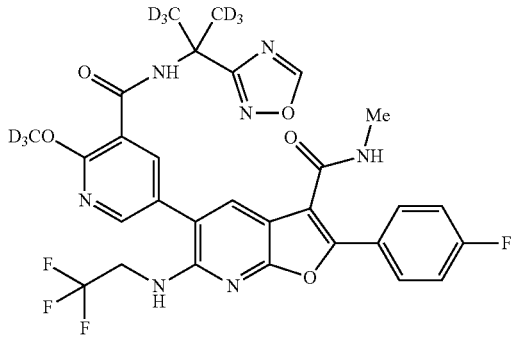 | 4.32E−03 | |
| Example 19 | 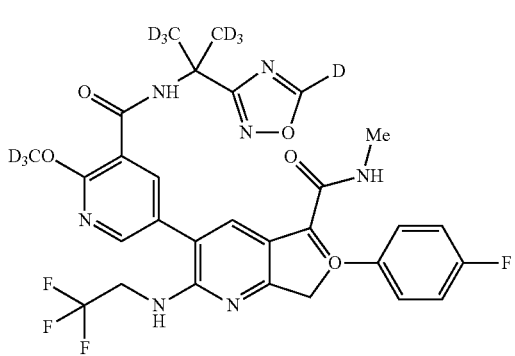 | 5.77E−03 | |
| Example 20 | 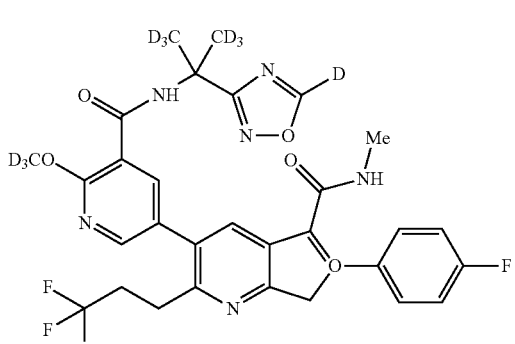 | 4.08E−03 | |
| Example 21 | 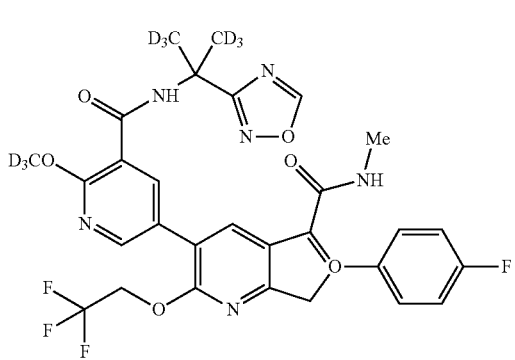 | 2.23E−03 | |

TABLE 2-continued

| Example | Structure | EC$_{50}$, (μM) | IC$_{50}$ (μM) |
|---|---|---|---|
| Example 22 | 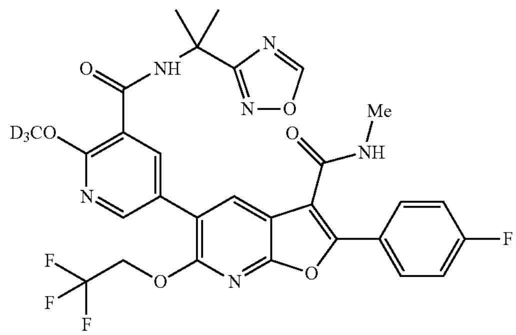 | | 1.70E-03 |
| Example 23 | 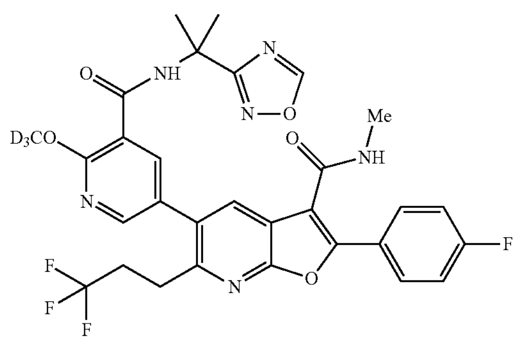 | | 4.24E-03 |
| Example 24 | 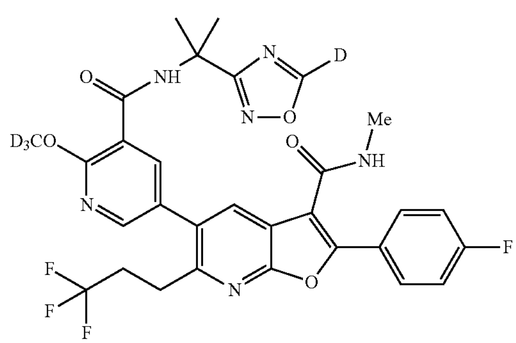 | | 3.15E-03 |
| Example 25 | 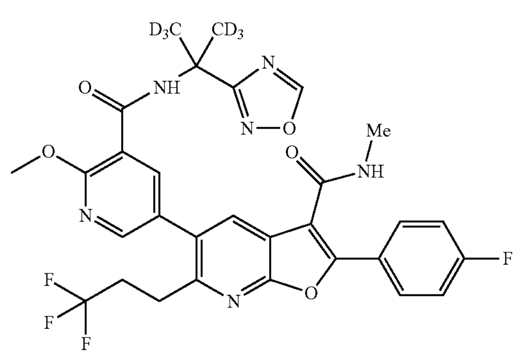 [SMILES: [2H]C([2H])([2H])C(NC(=O)c1cc(-c2cc3c(C(=O)NC)c(-c4ccc(F)cc4)oc3nc2CCC(F)(F)F)cnc1OC)(c1ncon1)C([2H])([2H])[2H]] | | 3.33E-03 |

TABLE 2-continued

| Example | Structure | EC$_{50}$, (µM) | IC$_{50}$ (µM) |
|---|---|---|---|
| Example 26 | 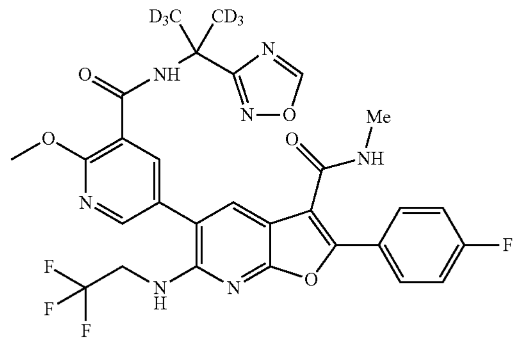 | | 6.26E−03 |
| Example 27 | 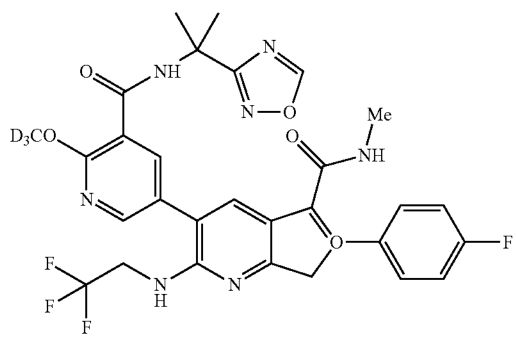 | | 4.32E−03 |
| Example 28 | 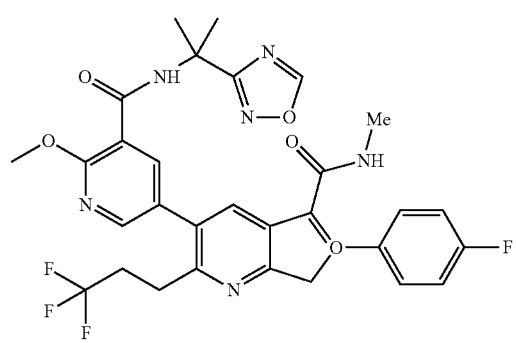 | | 4.63E−03 |
| Example 29 | 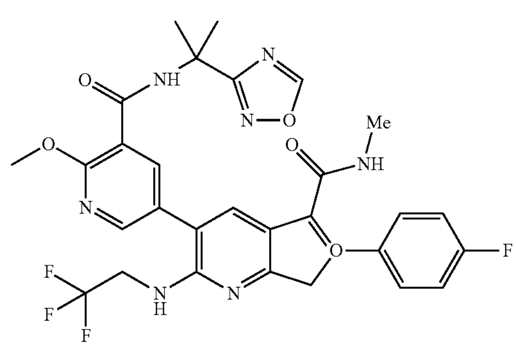 | | 8.01E−03 |

TABLE 2-continued

| Example | Structure | EC$_{50}$, (µM) | IC$_{50}$ (µM) |
| --- | --- | --- | --- |
| Example 30 | 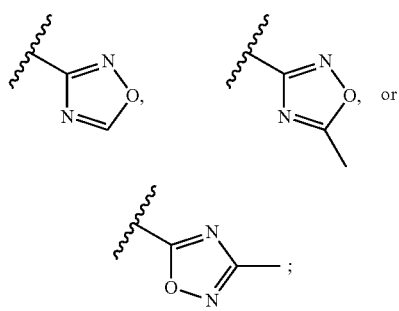 | | 4.35E−03 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

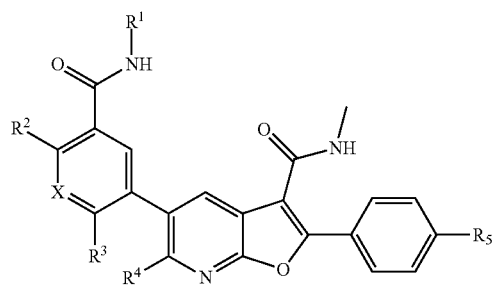

I where:
$R^1$ is

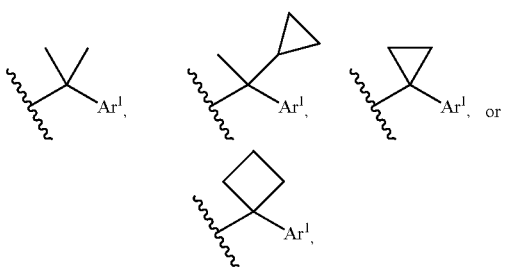

where the alkyl, cycloalkyl, or $Ar^1$ moieties may have hydrogen or deuterium atoms;
$R^2$ is hydrogen, fluoro, methoxy, or $CD_3O$;
$R^3$ is hydrogen;
$R^4$ is s-butyl, trifluoropropyl, trifluoroethoxy, or trifluoroethylamino;
$R^5$ is fluoro;

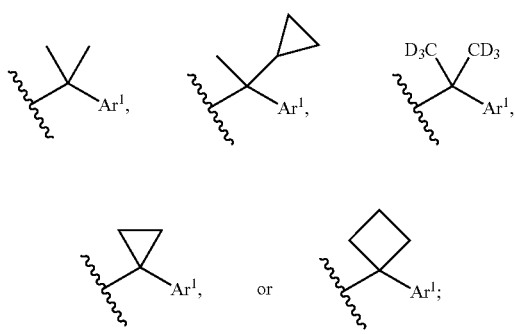

and
X is CH or N;
or a pharmaceutically acceptable salt thereof.

2. A compound of claim 1 where:
$R^1$ is

[structures]

$R^2$ is hydrogen, fluoro, methoxy, or $CD_3O$;
$R^3$ is hydrogen;
$R^4$ is s-butyl, trifluoropropyl, trifluoroethoxy, or trifluoroethylamino;
$R^5$ is fluoro;

Ar¹ is
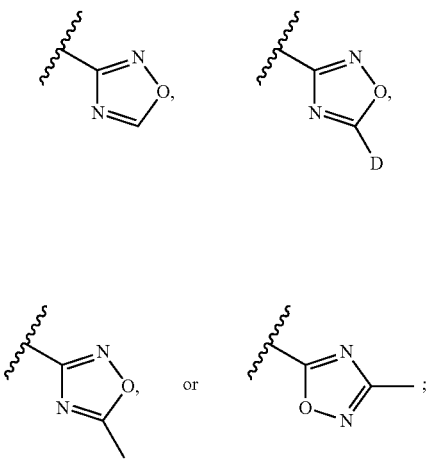
and
X is CH or N;
or a pharmaceutically acceptable salt thereof.
3. A compound of claim 1 selected from the group consisting of
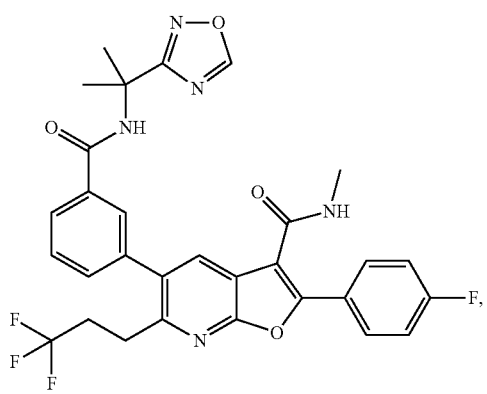 [SMILES: CNC(=O)c1c(-c2ccc(F)cc2)oc2nc(CCC(F)(F)F)c(-c3cccc(C(=O)NC(C)(C)c4ncon4)c3)cc12]
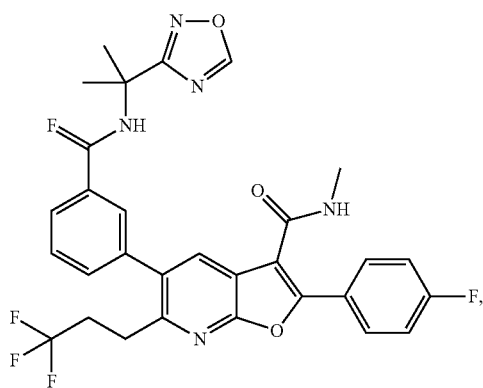
-continued
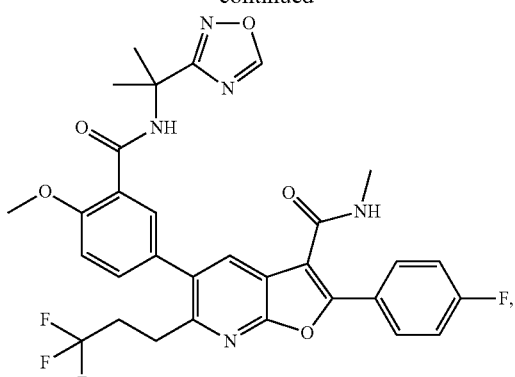
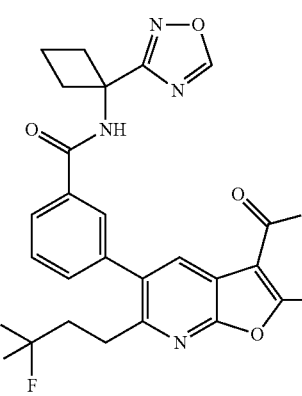
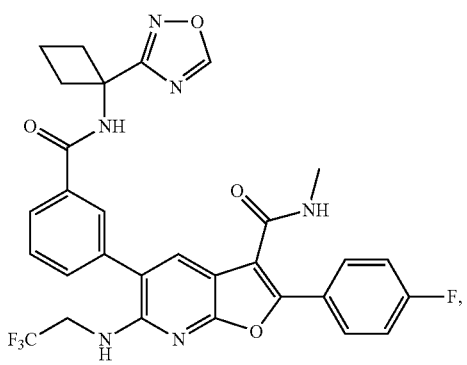
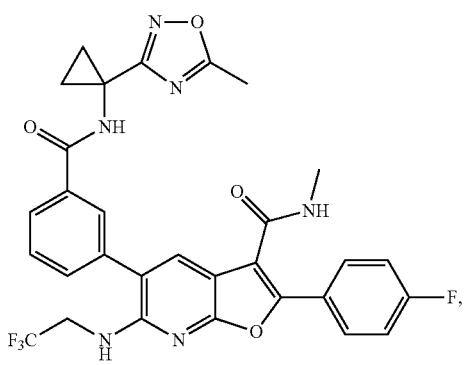

97
-continued
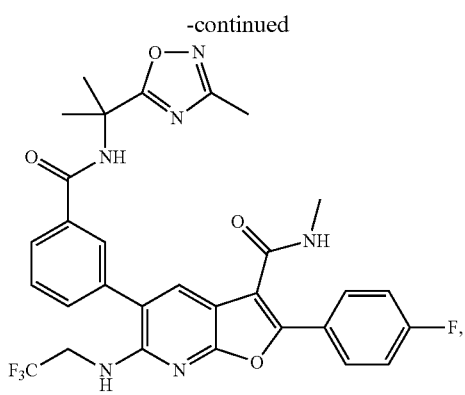
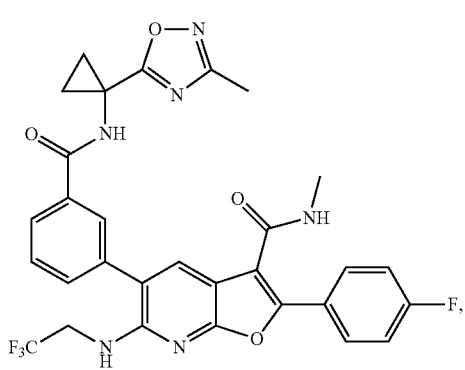
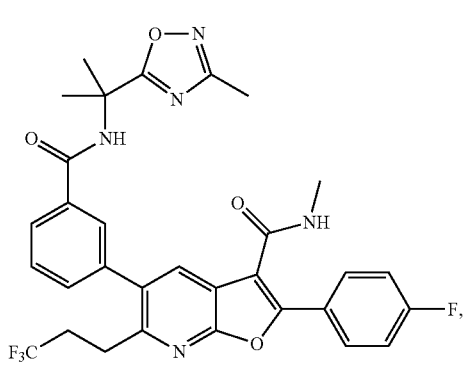
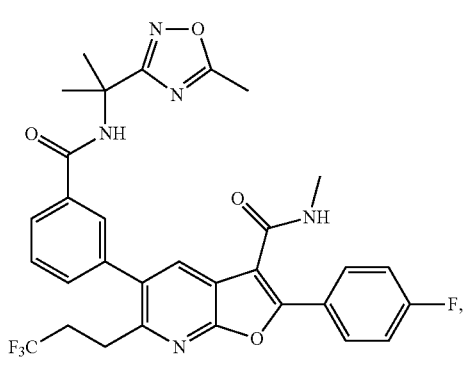
98
-continued
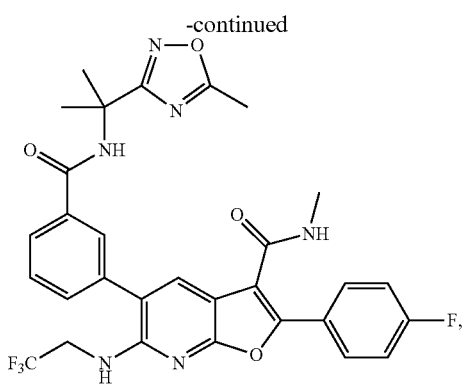
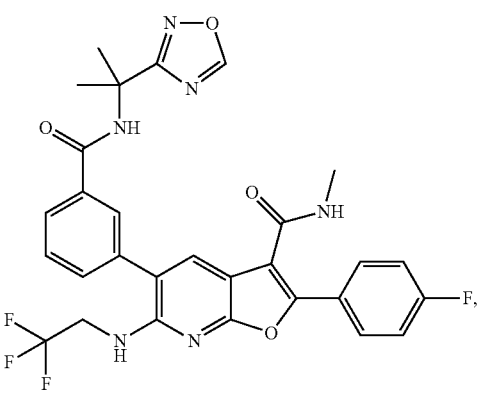
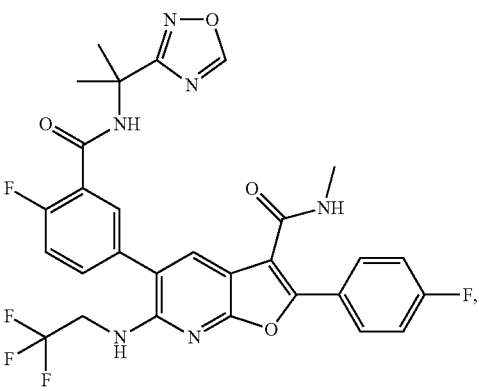
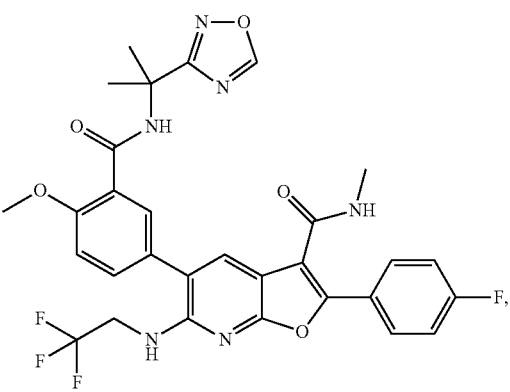

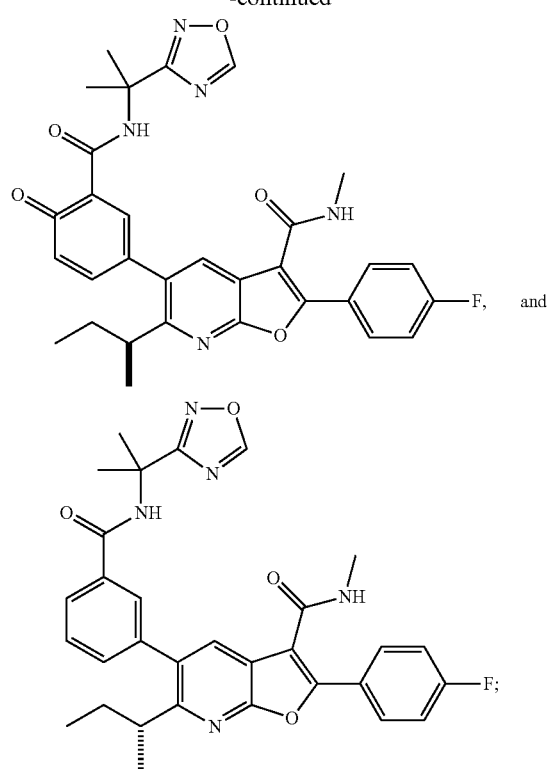
or a pharmaceutically acceptable salt thereof.
4. A compound of claim 1 selected from the group consisting of
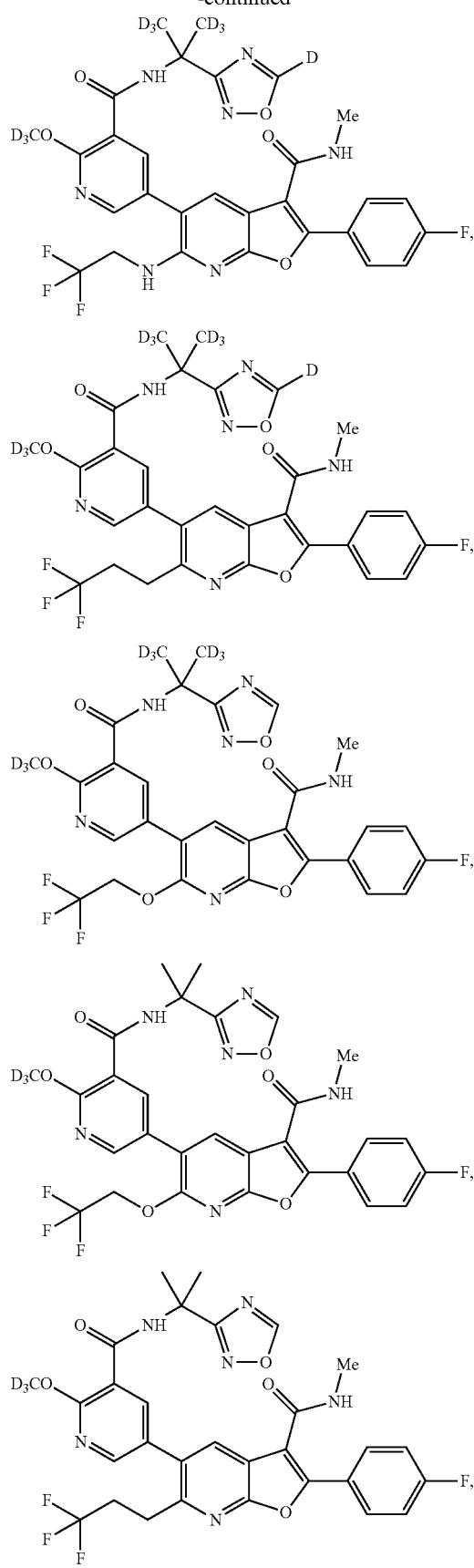

-continued

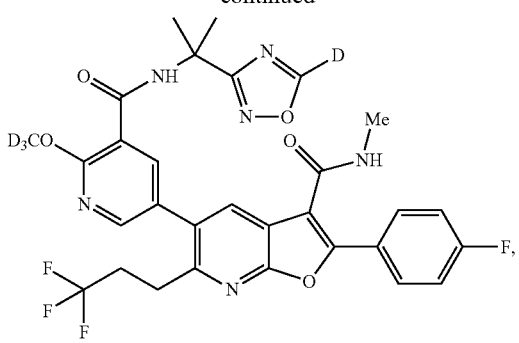

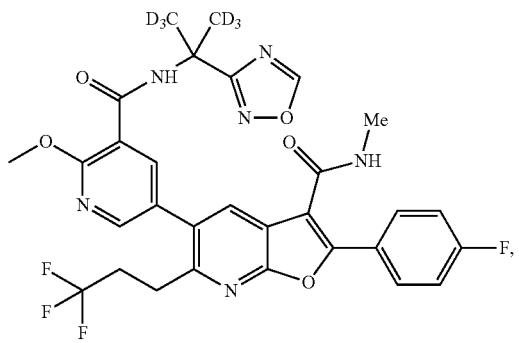

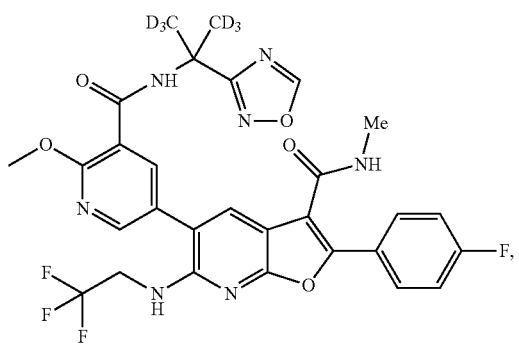

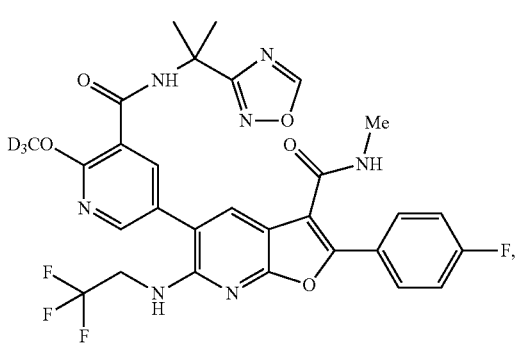

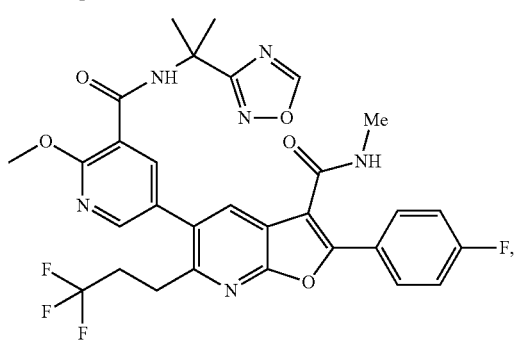

-continued

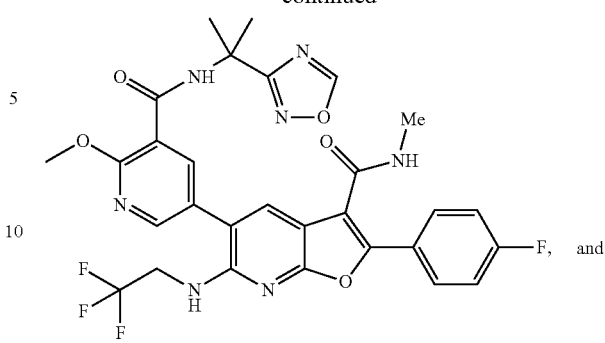

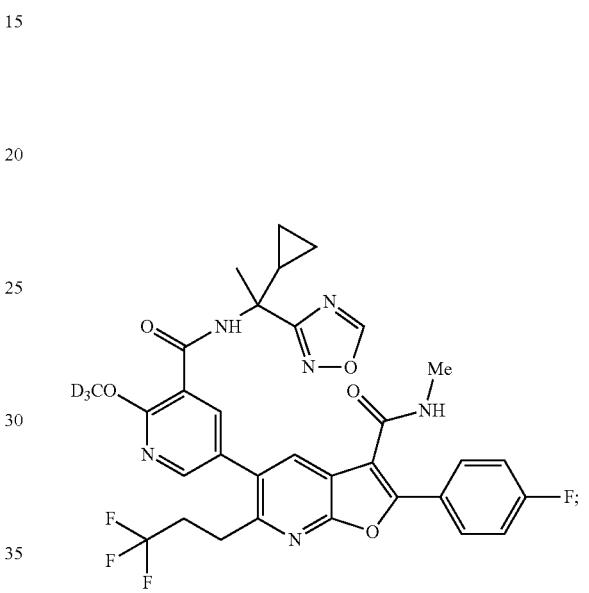

or a pharmaceutically acceptable salt thereof.

5. The compound of claim 1: 5-(3-((2-(1,2,4-oxadiazol-3-yl)propan-2-yl)carbamoyl)phenyl)-2-(4-fluorophenyl)-N-methyl-6-(3,3,3-trifluoropropyl)furo[2,3-b]pyridine-3-carboxamide, or a pharmaceutically acceptable salt thereof

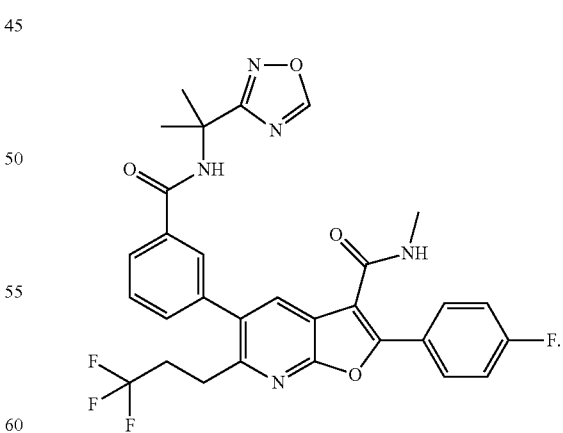

6. The compound of claim 1: 5-[2-(4-fluorophenyl)-3-(methylcarbamoyl)-6-(3,3,3-trifluoropropyl)furo[2,3-b]pyridin-5-yl]-2-($^2H_3$)methoxy-N-[2-(1,2,4-oxadiazol-3-yl)($^2H_6$)propan-2-yl]pyridine-3-carboxamide, or a pharmaceutically acceptable salt thereof.

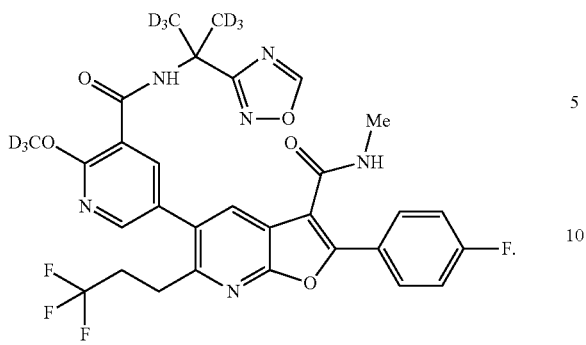
7. A composition comprising a compound of claim 1, or a pharmaceutically acceptable salt thereof, and a pharmaceutically acceptable carrier.
8. A method of treating hepatitis C infection comprising administering a therapeutically effective amount of a compound of claim 1 to a patient.
* * * * *